(12) United States Patent
Debelak et al.

(10) Patent No.: US 8,349,812 B2
(45) Date of Patent: Jan. 8, 2013

(54) IMMUNE STIMULATORY OLIGORIBONUCLEOTIDE ANALOGS CONTAINING MODIFIED OLIGOPHOSPHATE MOIETIES

(75) Inventors: Harald Debelak, Hilden (DE); Eugen Uhlmann, Glashütten (DE)

(73) Assignee: AdiuTide Pharmaceuticals GmbH, Frankfurt am Main (DE)

( * ) Notice: Subject to any disclaimer, the term of this patent is extended or adjusted under 35 U.S.C. 154(b) by 341 days.

(21) Appl. No.: 12/741,634

(22) PCT Filed: Oct. 30, 2008

(86) PCT No.: PCT/IB2008/002940
§ 371 (c)(1),
(2), (4) Date: May 6, 2010

(87) PCT Pub. No.: WO2009/060281
PCT Pub. Date: May 14, 2009

(65) Prior Publication Data
US 2010/0260788 A1 Oct. 14, 2010

Related U.S. Application Data

(60) Provisional application No. 61/002,049, filed on Nov. 6, 2007.

(51) Int. Cl.
*A01N 43/04* (2006.01)
*A61K 31/70* (2006.01)
(52) U.S. Cl. .......... 514/52; 514/43; 536/22.1; 536/23.1; 536/25.4; 536/26.2; 536/26.21; 536/26.26

(58) Field of Classification Search ........................ None
See application file for complete search history.

(56) References Cited

U.S. PATENT DOCUMENTS
2006/0178334 A1 8/2006 Rossi

FOREIGN PATENT DOCUMENTS
FR    1 566 530 A    5/1969

OTHER PUBLICATIONS

Lebedev, et al. "Preparation of Oligodeoxynucleotide 5'-Triphosphates Using Solid Support Approach," Nucleosides, Nucleotides and Nucleic Acids, vol. 20 (4-7), pp. 1403-1409 (2001).

*Primary Examiner* — Patrick Lewis
(74) *Attorney, Agent, or Firm* — Chalin A. Smith; Smith Patent Consulting

(57) ABSTRACT

Immunostimulatory oligoribonucleotides (ORN) featuring 5'-triphosphates and various 5'-triphosphate analogs are provided. Also provided are physiologically acceptable salts of the immunostimulatory ORN and pharmaceutical compositions containing the immunostimulatory ORN of the invention. ORN of the invention are useful as adjuvants and can be combined with an antigen to promote an antigen-specific immune response. ORN of the invention are also particularly useful for promoting a Th1-type immune response. Also provided are methods of use of the compounds and pharmaceutical compositions of the invention to enhance an immune response in a subject, as well to treat a number of conditions including cancer, infection, allergy, and asthma, and to vaccinate a subject against an antigen.

4 Claims, 2 Drawing Sheets

SEQUENCE LISTING

```
<160> NUMBER OF SEQ ID NOS: 508

<210> SEQ ID NO 1
<211> LENGTH: 12
<212> TYPE: RNA
<213> ORGANISM: Artificial Sequence
<220> FEATURE:
<223> OTHER INFORMATION: synthetic oligonucleotide

<400> SEQUENCE: 1
aaaaaaaaaa aa                                                         12

<210> SEQ ID NO 2
<211> LENGTH: 10
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(10)
<223> OTHER INFORMATION: n represents thymine ribonucleotidehymine
      ribonucleotide

<400> SEQUENCE: 2 nnnnnnnnnn                                                            10

<210> SEQ ID NO 3
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 3
aaaauaaaau aaaauaaaau                                                 20
```

```
<210> SEQ ID NO 4
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 4
aaaaucauca ucucuuguuu uugugugucu                                     30

<210> SEQ ID NO 5
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 5
aaacaacaaa cacacaaacc                                                20

<210> SEQ ID NO 6
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 6
aaacucuugu cuggu                                                     15

<210> SEQ ID NO 7
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 7
aaauaaauaa auaaauaaau                                                20

<210> SEQ ID NO 8
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 8
aacacguauc cauauuuccc cuuguucggu                                     30

<210> SEQ ID NO 9
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 9
aacaucuacc ugcuuuugcu                                                20

<210> SEQ ID NO 10
<211> LENGTH: 26
<212> TYPE: RNA
<213> ORGANISM: Artificial Sequence
<220> FEATURE:
<223> OTHER INFORMATION: synthetic oligonucleotide
```

```
<400> SEQUENCE: 10
aacauuauua accccugcu ucugcu                                          26

<210> SEQ ID NO 11
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 11
aacccugcuu uugcu                                                     15

<210> SEQ ID NO 12
<211> LENGTH: 23
<212> TYPE: RNA
<213> ORGANISM: Artificial Sequence
<220> FEATURE:
<223> OTHER INFORMATION: synthetic oligonucleotide

<400> SEQUENCE: 12
aacuggacuu ccagaagaac auu                                            23

<210> SEQ ID NO 13
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 13
aauaucuacc ugcuuucgcu                                                20

<210> SEQ ID NO 14
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 14
aauaucuacc ugcuuuugcu                                                20

<210> SEQ ID NO 15
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 15
aaucacuaua guuuuuugu uuuucuccgu                                      30

<210> SEQ ID NO 16
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 16
aaucaguacc ugcuuucgcu                                                20

<210> SEQ ID NO 17
<211> LENGTH: 20
<212> TYPE: RNA
```

```
<213> ORGANISM: Artificial Sequence
<220> FEATURE:
<223> OTHER INFORMATION: synthetic oligonucleotide

<400> SEQUENCE: 17
aaucaguacc ugcuuuugcu                                               20

<210> SEQ ID NO 18
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 18
aaucuccugc uuuug                                                    15

<210> SEQ ID NO 19
<211> LENGTH: 10
<212> TYPE: RNA
<213> ORGANISM: Artificial Sequence
<220> FEATURE:
<223> OTHER INFORMATION: synthetic oligonucleotide

<400> SEQUENCE: 19
aaucuuagcu                                                          10

<210> SEQ ID NO 20
<211> LENGTH: 23
<212> TYPE: RNA
<213> ORGANISM: Artificial Sequence
<220> FEATURE:
<223> OTHER INFORMATION: synthetic oligonucleotide

<400> SEQUENCE: 20
aaugcugacu ccaaagcucu guu                                           23

<210> SEQ ID NO 21
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 21
aaugguuuau uugucuucgu                                               20

<210> SEQ ID NO 22
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 22
aaugguuugu uugucuucgu                                               20

<210> SEQ ID NO 23
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 23
aaugguuuuu uugucuucgu                                               20
```

-continued

```
<210> SEQ ID NO 24
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 24 aauuucccc ugcuuugcu                                                  20

<210> SEQ ID NO 25
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 25
acccaucuau uauauaacuc                                                20

<210> SEQ ID NO 26
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 26
accccugcuu uugcu                                                     15

<210> SEQ ID NO 27
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 27
accgauaucc caucuucauu uuccccuugg                                     30

<210> SEQ ID NO 28
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 28
acuccugcuu uugcu                                                     15

<210> SEQ ID NO 29
<211> LENGTH: 26
<212> TYPE: RNA
<213> ORGANISM: Artificial Sequence
<220> FEATURE:
<223> OTHER INFORMATION: synthetic oligonucleotide

<400> SEQUENCE: 29
agccauuuug acugccuguu uuugcu                                         26

<210> SEQ ID NO 30
<211> LENGTH: 20
<212> TYPE: RNA
<213> ORGANISM: Artificial Sequence
<220> FEATURE:
<223> OTHER INFORMATION: synthetic oligonucleotide
```

```
<400> SEQUENCE: 30
agcgaaagca ggucaauuau                                               20

<210> SEQ ID NO 31
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 31
agcuccgcuu cugcu                                                    15

<210> SEQ ID NO 32
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 32
agucucuucu cuuguuuggu                                               20

<210> SEQ ID NO 33
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 33
aguuucuucu cuuguuuggu                                               20

<210> SEQ ID NO 34
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 34
aguuuuuccu cuuguuuggu                                               20

<210> SEQ ID NO 35
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 35
aguuuuuucu cuuguuuggu                                               20

<210> SEQ ID NO 36
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 36
auaauugacc ugcuuucgcu                                               20

<210> SEQ ID NO 37
<211> LENGTH: 20
<212> TYPE: RNA
```

-continued

```
<213> ORGANISM: Artificial Sequence
<220> FEATURE:
<223> OTHER INFORMATION: synthetic oligonucleotide

<400> SEQUENCE: 37
auaauugacc ugcuuuucgu                                              20

<210> SEQ ID NO 38
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 38
auaauugcgc ugcuuucgcu                                              20

<210> SEQ ID NO 39
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 39
auauauauau auauauauau                                              20

<210> SEQ ID NO 40
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 40
auaucaauua guuuuuugu uuuuucucgu                                    30

<210> SEQ ID NO 41
<211> LENGTH: 26
<212> TYPE: RNA
<213> ORGANISM: Artificial Sequence
<220> FEATURE:
<223> OTHER INFORMATION: synthetic oligonucleotide

<400> SEQUENCE: 41
auauuagaaa augcaacgcu ucugcu                                       26

<210> SEQ ID NO 42
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 42
auauucauuc ucccuuggu                                               20

<210> SEQ ID NO 43
<211> LENGTH: 12
<212> TYPE: RNA
<213> ORGANISM: Artificial Sequence
<220> FEATURE:
<223> OTHER INFORMATION: synthetic oligonucleotide

<400> SEQUENCE: 43 auauuuucg gc                                                       12
```

```
<210> SEQ ID NO 44
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 44
aucaucaucu uuuuugauac                                               20

<210> SEQ ID NO 45
<211> LENGTH: 24
<212> TYPE: RNA
<213> ORGANISM: Artificial Sequence
<220> FEATURE:
<223> OTHER INFORMATION: synthetic oligonucleotide

<400> SEQUENCE: 45
aucaucucuu guuuugugu gucu                                           24

<210> SEQ ID NO 46
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 46
auccauucaa augguuucgc ugcuuucgcu                                    30

<210> SEQ ID NO 47
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 47
auccauucaa augguuugcc ugcuuucgcu                                    30

<210> SEQ ID NO 48
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 48
auccauucaa augguuugcc ugcuuuugcu                                    30

<210> SEQ ID NO 49
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 49
auccauucaa gugguuugcc ugcuuuugcu                                    30

<210> SEQ ID NO 50
<211> LENGTH: 30
<212> TYPE: RNA
<213> ORGANISM: Artificial Sequence
<220> FEATURE:
<223> OTHER INFORMATION: synthetic oligonucleotide
```

```
<400> SEQUENCE: 50
aucccauaca uguuuuucu cuuguuuggu                                    30

<210> SEQ ID NO 51
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 51
aucucuuguu uuuguguguc                                              20

<210> SEQ ID NO 52
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 52
aucuucauuu uccccuuggu                                              20

<210> SEQ ID NO 53
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 53
aucuucuuuu uccccuuggu                                              20

<210> SEQ ID NO 54
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 54
augguuucgc ugcuuucgcu                                              20

<210> SEQ ID NO 55
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 55
augguuugcc ugcuuucgcu                                              20

<210> SEQ ID NO 56
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 56
augguuugcc ugcuuuugcu                                              20

<210> SEQ ID NO 57
<211> LENGTH: 20
<212> TYPE: RNA
```

```
-continued

<213> ORGANISM: Artificial Sequence
<220> FEATURE:
<223> OTHER INFORMATION: synthetic oligonucleotide

<400> SEQUENCE: 57
augguuuuuu uguuaagcgu                                              20

<210> SEQ ID NO 58
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 58
augucaucuu gaaaacgcuc cgcuucugcu                                   30

<210> SEQ ID NO 59
<211> LENGTH: 26
<212> TYPE: RNA
<213> ORGANISM: Artificial Sequence
<220> FEATURE:
<223> OTHER INFORMATION: synthetic oligonucleotide

<400> SEQUENCE: 59
auucaaaugg uuugccugcu uucgcu                                       26

<210> SEQ ID NO 60
<211> LENGTH: 26
<212> TYPE: RNA
<213> ORGANISM: Artificial Sequence
<220> FEATURE:
<223> OTHER INFORMATION: synthetic oligonucleotide

<400> SEQUENCE: 60
auucauuuua aaccccugcu uucgcu                                       26

<210> SEQ ID NO 61
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 61
auuccaaaca aguuucuucu cuuguuuggu                                   30

<210> SEQ ID NO 62
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 62
auuccaaaca aguuuuccu cuuguuuggu                                    30

<210> SEQ ID NO 63
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 63
auuccaaaca uguuucuucu cuuguuuggu                                   30
```

```
<210> SEQ ID NO 64
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 64
auuccauaca cguuuuucu cuugucuggu                                      30

<210> SEQ ID NO 65
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 65
auuccauaca uguuucuucu cuuguuuggu                                     30

<210> SEQ ID NO 66
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 66
auuccaugca aguuuuucu cuuguuuggu                                      30

<210> SEQ ID NO 67
<211> LENGTH: 25
<212> TYPE: RNA
<213> ORGANISM: Artificial Sequence
<220> FEATURE:
<223> OTHER INFORMATION: synthetic oligonucleotide

<400> SEQUENCE: 67
auucuucuuu cuuuugugu guccg                                           25

<210> SEQ ID NO 68
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 68
auugguuugu uuucuucgu                                                 20

<210> SEQ ID NO 69
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 69
auugguuuuu uugucuucgu                                                20

<210> SEQ ID NO 70
<211> LENGTH: 30
<212> TYPE: RNA
<213> ORGANISM: Artificial Sequence
<220> FEATURE:
<223> OTHER INFORMATION: synthetic oligonucleotide
```

<400> SEQUENCE: 70
auuuggauuc auuuuaaucu ccugcuuuug                             30

<210> SEQ ID NO 71
<211> LENGTH: 26
<212> TYPE: RNA
<213> ORGANISM: Artificial Sequence
<220> FEATURE:
<223> OTHER INFORMATION: synthetic oligonucleotide

<400> SEQUENCE: 71
auuuuaagaa agugcgugcu ucugcu                                 26

<210> SEQ ID NO 72
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 72
auuuuaaucu ccugcuuuug                                        20

<210> SEQ ID NO 73
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 73
auuuuccccu gcuuuugcua                                        20

<210> SEQ ID NO 74
<211> LENGTH: 26
<212> TYPE: RNA
<213> ORGANISM: Artificial Sequence
<220> FEATURE:
<223> OTHER INFORMATION: synthetic oligonucleotide

<400> SEQUENCE: 74
auuuuggauc aguaccugcu uucgcu                                 26

<210> SEQ ID NO 75
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 75
caaaaucauc aucucuuguu uuguguguc                              30

<210> SEQ ID NO 76
<211> LENGTH: 40
<212> TYPE: RNA
<213> ORGANISM: Artificial Sequence
<220> FEATURE:
<223> OTHER INFORMATION: synthetic oligonucleotide

<400> SEQUENCE: 76
cacacacugc uuaagcgcuu gccugcuuaa guagugugug                  40

<210> SEQ ID NO 77
<211> LENGTH: 15
<212> TYPE: RNA

```
<213> ORGANISM: Artificial Sequence
<220> FEATURE:
<223> OTHER INFORMATION: synthetic oligonucleotide

<400> SEQUENCE: 77
cacccugcuu uugcu                                                    15

<210> SEQ ID NO 78
<211> LENGTH: 21
<212> TYPE: RNA
<213> ORGANISM: Artificial Sequence
<220> FEATURE:
<223> OTHER INFORMATION: synthetic oligonucleotide

<400> SEQUENCE: 78
cagagcuuug gagucagcau u                                             21

<210> SEQ ID NO 79
<211> LENGTH: 12
<212> TYPE: RNA
<213> ORGANISM: Artificial Sequence
<220> FEATURE:
<223> OTHER INFORMATION: synthetic oligonucleotide

<400> SEQUENCE: 79
caggucugug au                                                       12

<210> SEQ ID NO 80
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 80
cagugaguga uuaucaaccc ugcuuuugcu                                    30

<210> SEQ ID NO 81
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 81
cagugaguga uuauuaaccc ugcuuuugcu                                    30

<210> SEQ ID NO 82
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 82
cauagccaac uuuuucuggu                                               20

<210> SEQ ID NO 83
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 83
cauauucaau auaauugacc ugcuuuucgu                                    30
```

```
<210> SEQ ID NO 84
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 84
cauauugaau auaauugacc ugcuuucgcu                                      30

<210> SEQ ID NO 85
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 85
cauauugaau auaauugcgc ugcuuucgcu                                      30

<210> SEQ ID NO 86
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 86
cauauuuccc cuuguucggu                                                 20

<210> SEQ ID NO 87
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 87
caucuucauu uuccccuugg                                                 20

<210> SEQ ID NO 88
<211> LENGTH: 26
<212> TYPE: RNA
<213> ORGANISM: Artificial Sequence
<220> FEATURE:
<223> OTHER INFORMATION: synthetic oligonucleotide

<400> SEQUENCE: 88
caucuugaaa acgcuccgcu ucugcu                                          26

<210> SEQ ID NO 89
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 89
caucuuuuau gauac                                                      15

<210> SEQ ID NO 90
<211> LENGTH: 15
<212> TYPE: RNA
<213> ORGANISM: Artificial Sequence
<220> FEATURE:
<223> OTHER INFORMATION: synthetic oligonucleotide
```

```
<400> SEQUENCE: 90
caucuuuuuu gauac                                                15

<210> SEQ ID NO 91
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 91
cauucucccc uuggu                                                15

<210> SEQ ID NO 92
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 92
cauugaguga uuaucuaccc ugcuuuugcu                                30

<210> SEQ ID NO 93
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 93
cauuuccccc uuggu                                                15

<210> SEQ ID NO 94
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 94
ccaacauccc aucuucuuuu uccccuuggu                                30

<210> SEQ ID NO 95
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 95
ccaacuuugu cuggu                                                15

<210> SEQ ID NO 96
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 96
ccaacuuugu uuggu                                                15

<210> SEQ ID NO 97
<211> LENGTH: 15
<212> TYPE: RNA
```

```
<213> ORGANISM: Artificial Sequence
<220> FEATURE:
<223> OTHER INFORMATION: synthetic oligonucleotide

<400> SEQUENCE: 97
ccaacuuuuu cuggu                                                    15

<210> SEQ ID NO 98
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 98
ccaauauccc auauucauuc uccccuuggu                                    30

<210> SEQ ID NO 99
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 99
ccaauauccc aucuucauuu uccccuuggu                                    30

<210> SEQ ID NO 100
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 100
ccagcuuugu cuggu                                                    15

<210> SEQ ID NO 101
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 101
ccagcuuugu uuggu                                                    15

<210> SEQ ID NO 102
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 102
ccauuauguc uuugucaccc ugcuuuugcu                                    30

<210> SEQ ID NO 103
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 103
ccccugcuuu ugcua                                                    15
```

-continued

<210> SEQ ID NO 104
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 104
ccccuuuugg ggg                                                          13

<210> SEQ ID NO 105
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 105
cccugcuuuu gcuaa                                                        15

<210> SEQ ID NO 106
<211> LENGTH: 16
<212> TYPE: RNA
<213> ORGANISM: Artificial Sequence
<220> FEATURE:
<223> OTHER INFORMATION: synthetic oligonucleotide

<400> SEQUENCE: 106
ccgagccaua uauauc                                                       16

<210> SEQ ID NO 107
<211> LENGTH: 16
<212> TYPE: RNA
<213> ORGANISM: Artificial Sequence
<220> FEATURE:
<223> OTHER INFORMATION: synthetic oligonucleotide

<400> SEQUENCE: 107
ccgagccaua uauccc                                                       16

<210> SEQ ID NO 108
<211> LENGTH: 16
<212> TYPE: RNA
<213> ORGANISM: Artificial Sequence
<220> FEATURE:
<223> OTHER INFORMATION: synthetic oligonucleotide

<400> SEQUENCE: 108
ccgagccgaa gauacc                                                       16

<210> SEQ ID NO 109
<211> LENGTH: 16
<212> TYPE: RNA
<213> ORGANISM: Artificial Sequence
<220> FEATURE:
<223> OTHER INFORMATION: synthetic oligonucleotide

<400> SEQUENCE: 109
ccgagccgaa gcuacc                                                       16

<210> SEQ ID NO 110
<211> LENGTH: 16
<212> TYPE: RNA
<213> ORGANISM: Artificial Sequence
<220> FEATURE:
<223> OTHER INFORMATION: synthetic oligonucleotide

```
<400> SEQUENCE: 110
ccgagccgaa gcuccc                                                   16

<210> SEQ ID NO 111
<211> LENGTH: 16
<212> TYPE: RNA
<213> ORGANISM: Artificial Sequence
<220> FEATURE:
<223> OTHER INFORMATION: synthetic oligonucleotide

<400> SEQUENCE: 111
ccgagccgaa gcugcc                                                   16

<210> SEQ ID NO 112
<211> LENGTH: 16
<212> TYPE: RNA
<213> ORGANISM: Artificial Sequence
<220> FEATURE:
<223> OTHER INFORMATION: synthetic oligonucleotide

<400> SEQUENCE: 112
ccgagccgaa ggcacc                                                   16

<210> SEQ ID NO 113
<211> LENGTH: 16
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(16)
<223> OTHER INFORMATION: phosphorothioate internucleotide linkages

<400> SEQUENCE: 113
ccgagccgaa ggcacc                                                   16

<210> SEQ ID NO 114
<211> LENGTH: 16
<212> TYPE: RNA
<213> ORGANISM: Artificial Sequence
<220> FEATURE:
<223> OTHER INFORMATION: synthetic oligonucleotide

<400> SEQUENCE: 114
ccgagccgaa gguacc                                                   16

<210> SEQ ID NO 115
<211> LENGTH: 16
<212> TYPE: RNA
<213> ORGANISM: Artificial Sequence
<220> FEATURE:
<223> OTHER INFORMATION: synthetic oligonucleotide

<400> SEQUENCE: 115
ccgagccgaa gguccc                                                   16

<210> SEQ ID NO 116
<211> LENGTH: 16
<212> TYPE: RNA
<213> ORGANISM: Artificial Sequence
<220> FEATURE:
<223> OTHER INFORMATION: synthetic oligonucleotide

<400> SEQUENCE: 116
ccgagccgaa ggugcc                                                   16
```

```
<210> SEQ ID NO 117
<211> LENGTH: 16
<212> TYPE: RNA
<213> ORGANISM: Artificial Sequence
<220> FEATURE:
<223> OTHER INFORMATION: synthetic oligonucleotide

<400> SEQUENCE: 117
ccgagccgaa uaaccc                                                        16

<210> SEQ ID NO 118
<211> LENGTH: 16
<212> TYPE: RNA
<213> ORGANISM: Artificial Sequence
<220> FEATURE:
<223> OTHER INFORMATION: synthetic oligonucleotide

<400> SEQUENCE: 118
ccgagccgaa ucaccc                                                        16

<210> SEQ ID NO 119
<211> LENGTH: 16
<212> TYPE: RNA
<213> ORGANISM: Artificial Sequence
<220> FEATURE:
<223> OTHER INFORMATION: synthetic oligonucleotide

<400> SEQUENCE: 119
ccgagccgaa uguacc                                                        16

<210> SEQ ID NO 120
<211> LENGTH: 16
<212> TYPE: RNA
<213> ORGANISM: Artificial Sequence
<220> FEATURE:
<223> OTHER INFORMATION: synthetic oligonucleotide

<400> SEQUENCE: 120
ccgagccgaa uucacc                                                        16

<210> SEQ ID NO 121
<211> LENGTH: 16
<212> TYPE: RNA
<213> ORGANISM: Artificial Sequence
<220> FEATURE:
<223> OTHER INFORMATION: synthetic oligonucleotide

<400> SEQUENCE: 121
ccgagccgaa uuuacc                                                        16

<210> SEQ ID NO 122
<211> LENGTH: 18
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(18)
<223> OTHER INFORMATION: phosphorothioate internucleotide linkages
<220> FEATURE:
<221> NAME/KEY: modified_base
<222> LOCATION: (3)..(3)
<223> OTHER INFORMATION: gm (2'-O-methyl guanosine)

<400> SEQUENCE: 122
ccgagccgac cuuguacc                                                      18
```

```
<210> SEQ ID NO 123
<211> LENGTH: 16
<212> TYPE: RNA
<213> ORGANISM: Artificial Sequence
<220> FEATURE:
<223> OTHER INFORMATION: synthetic oligonucleotide

<400> SEQUENCE: 123
ccgagccgac uguacc                                                     16

<210> SEQ ID NO 124
<211> LENGTH: 16
<212> TYPE: RNA
<213> ORGANISM: Artificial Sequence
<220> FEATURE:
<223> OTHER INFORMATION: synthetic oligonucleotide

<400> SEQUENCE: 124
ccgagccgac uuuacc                                                     16

<210> SEQ ID NO 125
<211> LENGTH: 16
<212> TYPE: RNA
<213> ORGANISM: Artificial Sequence
<220> FEATURE:
<223> OTHER INFORMATION: synthetic oligonucleotide

<400> SEQUENCE: 125
ccgagccgag cucacc                                                     16

<210> SEQ ID NO 126
<211> LENGTH: 16
<212> TYPE: RNA
<213> ORGANISM: Artificial Sequence
<220> FEATURE:
<223> OTHER INFORMATION: synthetic oligonucleotide

<400> SEQUENCE: 126
ccgagccgag uucacc                                                     16

<210> SEQ ID NO 127
<211> LENGTH: 16
<212> TYPE: RNA
<213> ORGANISM: Artificial Sequence
<220> FEATURE:
<223> OTHER INFORMATION: synthetic oligonucleotide

<400> SEQUENCE: 127
ccgagccgag uuuacc                                                     16

<210> SEQ ID NO 128
<211> LENGTH: 16
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (10)..(10)
<223> OTHER INFORMATION: n represents a, c, g, u, t, or i (inosine)

<400> SEQUENCE: 128
ccgagccgan uguacc                                                     16

<210> SEQ ID NO 129
<211> LENGTH: 16
<212> TYPE: RNA
```

```
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (10)..(10)
<223> OTHER INFORMATION: n represents a, c, g, u, t, or i (inosine)

<400> SEQUENCE: 129
ccgagccgan uucacc                                                     16

<210> SEQ ID NO 130
<211> LENGTH: 16
<212> TYPE: RNA
<213> ORGANISM: Artificial Sequence
<220> FEATURE:
<223> OTHER INFORMATION: synthetic oligonucleotide

<400> SEQUENCE: 130
ccgagccgau auuacc                                                     16

<210> SEQ ID NO 131
<211> LENGTH: 16
<212> TYPE: RNA
<213> ORGANISM: Artificial Sequence
<220> FEATURE:
<223> OTHER INFORMATION: synthetic oligonucleotide

<400> SEQUENCE: 131
ccgagccgau cucacc                                                     16

<210> SEQ ID NO 132
<211> LENGTH: 16
<212> TYPE: RNA
<213> ORGANISM: Artificial Sequence
<220> FEATURE:
<223> OTHER INFORMATION: synthetic oligonucleotide

<400> SEQUENCE: 132
ccgagccgau cuuacc                                                     16

<210> SEQ ID NO 133
<211> LENGTH: 16
<212> TYPE: RNA
<213> ORGANISM: Artificial Sequence
<220> FEATURE:
<223> OTHER INFORMATION: synthetic oligonucleotide

<400> SEQUENCE: 133
ccgagccgau guuacc                                                     16

<210> SEQ ID NO 134
<211> LENGTH: 16
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (11)..(11)
<223> OTHER INFORMATION: n represents a, c, g, u, t, or i (inosine)
<220> FEATURE:
<221> NAME/KEY: misc_feature
<222> LOCATION: (13)..(13)
<223> OTHER INFORMATION: n represents a, c, g, u, t, or i (inosine)

<400> SEQUENCE: 134
ccgagccgau nunacc                                                     16
```

```
<210> SEQ ID NO 135
<211> LENGTH: 16
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (13)..(13)
<223> OTHER INFORMATION: n represents a, c, g, u, t, or i (inosine)

<400> SEQUENCE: 135
ccgagccgau ucnacc                                                       16

<210> SEQ ID NO 136
<211> LENGTH: 16
<212> TYPE: RNA
<213> ORGANISM: Artificial Sequence
<220> FEATURE:
<223> OTHER INFORMATION: synthetic oligonucleotide

<400> SEQUENCE: 136
ccgagccgau ugaacc                                                       16

<210> SEQ ID NO 137
<211> LENGTH: 16
<212> TYPE: RNA
<213> ORGANISM: Artificial Sequence
<220> FEATURE:
<223> OTHER INFORMATION: synthetic oligonucleotide

<400> SEQUENCE: 137
ccgagccgau ugcacc                                                       16

<210> SEQ ID NO 138
<211> LENGTH: 16
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(16)
<223> OTHER INFORMATION: phosphorothioate internucleotide linkages
<220> FEATURE:
<221> NAME/KEY: modified_base
<222> LOCATION: (1)..(1)
<223> OTHER INFORMATION: cm (2'-O-methyl cytidine)

<400> SEQUENCE: 138
ccgagccgau uguacc                                                       16

<210> SEQ ID NO 139
<211> LENGTH: 16
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(16)
<223> OTHER INFORMATION: phosphorothioate internucleotide linkages
<220> FEATURE:
<221> NAME/KEY: modified_base
<222> LOCATION: (7)..(7)
<223> OTHER INFORMATION: cm (2'-O-methyl cytidine)

<400> SEQUENCE: 139
ccgagccgau uguacc                                                       16
```

```
<210> SEQ ID NO 140
<211> LENGTH: 16
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(16)
<223> OTHER INFORMATION: phosphorothioate internucleotide linkages
<220> FEATURE:
<221> NAME/KEY: modified_base
<222> LOCATION: (8)..(8)
<223> OTHER INFORMATION: gm (2'-O-methyl guanosine)

<400> SEQUENCE: 140
ccgagccgau uguacc                                                    16

<210> SEQ ID NO 141
<211> LENGTH: 16
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(16)
<223> OTHER INFORMATION: phosphorothioate internucleotide linkages
<220> FEATURE:
<221> NAME/KEY: modified_base
<222> LOCATION: (9)..(9)
<223> OTHER INFORMATION: am (2'-O-methyl adenosine)

<400> SEQUENCE: 141
ccgagccgau uguacc                                                    16

<210> SEQ ID NO 142
<211> LENGTH: 16
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(16)
<223> OTHER INFORMATION: phosphorothioate internucleotide linkages
<220> FEATURE:
<221> NAME/KEY: modified_base
<222> LOCATION: (10)..(10)
<223> OTHER INFORMATION: um (2'-O-methyl uridine)

<400> SEQUENCE: 142
ccgagccgau uguacc                                                    16

<210> SEQ ID NO 143
<211> LENGTH: 16
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(16)
<223> OTHER INFORMATION: phosphorothioate internucleotide linkages
<220> FEATURE:
<221> NAME/KEY: modified_base
<222> LOCATION: (11)..(11)
<223> OTHER INFORMATION: um (2'-O-methyl uridine)

<400> SEQUENCE: 143
ccgagccgau uguacc                                                    16
```

```
<210> SEQ ID NO 144
<211> LENGTH: 16
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(16)
<223> OTHER INFORMATION: phosphorothioate internucleotide linkages
<220> FEATURE:
<221> NAME/KEY: modified_base
<222> LOCATION: (12)..(12)
<223> OTHER INFORMATION: gm (2'-O-methyl guanosine)

<400> SEQUENCE: 144
ccgagccgau uguacc                                                 16

<210> SEQ ID NO 145
<211> LENGTH: 16
<212> TYPE: RNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: (13)..(13)
<223> OTHER INFORMATION: um (2'-O-methyl uridine)
<220> FEATURE:
<221> NAME/KEY: misc_feature
<222> LOCATION: (16)..(16)
<223> OTHER INFORMATION: phosphorothioate internucleotide linkages

<400> SEQUENCE: 145
ccgagccgau uguacc                                                 16

<210> SEQ ID NO 146
<211> LENGTH: 16
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(16)
<223> OTHER INFORMATION: phosphorothioate internucleotide linkages
<220> FEATURE:
<221> NAME/KEY: modified_base
<222> LOCATION: (14)..(14)
<223> OTHER INFORMATION: am (2'-O-methyl adenosine)

<400> SEQUENCE: 146
ccgagccgau uguacc                                                 16

<210> SEQ ID NO 147
<211> LENGTH: 16
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(16)
<223> OTHER INFORMATION: phosphorothioate internucleotide linkages
<220> FEATURE:
<221> NAME/KEY: modified_base
<222> LOCATION: (15)..(15)
<223> OTHER INFORMATION: cm (2'-O-methyl cytidine)

<400> SEQUENCE: 147
ccgagccgau uguacc                                                 16
```

```
<210> SEQ ID NO 148
<211> LENGTH: 16
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(16)
<223> OTHER INFORMATION: phosphorothioate internucleotide linkages

<400> SEQUENCE: 148
ccgagccgau uguacc                                                         16

<210> SEQ ID NO 149
<211> LENGTH: 16
<212> TYPE: RNA
<213> ORGANISM: Artificial Sequence
<220> FEATURE:
<223> OTHER INFORMATION: synthetic oligonucleotide

<400> SEQUENCE: 149
ccgagccgau uuaacc                                                         16

<210> SEQ ID NO 150
<211> LENGTH: 16
<212> TYPE: RNA
<213> ORGANISM: Artificial Sequence
<220> FEATURE:
<223> OTHER INFORMATION: synthetic oligonucleotide

<400> SEQUENCE: 150
ccgagccgau uucacc                                                         16

<210> SEQ ID NO 151
<211> LENGTH: 16
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (13)..(13)
<223> OTHER INFORMATION: n represents a, c, g, u, t, or i (inosine)

<400> SEQUENCE: 151
ccgagccgau uunacc                                                         16

<210> SEQ ID NO 152
<211> LENGTH: 16
<212> TYPE: RNA
<213> ORGANISM: Artificial Sequence
<220> FEATURE:
<223> OTHER INFORMATION: synthetic oligonucleotide

<400> SEQUENCE: 152
ccgagccgca uaaccc                                                         16

<210> SEQ ID NO 153
<211> LENGTH: 16
<212> TYPE: RNA
<213> ORGANISM: Artificial Sequence
<220> FEATURE:
<223> OTHER INFORMATION: synthetic oligonucleotide

<400> SEQUENCE: 153
ccgagccgca uacccc                                                         16
```

```
<210> SEQ ID NO 154
<211> LENGTH: 16
<212> TYPE: RNA
<213> ORGANISM: Artificial Sequence
<220> FEATURE:
<223> OTHER INFORMATION: synthetic oligonucleotide

<400> SEQUENCE: 154
ccgagccgca uauccc                                                    16

<210> SEQ ID NO 155
<211> LENGTH: 16
<212> TYPE: RNA
<213> ORGANISM: Artificial Sequence
<220> FEATURE:
<223> OTHER INFORMATION: synthetic oligonucleotide

<400> SEQUENCE: 155
ccgagccgca ucccccc                                                   16

<210> SEQ ID NO 156
<211> LENGTH: 16
<212> TYPE: RNA
<213> ORGANISM: Artificial Sequence
<220> FEATURE:
<223> OTHER INFORMATION: synthetic oligonucleotide

<400> SEQUENCE: 156
ccgagccgca uuaccc                                                    16

<210> SEQ ID NO 157
<211> LENGTH: 16
<212> TYPE: RNA
<213> ORGANISM: Artificial Sequence
<220> FEATURE:
<223> OTHER INFORMATION: synthetic oligonucleotide

<400> SEQUENCE: 157
ccgagccgca uuccccc                                                   16

<210> SEQ ID NO 158
<211> LENGTH: 16
<212> TYPE: RNA
<213> ORGANISM: Artificial Sequence
<220> FEATURE:
<223> OTHER INFORMATION: synthetic oligonucleotide

<400> SEQUENCE: 158
ccgagccgcc gccccc                                                    16

<210> SEQ ID NO 159
<211> LENGTH: 16
<212> TYPE: RNA
<213> ORGANISM: Artificial Sequence
<220> FEATURE:
<223> OTHER INFORMATION: synthetic oligonucleotide

<400> SEQUENCE: 159
ccgagccgcc uaaccc                                                    16

<210> SEQ ID NO 160
<211> LENGTH: 16
<212> TYPE: RNA
<213> ORGANISM: Artificial Sequence
<220> FEATURE:
<223> OTHER INFORMATION: synthetic oligonucleotide
```

```
<400> SEQUENCE: 160
ccgagccgcc uaccc                                                        16

<210> SEQ ID NO 161
<211> LENGTH: 16
<212> TYPE: RNA
<213> ORGANISM: Artificial Sequence
<220> FEATURE:
<223> OTHER INFORMATION: synthetic oligonucleotide

<400> SEQUENCE: 161
ccgagccgcu auccc                                                        16

<210> SEQ ID NO 162
<211> LENGTH: 16
<212> TYPE: RNA
<213> ORGANISM: Artificial Sequence
<220> FEATURE:
<223> OTHER INFORMATION: synthetic oligonucleotide

<400> SEQUENCE: 162
ccgagccgcu auccc                                                        16

<210> SEQ ID NO 163
<211> LENGTH: 16
<212> TYPE: RNA
<213> ORGANISM: Artificial Sequence
<220> FEATURE:
<223> OTHER INFORMATION: synthetic oligonucleotide

<400> SEQUENCE: 163
ccgagccgcu auuccc                                                       16

<210> SEQ ID NO 164
<211> LENGTH: 16
<212> TYPE: RNA
<213> ORGANISM: Artificial Sequence
<220> FEATURE:
<223> OTHER INFORMATION: synthetic oligonucleotide

<400> SEQUENCE: 164
ccgagccgcu uaaccc                                                       16

<210> SEQ ID NO 165
<211> LENGTH: 16
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(16)
<223> OTHER INFORMATION: phosphorothioate internucleotide linkages
<220> FEATURE:
<221> NAME/KEY: modified_base
<222> LOCATION: (9)..(9)
<223> OTHER INFORMATION: cm (2'-O-methyl cytidine)

<400> SEQUENCE: 165
ccgagccgcu uguccc                                                       16

<210> SEQ ID NO 166
<211> LENGTH: 16
<212> TYPE: RNA
<213> ORGANISM: Artificial Sequence
<220> FEATURE:
<223> OTHER INFORMATION: synthetic oligonucleotide
<220> FEATURE:
```

```
<221> NAME/KEY: misc_feature
<222> LOCATION: (1)..(16)
<223> OTHER INFORMATION: phosphorothioate internucleotide linkages
<220> FEATURE:
<221> NAME/KEY: modified_base
<222> LOCATION: (14)..(14)
<223> OTHER INFORMATION: cm (2'-O-methyl cytidine)

<400> SEQUENCE: 166
ccgagccgcu uguccc                                                      16

<210> SEQ ID NO 167
<211> LENGTH: 16
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(16)
<223> OTHER INFORMATION: phosphorothioate internucleotide linkages

<400> SEQUENCE: 167
ccgagccgcu uguccc                                                      16

<210> SEQ ID NO 168
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 168
ccgauauccc aucuucuuuu uccccuuggu                                       30

<210> SEQ ID NO 169
<211> LENGTH: 18
<212> TYPE: RNA
<213> ORGANISM: Artificial Sequence
<220> FEATURE:
<223> OTHER INFORMATION: synthetic oligonucleotide

<400> SEQUENCE: 169
ccgucuguug ugugacag                                                    18

<210> SEQ ID NO 170
<211> LENGTH: 18
<212> TYPE: RNA
<213> ORGANISM: Artificial Sequence
<220> FEATURE:
<223> OTHER INFORMATION: synthetic oligonucleotide

<400> SEQUENCE: 170
ccgucuguug ugugacuc                                                    18

<210> SEQ ID NO 171
<211> LENGTH: 18
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(18)
<223> OTHER INFORMATION: phosphorothioate internucleotide linkages

<400> SEQUENCE: 171
ccgucuguug ugugacuc                                                    18
```

```
<210> SEQ ID NO 172
<211> LENGTH: 18
<212> TYPE: RNA
<213> ORGANISM: Artificial Sequence
<220> FEATURE:
<223> OTHER INFORMATION: synthetic oligonucleotide

<400> SEQUENCE: 172
ccgucuguug uuggacuc                                                  18

<210> SEQ ID NO 173
<211> LENGTH: 10
<212> TYPE: RNA
<213> ORGANISM: Artificial Sequence
<220> FEATURE:
<223> OTHER INFORMATION: synthetic oligonucleotide

<400> SEQUENCE: 173
ccugcuuuug                                                           10

<210> SEQ ID NO 174
<211> LENGTH: 18
<212> TYPE: RNA
<213> ORGANISM: Artificial Sequence
<220> FEATURE:
<223> OTHER INFORMATION: synthetic oligonucleotide

<400> SEQUENCE: 174
cgacucucuc uucaguug                                                  18

<210> SEQ ID NO 175
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 175
cgagccgaau acccc                                                     15

<210> SEQ ID NO 176
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 176
cgagccgcuu acccc                                                     15

<210> SEQ ID NO 177
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 177
cgcaaguuug uuguacgcau uuuuucgcgu                                     30

<210> SEQ ID NO 178
<211> LENGTH: 15
<212> TYPE: RNA
<213> ORGANISM: Artificial Sequence
<220> FEATURE:
<223> OTHER INFORMATION: synthetic oligonucleotide
```

```
<400> SEQUENCE: 178
cgcaccgcuu cugcu                                                    15

<210> SEQ ID NO 179
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 179
cgcauuuuuu cccgu                                                    15

<210> SEQ ID NO 180
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 180
cgcauuuuuu cgcgu                                                    15

<210> SEQ ID NO 181
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 181
cgcuccgcuu cugcu                                                    15

<210> SEQ ID NO 182
<211> LENGTH: 10
<212> TYPE: RNA
<213> ORGANISM: Artificial Sequence
<220> FEATURE:
<223> OTHER INFORMATION: synthetic oligonucleotide

<400> SEQUENCE: 182
cgcuucugcu                                                          10

<210> SEQ ID NO 183
<211> LENGTH: 16
<212> TYPE: RNA
<213> ORGANISM: Artificial Sequence
<220> FEATURE:
<223> OTHER INFORMATION: synthetic oligonucleotide

<400> SEQUENCE: 183
cggcgcgcgc cguuuu                                                   16

<210> SEQ ID NO 184
<211> LENGTH: 16
<212> TYPE: RNA
<213> ORGANISM: Artificial Sequence
<220> FEATURE:
<223> OTHER INFORMATION: synthetic oligonucleotide

<400> SEQUENCE: 184
cggcggccgc cguuuu                                                   16

<210> SEQ ID NO 185
<211> LENGTH: 18
<212> TYPE: RNA
```

```
<213> ORGANISM: Artificial Sequence
<220> FEATURE:
<223> OTHER INFORMATION: synthetic oligonucleotide

<400> SEQUENCE: 185
cggcggccgc cguuuuuu                                                         18

<210> SEQ ID NO 186
<211> LENGTH: 12
<212> TYPE: RNA
<213> ORGANISM: Artificial Sequence
<220> FEATURE:
<223> OTHER INFORMATION: synthetic oligonucleotide

<400> SEQUENCE: 186
cggcuuuugc cg                                                               12

<210> SEQ ID NO 187
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 187
cggugagaga uuaucuaccc ugcuuuugcu                                            30

<210> SEQ ID NO 188
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 188
cggugaguga uuaucuaccc ugcuuuugcu                                            30

<210> SEQ ID NO 189
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 189
cguaucgcuu cugcu                                                            15

<210> SEQ ID NO 190
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 190 cguuuuucu cuugucuggu                                                        20

<210> SEQ ID NO 191
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 191
cuaaaaauuc uucuuucuuu uugugugccc                                            30
```

```
<210> SEQ ID NO 192
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 192
cuaccugcuu ucgcu                                                    15

<210> SEQ ID NO 193
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 193
cuaccugcuu uugcu                                                    15

<210> SEQ ID NO 194
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 194
cuacuacuac uacuacuacu                                               20

<210> SEQ ID NO 195
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 195
cucaucaucu uuuaugauac                                               20

<210> SEQ ID NO 196
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 196
cucaucuuuc aacaucuacc ugcuuuugcu                                    30

<210> SEQ ID NO 197
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 197
cucaucuuuc aauaucuacc ugcuuucgcu                                    30

<210> SEQ ID NO 198
<211> LENGTH: 30
<212> TYPE: RNA
<213> ORGANISM: Artificial Sequence
<220> FEATURE:
<223> OTHER INFORMATION: synthetic oligonucleotide
```

```
<400> SEQUENCE: 198
cucaucuuuc aauaucuacc ugcuuuugcu                               30

<210> SEQ ID NO 199
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 199
cucucucucu cucucucucu                                          20

<210> SEQ ID NO 200
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 200
cucuuaaacu cuugucuggu                                          20

<210> SEQ ID NO 201
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 201
cugagcuuag ucaaguuacu uuucuuauac                               30

<210> SEQ ID NO 202
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 202
cugagcuuag ucaaguuacu uuuuuauac                                30

<210> SEQ ID NO 203
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 203
cugguuguua agcgu                                               15

<210> SEQ ID NO 204
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 204
cugguuuugu uguuaagcgu                                          20

<210> SEQ ID NO 205
<211> LENGTH: 14
<212> TYPE: RNA
```

```
<213> ORGANISM: Artificial Sequence
<220> FEATURE:
<223> OTHER INFORMATION: synthetic oligonucleotide

<400> SEQUENCE: 205 cguugugug acag                                                          14

<210> SEQ ID NO 206
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 206
cuuaaagcuc cgcuucugcu                                                   20

<210> SEQ ID NO 207
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 207
cuuacccaac uuuguuuggu                                                   20

<210> SEQ ID NO 208
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 208
cuuacccagc uuugucuggu                                                   20

<210> SEQ ID NO 209
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 209
cuuacccagc uuuguuuggu                                                   20

<210> SEQ ID NO 210
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 210
cuuagccaac uuugucuggu                                                   20

<210> SEQ ID NO 211
<211> LENGTH: 12
<212> TYPE: RNA
<213> ORGANISM: Artificial Sequence
<220> FEATURE:
<223> OTHER INFORMATION: synthetic oligonucleotide

<400> SEQUENCE: 211
cuucggcuuc gg                                                           12
```

```
<210> SEQ ID NO 212
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 212
cuucucuugu uuggu                                                  15

<210> SEQ ID NO 213
<211> LENGTH: 10
<212> TYPE: RNA
<213> ORGANISM: Artificial Sequence
<220> FEATURE:
<223> OTHER INFORMATION: synthetic oligonucleotide

<400> SEQUENCE: 213
cuugucuggu                                                        10

<210> SEQ ID NO 214
<211> LENGTH: 10
<212> TYPE: RNA
<213> ORGANISM: Artificial Sequence
<220> FEATURE:
<223> OTHER INFORMATION: synthetic oligonucleotide

<400> SEQUENCE: 214
cuuguucggu                                                        10

<210> SEQ ID NO 215
<211> LENGTH: 10
<212> TYPE: RNA
<213> ORGANISM: Artificial Sequence
<220> FEATURE:
<223> OTHER INFORMATION: synthetic oligonucleotide

<400> SEQUENCE: 215
cuuguuuggu                                                        10

<210> SEQ ID NO 216
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 216
cuuuucuucu cugguuuugu uguuaagcgu                                  30

<210> SEQ ID NO 217
<211> LENGTH: 10
<212> TYPE: RNA
<213> ORGANISM: Artificial Sequence
<220> FEATURE:
<223> OTHER INFORMATION: synthetic oligonucleotide

<400> SEQUENCE: 217
cuuuugcuaa                                                        10

<210> SEQ ID NO 218
<211> LENGTH: 15
<212> TYPE: RNA
<213> ORGANISM: Artificial Sequence
<220> FEATURE:
<223> OTHER INFORMATION: synthetic oligonucleotide
```

```
<400> SEQUENCE: 218 cuuuucccc uuggu                                             15

<210> SEQ ID NO 219
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 219 cuuuugugu guccg                                             15

<210> SEQ ID NO 220
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 220
gaaaacgcuc cgcuucugcu                                       20

<210> SEQ ID NO 221
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 221
gaaaauagcc aaucuuagcu                                       20

<210> SEQ ID NO 222
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 222
gaaaaugcuc ugcuucugcu                                       20

<210> SEQ ID NO 223
<211> LENGTH: 26
<212> TYPE: RNA
<213> ORGANISM: Artificial Sequence
<220> FEATURE:
<223> OTHER INFORMATION: synthetic oligonucleotide

<400> SEQUENCE: 223
gacauuucca aucccugcu ucugcu                                 26

<210> SEQ ID NO 224
<211> LENGTH: 26
<212> TYPE: RNA
<213> ORGANISM: Artificial Sequence
<220> FEATURE:
<223> OTHER INFORMATION: synthetic oligonucleotide

<400> SEQUENCE: 224
gacauuucgg aucccugcu ucugcu                                 26

<210> SEQ ID NO 225
<211> LENGTH: 26
<212> TYPE: RNA
```

```
<213> ORGANISM: Artificial Sequence
<220> FEATURE:
<223> OTHER INFORMATION: synthetic oligonucleotide

<400> SEQUENCE: 225
gacuaaacaa augcucugcu ucugcu                                          26

<210> SEQ ID NO 226
<211> LENGTH: 26
<212> TYPE: RNA
<213> ORGANISM: Artificial Sequence
<220> FEATURE:
<223> OTHER INFORMATION: synthetic oligonucleotide

<400> SEQUENCE: 226
gagaugggug cgagagcguc aguauu                                          26

<210> SEQ ID NO 227
<211> LENGTH: 26
<212> TYPE: RNA
<213> ORGANISM: Artificial Sequence
<220> FEATURE:
<223> OTHER INFORMATION: synthetic oligonucleotide

<400> SEQUENCE: 227
gagugauuau cuacccugcu uuugcu                                          26

<210> SEQ ID NO 228
<211> LENGTH: 12
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(12)
<223> OTHER INFORMATION: phosphorothioate internucleotide linkages
<220> FEATURE:
<221> NAME/KEY: modified_base
<222> LOCATION: (2)..(2)
<223> OTHER INFORMATION: am (2'-O-methyl adenosine)
<220> FEATURE:
<221> NAME/KEY: modified_base
<222> LOCATION: (3)..(3)
<223> OTHER INFORMATION: um (2'-O-methyl uridine)

<400> SEQUENCE: 228
gauacuuacc ug                                                         12

<210> SEQ ID NO 229
<211> LENGTH: 12
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(12)
<223> OTHER INFORMATION: phosphorothioate internucleotide linkages
<220> FEATURE:
<221> NAME/KEY: modified_base
<222> LOCATION: (2)..(2)
<223> OTHER INFORMATION: am (2'-O-methyl adenosine)

<400> SEQUENCE: 229
gauacuuacc ug                                                         12

<210> SEQ ID NO 230
<211> LENGTH: 12
<212> TYPE: RNA
```

-continued

<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(12)
<223> OTHER INFORMATION: phosphorothioate internucleotide linkages
<220> FEATURE:
<221> NAME/KEY: modified_base
<222> LOCATION: (3)..(3)
<223> OTHER INFORMATION: um (2'-O-methyl uridine)

<400> SEQUENCE: 230
gauacuuacc ug                                                         12

<210> SEQ ID NO 231
<211> LENGTH: 12
<212> TYPE: RNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: (3)..(3)
<223> OTHER INFORMATION: um (2'-O-methyl uridine)

<400> SEQUENCE: 231
gauacuuacc ug                                                         12

<210> SEQ ID NO 232
<211> LENGTH: 12
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(12)
<223> OTHER INFORMATION: phosphorothioate internucleotide linkages

<400> SEQUENCE: 232
gauacuuacc ug                                                         12

<210> SEQ ID NO 233
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 233
gaucaguacc ugcuuucgcu                                                 20

<210> SEQ ID NO 234
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 234
gaucaguacc ugcuuuugcu                                                 20

<210> SEQ ID NO 235
<211> LENGTH: 12
<212> TYPE: RNA
<213> ORGANISM: Artificial Sequence
<220> FEATURE:
<223> OTHER INFORMATION: synthetic oligonucleotide

```
<400> SEQUENCE: 235
gaucuuuucg gc                                                    12

<210> SEQ ID NO 236
<211> LENGTH: 12
<212> TYPE: RNA
<213> ORGANISM: Artificial Sequence
<220> FEATURE:
<223> OTHER INFORMATION: synthetic oligonucleotide

<400> SEQUENCE: 236
gaucuuuuga uc                                                    12

<210> SEQ ID NO 237
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 237
gauucucugu uuggu                                                 15

<210> SEQ ID NO 238
<211> LENGTH: 26
<212> TYPE: RNA
<213> ORGANISM: Artificial Sequence
<220> FEATURE:
<223> OTHER INFORMATION: synthetic oligonucleotide

<400> SEQUENCE: 238
gauuuccaua aucccugcu ucugcu                                      26

<210> SEQ ID NO 239
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 239
gauuuccccc ugcuuuugcu                                            20

<210> SEQ ID NO 240
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 240
gccaccgagc cgaaggcacc                                            20

<210> SEQ ID NO 241
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 241
gccaccgagc cgaauauacc                                            20

<210> SEQ ID NO 242
<211> LENGTH: 20
<212> TYPE: RNA
```

<213> ORGANISM: Artificial Sequence
<220> FEATURE:
<223> OTHER INFORMATION: synthetic oligonucleotide

<400> SEQUENCE: 242
gcccgacaga agagagacac                                          20

<210> SEQ ID NO 243
<211> LENGTH: 16
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(16)
<223> OTHER INFORMATION: phosphorothioate internucleotide linkages
<220> FEATURE:
<221> NAME/KEY: modified_base
<222> LOCATION: (1)..(1)
<223> OTHER INFORMATION: gm (2'-O-methyl guanosine)

<400> SEQUENCE: 243
gccgaccgau uguacc                                              16

<210> SEQ ID NO 244
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 244
gcccgucugu ugugugacuc                                          20

<210> SEQ ID NO 245
<211> LENGTH: 26
<212> TYPE: RNA
<213> ORGANISM: Artificial Sequence
<220> FEATURE:
<223> OTHER INFORMATION: synthetic oligonucleotide

<400> SEQUENCE: 245
gcgauuucug accgcuuuuu ugucag                                   26

<210> SEQ ID NO 246
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 246
gcguuuuuuu cgcgu                                               15

<210> SEQ ID NO 247
<211> LENGTH: 10
<212> TYPE: RNA
<213> ORGANISM: Artificial Sequence
<220> FEATURE:
<223> OTHER INFORMATION: synthetic oligonucleotide

<400> SEQUENCE: 247
gcuuuugcua                                                     10

<210> SEQ ID NO 248
<211> LENGTH: 12
<212> TYPE: RNA

```
<213> ORGANISM: Artificial Sequence
<220> FEATURE:
<223> OTHER INFORMATION: synthetic oligonucleotide

<400> SEQUENCE: 248
ggacuuuggu cc                                                            12

<210> SEQ ID NO 249
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 249
ggauacauau cucuuaaacu cuugucuggu                                         30

<210> SEQ ID NO 250
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 250
ggauucauuu ugaacuccug cuuuugcuaa                                         30

<210> SEQ ID NO 251
<211> LENGTH: 26
<212> TYPE: RNA
<213> ORGANISM: Artificial Sequence
<220> FEATURE:
<223> OTHER INFORMATION: synthetic oligonucleotide

<400> SEQUENCE: 251
ggcaaaucaa acgcaccgcu ucugcu                                             26

<210> SEQ ID NO 252
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 252
ggcuccgcuu cugcu                                                         15

<210> SEQ ID NO 253
<211> LENGTH: 20
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(20)
<223> OTHER INFORMATION: phosphorothioate internucleotide linkages
<220> FEATURE:
<221> NAME/KEY: modified_base
<222> LOCATION: (15)..(15)
<223> OTHER INFORMATION: am (2'-O-methyl adenosine)

<400> SEQUENCE: 253
ggcuuaucca uugcacuccg                                                    20

<210> SEQ ID NO 254
<211> LENGTH: 21
<212> TYPE: RNA
```

```
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(21)
<223> OTHER INFORMATION: phosphorothioate internucleotide linkages

<400> SEQUENCE: 254
ggcuuaucca uugcacuccg g                                              21

<210> SEQ ID NO 255
<211> LENGTH: 21
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(4)
<223> OTHER INFORMATION: phosphorothioate internucleotide linkages
<220> FEATURE:
<221> NAME/KEY: misc_feature
<222> LOCATION: (15)..(21)
<223> OTHER INFORMATION: phosphorothioate internucleotide linkages

<400> SEQUENCE: 255
ggggaaaaaa aaaagggggg g                                              21

<210> SEQ ID NO 256
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 256 gggggggguug ugu                                                      13

<210> SEQ ID NO 257
<211> LENGTH: 18
<212> TYPE: RNA
<213> ORGANISM: Artificial Sequence
<220> FEATURE:
<223> OTHER INFORMATION: synthetic oligonucleotide

<400> SEQUENCE: 257 gggggggguug uguggggg                                                 18

<210> SEQ ID NO 258
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 258 gggggggugug ugu                                                      13

<210> SEQ ID NO 259
<211> LENGTH: 10
<212> TYPE: RNA
<213> ORGANISM: Artificial Sequence
<220> FEATURE:
<223> OTHER INFORMATION: synthetic oligonucleotide

<400> SEQUENCE: 259
gggguuuuu                                                            10
```

-continued

<210> SEQ ID NO 260
<211> LENGTH: 21
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(21)
<223> OTHER INFORMATION: phosphorothioate internucleotide linkages

<400> SEQUENCE: 260
gggguuauua uuauggggggg g                                            21

<210> SEQ ID NO 261
<211> LENGTH: 21
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(21)
<223> OTHER INFORMATION: phosphorothioate internucleotide linkages

<400> SEQUENCE: 261 ggggguuguug uuggggggg g                                             21

<210> SEQ ID NO 262
<211> LENGTH: 12
<212> TYPE: RNA
<213> ORGANISM: Artificial Sequence
<220> FEATURE:
<223> OTHER INFORMATION: synthetic oligonucleotide

<400> SEQUENCE: 262 ggggguuuucc cc                                                      12

<210> SEQ ID NO 263
<211> LENGTH: 12
<212> TYPE: RNA
<213> ORGANISM: Artificial Sequence
<220> FEATURE:
<223> OTHER INFORMATION: synthetic oligonucleotide

<400> SEQUENCE: 263 ggggguuuugg gg                                                      12

<210> SEQ ID NO 264
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 264 ggggguuuugg ggg                                                     13

<210> SEQ ID NO 265
<211> LENGTH: 21
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(21)
<223> OTHER INFORMATION: phosphorothioate internucleotide linkages -continued

```
<400> SEQUENCE: 265
gggguuuuuu uuuuggggg g                                              21

<210> SEQ ID NO 266
<211> LENGTH: 21
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(4)
<223> OTHER INFORMATION: phosphorothioate internucleotide linkages
<220> FEATURE:
<221> NAME/KEY: misc_feature
<222> LOCATION: (15)..(21)
<223> OTHER INFORMATION: phosphorothioate internucleotide linkages

<400> SEQUENCE: 266
gggguuuuuu uuuuggggg g                                              21

<210> SEQ ID NO 267
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 267
gguugcuuuu auuuucccu gcuuuugcua                                     30

<210> SEQ ID NO 268
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 268
guaccugcuu ucgcu                                                    15

<210> SEQ ID NO 269
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 269
guaccugcuu uugcu                                                    15

<210> SEQ ID NO 270
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 270
guaguaguag uaguaguagu                                               20

<210> SEQ ID NO 271
<211> LENGTH: 10
<212> TYPE: RNA
<213> ORGANISM: Artificial Sequence
<220> FEATURE:
<223> OTHER INFORMATION: synthetic oligonucleotide
```

```
<400> SEQUENCE: 271
guaguguguc                                                          10

<210> SEQ ID NO 272
<211> LENGTH: 12
<212> TYPE: RNA
<213> ORGANISM: Artificial Sequence
<220> FEATURE:
<223> OTHER INFORMATION: synthetic oligonucleotide

<400> SEQUENCE: 272
gucggcguug ac                                                       12

<210> SEQ ID NO 273
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 273
gucgucgucg ucgucgucgu                                               20

<210> SEQ ID NO 274
<211> LENGTH: 12
<212> TYPE: RNA
<213> ORGANISM: Artificial Sequence
<220> FEATURE:
<223> OTHER INFORMATION: synthetic oligonucleotide

<400> SEQUENCE: 274
gucuguugug ug                                                       12

<210> SEQ ID NO 275
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 275
guggauauua gaaaaugcuc ugcuucugcu                                    30

<210> SEQ ID NO 276
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 276
gugguuugcc ugcuuuugcu                                               20

<210> SEQ ID NO 277
<211> LENGTH: 14
<212> TYPE: RNA
<213> ORGANISM: Artificial Sequence
<220> FEATURE:
<223> OTHER INFORMATION: synthetic oligonucleotide

<400> SEQUENCE: 277 guguguguggg gggg                                                    14

<210> SEQ ID NO 278
<211> LENGTH: 20
<212> TYPE: RNA
```

```
<213> ORGANISM: Artificial Sequence
<220> FEATURE:
<223> OTHER INFORMATION: synthetic oligonucleotide

<400> SEQUENCE: 278
gugugugugu gugugugugu                                              20

<210> SEQ ID NO 279
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 279
guugcuuuua uuuuccccug cuuuugcuaa                                   30

<210> SEQ ID NO 280
<211> LENGTH: 18
<212> TYPE: RNA
<213> ORGANISM: Artificial Sequence
<220> FEATURE:
<223> OTHER INFORMATION: synthetic oligonucleotide

<400> SEQUENCE: 280
guugugguug ugguugug                                                18

<210> SEQ ID NO 281
<211> LENGTH: 12
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(12)
<223> OTHER INFORMATION: phosphorothioate internucleotide linkages

<400> SEQUENCE: 281
guuguguaaa aa                                                      12

<210> SEQ ID NO 282
<211> LENGTH: 12
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(12)
<223> OTHER INFORMATION: phosphorothioate internucleotide linkages
<220> FEATURE:
<221> NAME/KEY: modified_base
<222> LOCATION: (8)..(8)
<223> OTHER INFORMATION: 7-deaza guanosine

<400> SEQUENCE: 282 guguguggg gg                                                       12

<210> SEQ ID NO 283
<211> LENGTH: 12
<212> TYPE: RNA
<213> ORGANISM: Artificial Sequence
<220> FEATURE:
<223> OTHER INFORMATION: synthetic oligonucleotide

<400> SEQUENCE: 283 guguguggg gg                                                       12
```

```
<210> SEQ ID NO 284
<211> LENGTH: 11
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(11)
<223> OTHER INFORMATION: phosphorothioate internucleotide linkages

<400> SEQUENCE: 284
guuguguggg g                                                             11

<210> SEQ ID NO 285
<211> LENGTH: 12
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(12)
<223> OTHER INFORMATION: phosphorothioate internucleotide linkages

<400> SEQUENCE: 285
guuguguggg gg                                                            12

<210> SEQ ID NO 286
<211> LENGTH: 12
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(12)
<223> OTHER INFORMATION: phosphorothioate internucleotide linkages

<400> SEQUENCE: 286
guuguguggg gg                                                            12

<210> SEQ ID NO 287
<211> LENGTH: 25
<212> TYPE: RNA
<213> ORGANISM: Artificial Sequence
<220> FEATURE:
<223> OTHER INFORMATION: synthetic oligonucleotide

<400> SEQUENCE: 287
guuguguuuu uacggcgccg ugccg                                              25

<210> SEQ ID NO 288
<211> LENGTH: 14
<212> TYPE: RNA
<213> ORGANISM: Artificial Sequence
<220> FEATURE:
<223> OTHER INFORMATION: synthetic oligonucleotide

<400> SEQUENCE: 288
guuguuuugu uguu                                                          14

<210> SEQ ID NO 289
<211> LENGTH: 11
<212> TYPE: RNA
<213> ORGANISM: Artificial Sequence
<220> FEATURE:
<223> OTHER INFORMATION: synthetic oligonucleotide
```

```
<400> SEQUENCE: 289
guuugugugg g                                                    11

<210> SEQ ID NO 290
<211> LENGTH: 12
<212> TYPE: RNA
<213> ORGANISM: Artificial Sequence
<220> FEATURE:
<223> OTHER INFORMATION: synthetic oligonucleotide

<400> SEQUENCE: 290
guuugugugg gg                                                   12

<210> SEQ ID NO 291
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 291 guuuuuugu uuucuccgu                                             20

<210> SEQ ID NO 292
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 292 guuuuuugu uuuucucgu                                             20

<210> SEQ ID NO 293
<211> LENGTH: 19
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(5)
<223> OTHER INFORMATION: n represents a, c, g, u, t, or i (inosine)
<220> FEATURE:
<221> NAME/KEY: misc_feature
<222> LOCATION: (7)..(7)
<223> OTHER INFORMATION: n represents a, c, g, u, t, or i (inosine)
<220> FEATURE:
<221> NAME/KEY: misc_feature
<222> LOCATION: (9)..(9)
<223> OTHER INFORMATION: n represents a, c, g, u, t, or i (inosine)
<220> FEATURE:
<221> NAME/KEY: misc_feature
<222> LOCATION: (11)..(11)
<223> OTHER INFORMATION: n represents a, c, g, u, t, or i (inosine)
<220> FEATURE:
<221> NAME/KEY: misc_feature
<222> LOCATION: (13)..(19)
<223> OTHER INFORMATION: n represents a, c, g, u, t, or i (inosine)

<400> SEQUENCE: 293
nnnnnanana nannnnnnn                                            19

<210> SEQ ID NO 294
<211> LENGTH: 18
<212> TYPE: RNA
<213> ORGANISM: Artificial Sequence
<220> FEATURE:
<223> OTHER INFORMATION: synthetic oligonucleotide
<220> FEATURE:
```

```
<221> NAME/KEY: misc_feature
<222> LOCATION: (1)..(6)
<223> OTHER INFORMATION: n represents a, c, g, u, t, or i (inosine)
<220> FEATURE:
<221> NAME/KEY: misc_feature
<222> LOCATION: (8)..(8)
<223> OTHER INFORMATION: n represents a, c, g, u, t, or i (inosine)
<220> FEATURE:
<221> NAME/KEY: misc_feature
<222> LOCATION: (10)..(18)
<223> OTHER INFORMATION: n represents a, c, g, u, t, or i (inosine)

<400> SEQUENCE: 294
nnnnnnanan nnnnnnnn                                                 18

<210> SEQ ID NO 295
<211> LENGTH: 18
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(6)
<223> OTHER INFORMATION: n represents a, c, g, u, t, or i (inosine)
<220> FEATURE:
<221> NAME/KEY: misc_feature
<222> LOCATION: (11)..(18)
<223> OTHER INFORMATION: n represents a, c, g, u, t, or i (inosine)

<400> SEQUENCE: 295
nnnnnnuugu nnnnnnnn                                                 18

<210> SEQ ID NO 296
<211> LENGTH: 18
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(6)
<223> OTHER INFORMATION: n represents a, c, g, u, t, or i (inosine)
<220> FEATURE:
<221> NAME/KEY: misc_feature
<222> LOCATION: (11)..(18)
<223> OTHER INFORMATION: n represents a, c, g, u, t, or i (inosine)

<400> SEQUENCE: 296
nnnnnnuuuu nnnnnnnn                                                 18

<210> SEQ ID NO 297
<211> LENGTH: 20
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: n represents a, c, g, u, t, or i (inosine)
<220> FEATURE:
<221> NAME/KEY: misc_feature
<222> LOCATION: (4)..(4)
<223> OTHER INFORMATION: n represents a, c, g, u, t, or i (inosine)
<220> FEATURE:
<221> NAME/KEY: misc_feature
<222> LOCATION: (7)..(7)
<223> OTHER INFORMATION: n represents a, c, g, u, t, or i (inosine)
<220> FEATURE:
<221> NAME/KEY: misc_feature
<222> LOCATION: (10)..(10)
<223> OTHER INFORMATION: n represents a, c, g, u, t, or i (inosine)
<220> FEATURE:
```

```
<221> NAME/KEY: misc_feature
<222> LOCATION: (13)..(13)
<223> OTHER INFORMATION: n represents a, c, g, u, t, or i (inosine)
<220> FEATURE:
<221> NAME/KEY: misc_feature
<222> LOCATION: (16)..(16)
<223> OTHER INFORMATION: n represents a, c, g, u, t, or i (inosine)
<220> FEATURE:
<221> NAME/KEY: misc_feature
<222> LOCATION: (19)..(19)
<223> OTHER INFORMATION: n represents a, c, g, u, t, or i (inosine)

<400> SEQUENCE: 297
nuanuanuan uanuanuanu                                            20

<210> SEQ ID NO 298
<211> LENGTH: 19
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (10)..(16)
<223> OTHER INFORMATION: ribonucleotides

<400> SEQUENCE: 298
tcgtcgtttg uuguguaat                                             19

<210> SEQ ID NO 299
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 299
uaaaaaaccu uuuuucuuuu uguguguccg                                 30

<210> SEQ ID NO 300
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 300
uaaaaauucu ucuuucuuuu uguguguccg                                 30

<210> SEQ ID NO 301
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 301
uaacuuaauu uauacgcguu uuuuucgcgu                                 30

<210> SEQ ID NO 302
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 302
uaagaaugcu auugguuugu uuuucuucgu                                 30
```

<210> SEQ ID NO 303
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 303
uaaugauaau aaugguuugu uugucuucgu                                    30

<210> SEQ ID NO 304
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 304
uaaugguaau aaugguuugu uugucuucgu                                    30

<210> SEQ ID NO 305
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 305
uaauguuauc aaugguuuau uugucuucgu                                    30

<210> SEQ ID NO 306
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 306
uaauuauauu aaugguuugu uugucuucgu                                    30

<210> SEQ ID NO 307
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 307
uaauuguaag aaugguuuuu uugucuucgu                                    30

<210> SEQ ID NO 308
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 308
uaauuguaau aaugguuuuu uugucuucgu                                    30

<210> SEQ ID NO 309
<211> LENGTH: 15
<212> TYPE: RNA
<213> ORGANISM: Artificial Sequence
<220> FEATURE:
<223> OTHER INFORMATION: synthetic oligonucleotide -continued

```
<400> SEQUENCE: 309
uacccugcuu uugcu                                                15

<210> SEQ ID NO 310
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 310
uagaacgauc cuuacccagc uuugucuggu                                30

<210> SEQ ID NO 311
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 311
uagaccgauc cuuacccaac uuuguuuggu                                30

<210> SEQ ID NO 312
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 312
uagccaaucu uagcu                                                15

<210> SEQ ID NO 313
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 313
uaguacgcau uuuuucgcgu                                           20

<210> SEQ ID NO 314
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 314
uauaccuauc cuuacccagc uuuguuuggu                                30

<210> SEQ ID NO 315
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 315
uauacgcguu uuuuucgcgu                                           20

<210> SEQ ID NO 316
<211> LENGTH: 30
<212> TYPE: RNA
```

```
<213> ORGANISM: Artificial Sequence
<220> FEATURE:
<223> OTHER INFORMATION: synthetic oligonucleotide

<400> SEQUENCE: 316
uauauucauc uuaaaggcuc cgcuucugcu                                    30

<210> SEQ ID NO 317
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 317
uauccaucuu gaaaauagcc aaucuuagcu                                    30

<210> SEQ ID NO 318
<211> LENGTH: 26
<212> TYPE: RNA
<213> ORGANISM: Artificial Sequence
<220> FEATURE:
<223> OTHER INFORMATION: synthetic oligonucleotide

<400> SEQUENCE: 318
uaugucuuug ucacccugcu uuugcu                                        26

<210> SEQ ID NO 319
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 319
uauuuucccc ugcuuuugcu                                               20

<210> SEQ ID NO 320
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 320
ucaaacgcac cgcuucugcu                                               20

<210> SEQ ID NO 321
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 321
ucaaacguau cgcuucugcu                                               20

<210> SEQ ID NO 322
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 322
ucaaguuacu uuucuuauac                                               20
```

-continued

```
<210> SEQ ID NO 323
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 323 ucaaguacu uuuuuauac                                                   20

<210> SEQ ID NO 324
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 324
ucacagauuc ucuguuuggu                                                 20

<210> SEQ ID NO 325
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 325
ucaccgauuc ucuguuuggu                                                 20

<210> SEQ ID NO 326
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 326
ucacggauuc ucuguuuggu                                                 20

<210> SEQ ID NO 327
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 327 ucauuuccc cuugg                                                       15

<210> SEQ ID NO 328
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 328
uccccugcuu uugcu                                                      15

<210> SEQ ID NO 329
<211> LENGTH: 10
<212> TYPE: RNA
<213> ORGANISM: Artificial Sequence
<220> FEATURE:
<223> OTHER INFORMATION: synthetic oligonucleotide
```

```
<400> SEQUENCE: 329
uccccuuggu                                                          10

<210> SEQ ID NO 330
<211> LENGTH: 26
<212> TYPE: RNA
<213> ORGANISM: Artificial Sequence
<220> FEATURE:
<223> OTHER INFORMATION: synthetic oligonucleotide

<400> SEQUENCE: 330
uccgcaaugg acgaaagucu gacgga                                        26

<210> SEQ ID NO 331
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 331
uccugcuuuu gcuaa                                                    15

<210> SEQ ID NO 332
<211> LENGTH: 14
<212> TYPE: RNA
<213> ORGANISM: Artificial Sequence
<220> FEATURE:
<223> OTHER INFORMATION: synthetic oligonucleotide

<400> SEQUENCE: 332
ucgacgucga uuuu                                                     14

<210> SEQ ID NO 333
<211> LENGTH: 26
<212> TYPE: RNA
<213> ORGANISM: Artificial Sequence
<220> FEATURE:
<223> OTHER INFORMATION: synthetic oligonucleotide

<400> SEQUENCE: 333
ucgacgucga uuuucggcgc gcgccg                                        26

<210> SEQ ID NO 334
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 334
ucuccugcuu uugcu                                                    15

<210> SEQ ID NO 335
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 335
ucucuuguuu uugugugucu                                               20

<210> SEQ ID NO 336
<211> LENGTH: 10
<212> TYPE: RNA
```

```
<213> ORGANISM: Artificial Sequence
<220> FEATURE:
<223> OTHER INFORMATION: synthetic oligonucleotide

<400> SEQUENCE: 336
ucuguuuggu                                                          10

<210> SEQ ID NO 337
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 337
ucuuccaagu aucaucaucu uuuuugauac                                    30

<210> SEQ ID NO 338
<211> LENGTH: 26
<212> TYPE: RNA
<213> ORGANISM: Artificial Sequence
<220> FEATURE:
<223> OTHER INFORMATION: synthetic oligonucleotide

<400> SEQUENCE: 338
ucuuucaaua ucuaccugcu uucgcu                                        26

<210> SEQ ID NO 339
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 339
ucuuucuuuu uguguguccg                                               20

<210> SEQ ID NO 340
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 340
ucuuuuugug ugccc                                                    15

<210> SEQ ID NO 341
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 341
ugaacuccug cuuuugcuaa                                               20

<210> SEQ ID NO 342
<211> LENGTH: 26
<212> TYPE: RNA
<213> ORGANISM: Artificial Sequence
<220> FEATURE:
<223> OTHER INFORMATION: synthetic oligonucleotide

<400> SEQUENCE: 342
ugaaggaaca ucugcuuguu uuugcu                                        26
```

-continued

<210> SEQ ID NO 343
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 343
ugaccugcuu ucgcu                                                    15

<210> SEQ ID NO 344
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 344
ugaccugcuu uucgu                                                    15

<210> SEQ ID NO 345
<211> LENGTH: 26
<212> TYPE: RNA
<213> ORGANISM: Artificial Sequence
<220> FEATURE:
<223> OTHER INFORMATION: synthetic oligonucleotide

<400> SEQUENCE: 345
ugagaagaaa augcugugcu ucugcu                                        26

<210> SEQ ID NO 346
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 346
ugauuuuuau augguuuuuu uguuaagcgu                                    30

<210> SEQ ID NO 347
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 347
ugcaaguuug uaguacgcau uuuucgcgu                                     30

<210> SEQ ID NO 348
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 348
ugcaaguuug uuguacgcau uuuucccgu                                     30

<210> SEQ ID NO 349
<211> LENGTH: 15
<212> TYPE: RNA
<213> ORGANISM: Artificial Sequence
<220> FEATURE:
<223> OTHER INFORMATION: synthetic oligonucleotide

```
<400> SEQUENCE: 349
ugcgcugcuu ucgcu                                                15

<210> SEQ ID NO 350
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 350
ugcucugcuu cugcu                                                15

<210> SEQ ID NO 351
<211> LENGTH: 10
<212> TYPE: RNA
<213> ORGANISM: Artificial Sequence
<220> FEATURE:
<223> OTHER INFORMATION: synthetic oligonucleotide

<400> SEQUENCE: 351
ugcuucugcu                                                      10

<210> SEQ ID NO 352
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 352
ugcuucuucu uugguuuugu uguuaagcgu                                30

<210> SEQ ID NO 353
<211> LENGTH: 10
<212> TYPE: RNA
<213> ORGANISM: Artificial Sequence
<220> FEATURE:
<223> OTHER INFORMATION: synthetic oligonucleotide

<400> SEQUENCE: 353
ugcuuucgcu                                                      10

<210> SEQ ID NO 354
<211> LENGTH: 10
<212> TYPE: RNA
<213> ORGANISM: Artificial Sequence
<220> FEATURE:
<223> OTHER INFORMATION: synthetic oligonucleotide

<400> SEQUENCE: 354
ugcuuuucgu                                                      10

<210> SEQ ID NO 355
<211> LENGTH: 10
<212> TYPE: RNA
<213> ORGANISM: Artificial Sequence
<220> FEATURE:
<223> OTHER INFORMATION: synthetic oligonucleotide

<400> SEQUENCE: 355
ugcuuuugcu                                                      10

<210> SEQ ID NO 356
<211> LENGTH: 12
<212> TYPE: RNA
```

```
<213> ORGANISM: Artificial Sequence
<220> FEATURE:
<223> OTHER INFORMATION: synthetic oligonucleotide

<400> SEQUENCE: 356
uggugguugu ug                                                          12

<210> SEQ ID NO 357
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 357
ugguugauuu aauuucccc ugcuuugcu                                         30

<210> SEQ ID NO 358
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 358
ugguugauuu gauuucccc ugcuuugcu                                         30

<210> SEQ ID NO 359
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 359
ugguugauuu uauuucccc ugcuuugcu                                         30

<210> SEQ ID NO 360
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 360
ugguugcuuu uauuucccc ugcuuugcu                                         30

<210> SEQ ID NO 361
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 361
ugguugguuu uauuucccc ugcuuugcu                                         30

<210> SEQ ID NO 362
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 362
ugguuguauu uauuucccc ugcuuugcu                                         30
```

```
<210> SEQ ID NO 363
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 363
ugguuguuuu uauuucccc ugcuuugcu                                30

<210> SEQ ID NO 364
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 364
uguaacauaa cucaucaucu uuuaugauac                              30

<210> SEQ ID NO 365
<211> LENGTH: 26
<212> TYPE: RNA
<213> ORGANISM: Artificial Sequence
<220> FEATURE:
<223> OTHER INFORMATION: synthetic oligonucleotide

<400> SEQUENCE: 365
ugucauguca agugcuuguu uuugcu                                  26

<210> SEQ ID NO 366
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 366
ugugucuucu uugaucuggu uguuaagcgu                              30

<210> SEQ ID NO 367
<211> LENGTH: 10
<212> TYPE: RNA
<213> ORGANISM: Artificial Sequence
<220> FEATURE:
<223> OTHER INFORMATION: synthetic oligonucleotide

<400> SEQUENCE: 367
uguguguccg                                                    10

<210> SEQ ID NO 368
<211> LENGTH: 10
<212> TYPE: RNA
<213> ORGANISM: Artificial Sequence
<220> FEATURE:
<223> OTHER INFORMATION: synthetic oligonucleotide

<400> SEQUENCE: 368
uguuaagcgu                                                    10

<210> SEQ ID NO 369
<211> LENGTH: 21
<212> TYPE: RNA
<213> ORGANISM: Artificial Sequence
<220> FEATURE:
<223> OTHER INFORMATION: synthetic oligonucleotide
```

<400> SEQUENCE: 369
uguucuucug gaaguccagu u  21

<210> SEQ ID NO 370
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 370 uguucuucu cuuguuggu  20

<210> SEQ ID NO 371
<211> LENGTH: 26
<212> TYPE: RNA
<213> ORGANISM: Artificial Sequence
<220> FEATURE:
<223> OTHER INFORMATION: synthetic oligonucleotide

<400> SEQUENCE: 371 uguuuuauu uccccugcu uuugcu  26

<210> SEQ ID NO 372
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 372
uguuuuugug ugucu  15

<210> SEQ ID NO 373
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 373
uguuuuuucu cuuguuggu  20

<210> SEQ ID NO 374
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 374
uguuuuuucu uugaucuggu uguuaagcgu  30

<210> SEQ ID NO 375
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 375
uuaaaggcuc cgcuucugcu  20

<210> SEQ ID NO 376
<211> LENGTH: 20
<212> TYPE: RNA

<213> ORGANISM: Artificial Sequence
<220> FEATURE:
<223> OTHER INFORMATION: synthetic oligonucleotide

<400> SEQUENCE: 376
uuacagauuc ucuguuuggu                                           20

<210> SEQ ID NO 377
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 377
uuaccaagca aguuucuucu cuuguuuggu                                30

<210> SEQ ID NO 378
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 378
uuacggauuc ucuguuuggu                                           20

<210> SEQ ID NO 379
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 379
uuacuuuucu uauac                                                15

<210> SEQ ID NO 380
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 380
uuacuuuuuu uauac                                                15

<210> SEQ ID NO 381
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 381
uuauauucau cuuaaagcuc cgcuucugcu                                30

<210> SEQ ID NO 382
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 382
uuaucaaccc ugcuuuugcu                                           20

```
<210> SEQ ID NO 383
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 383
uuaucguaac ucaccgauuc ucuguuuggu                                    30

<210> SEQ ID NO 384
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 384
uuaucguaac ucacggauuc ucuguuuggu                                    30

<210> SEQ ID NO 385
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 385
uuaucguaac uuacggauuc ucuguuuggu                                    30

<210> SEQ ID NO 386
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 386
uuaucguacc ucacagauuc ucuguuuggu                                    30

<210> SEQ ID NO 387
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 387
uuaucguacc uuacagauuc ucuguuuggu                                    30

<210> SEQ ID NO 388
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 388
uuaucuaccc ugcuuuugcu                                               20

<210> SEQ ID NO 389
<211> LENGTH: 30
<212> TYPE: RNA
<213> ORGANISM: Artificial Sequence
<220> FEATURE:
<223> OTHER INFORMATION: synthetic oligonucleotide
```

```
<400> SEQUENCE: 389
uuauggcaaa ucaaacgcac cgcuucugcu                              30

<210> SEQ ID NO 390
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 390
uuauggcaaa ucaaacguau cgcuucugcu                              30

<210> SEQ ID NO 391
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 391
uuauuaaccc ugcuuuugcu                                         20

<210> SEQ ID NO 392
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 392
uuauuauuau uauuauuauu                                         20

<210> SEQ ID NO 393
<211> LENGTH: 26
<212> TYPE: RNA
<213> ORGANISM: Artificial Sequence
<220> FEATURE:
<223> OTHER INFORMATION: synthetic oligonucleotide

<400> SEQUENCE: 393
uucaucuuaa aggcuccgcu ucugcu                                  26

<210> SEQ ID NO 394
<211> LENGTH: 26
<212> TYPE: RNA
<213> ORGANISM: Artificial Sequence
<220> FEATURE:
<223> OTHER INFORMATION: synthetic oligonucleotide

<400> SEQUENCE: 394
uucauuuugu aucccugcu uuugcu                                   26

<210> SEQ ID NO 395
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 395
uuccauucug aaucaguacc ugcuuuugcu                              30

<210> SEQ ID NO 396
<211> LENGTH: 30
<212> TYPE: RNA
```

-continued

<213> ORGANISM: Artificial Sequence
<220> FEATURE:
<223> OTHER INFORMATION: synthetic oligonucleotide

<400> SEQUENCE: 396
uuccauuucg aaucaguacc ugcuuucgcu                                    30

<210> SEQ ID NO 397
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 397
uuccauuucg gaucaguacc ugcuuuugcu                                    30

<210> SEQ ID NO 398
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 398
uuccauuuug aaucaguacc ugcuuucgcu                                    30

<210> SEQ ID NO 399
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 399
uuccauuuug gaucaguacc ugcuuucgcu                                    30

<210> SEQ ID NO 400
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 400
uuccauuuug gaucaguacc ugcuuuugcu                                    30

<210> SEQ ID NO 401
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 401
uucccaagca agucucuucu cuuguuggu                                     30

<210> SEQ ID NO 402
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 402
uucccagaca aguuucuucu cuuguuggu                                     30

```
<210> SEQ ID NO 403
<211> LENGTH: 10
<212> TYPE: RNA
<213> ORGANISM: Artificial Sequence
<220> FEATURE:
<223> OTHER INFORMATION: synthetic oligonucleotide

<400> SEQUENCE: 403
uuccccuugg                                                              10

<210> SEQ ID NO 404
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 404
uuccccuugu ucggu                                                        15

<210> SEQ ID NO 405
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 405 uucccucuugu uuggu                                                       15

<210> SEQ ID NO 406
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 406
uucgcugcuu ucgcu                                                        15

<210> SEQ ID NO 407
<211> LENGTH: 26
<212> TYPE: RNA
<213> ORGANISM: Artificial Sequence
<220> FEATURE:
<223> OTHER INFORMATION: synthetic oligonucleotide

<400> SEQUENCE: 407
uucuaagaau augcucugcu ucugcu                                            26

<210> SEQ ID NO 408
<211> LENGTH: 26
<212> TYPE: RNA
<213> ORGANISM: Artificial Sequence
<220> FEATURE:
<223> OTHER INFORMATION: synthetic oligonucleotide

<400> SEQUENCE: 408
uucucugucc aucgcuuguu uuugcu                                            26

<210> SEQ ID NO 409
<211> LENGTH: 20
<212> TYPE: RNA
<213> ORGANISM: Artificial Sequence
<220> FEATURE:
<223> OTHER INFORMATION: synthetic oligonucleotide
```

<400> SEQUENCE: 409
uucuuucuuu uugugugccc                                            20

<210> SEQ ID NO 410
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 410
uugaacuauc cuuacccaac uuuguuuggu                                 30

<210> SEQ ID NO 411
<211> LENGTH: 26
<212> TYPE: RNA
<213> ORGANISM: Artificial Sequence
<220> FEATURE:
<223> OTHER INFORMATION: synthetic oligonucleotide

<400> SEQUENCE: 411
uugaauauaa uugaccugcu uucgcu                                     26

<210> SEQ ID NO 412
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 412
uugaucuauc cuuacccaac uuuguuuggu                                 30

<210> SEQ ID NO 413
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 413
uugaucuggu uguuaagcgu                                            20

<210> SEQ ID NO 414
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 414
uugccugcuu ucgcu                                                 15

<210> SEQ ID NO 415
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 415
uugccugcuu uugcu                                                 15

<210> SEQ ID NO 416
<211> LENGTH: 30
<212> TYPE: RNA

<213> ORGANISM: Artificial Sequence
<220> FEATURE:
<223> OTHER INFORMATION: synthetic oligonucleotide

<400> SEQUENCE: 416
uuggauucau uuuaaucucc ugcuuuugcu                              30

<210> SEQ ID NO 417
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 417
uugguuuugu uguuaagcgu                                         20

<210> SEQ ID NO 418
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 418
uuguacgcau uuuuucccgu                                         20

<210> SEQ ID NO 419
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 419
uuguacgcau uuuucgcgu                                          20

<210> SEQ ID NO 420
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 420
uuguauuagg aauggguuuuu uugucuucgu                             30

<210> SEQ ID NO 421
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 421
uuguauucau uuuaaacccc ugcuuuugcu                              30

<210> SEQ ID NO 422
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 422
uuguauucau uuuaaacucc ugcuuuugcu                              30

```
<210> SEQ ID NO 423
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 423
uugucauaua auugguuuuu uugucuucgu                                        30

<210> SEQ ID NO 424
<211> LENGTH: 10
<212> TYPE: RNA
<213> ORGANISM: Artificial Sequence
<220> FEATURE:
<223> OTHER INFORMATION: synthetic oligonucleotide

<400> SEQUENCE: 424
uugucuucgu                                                              10

<210> SEQ ID NO 425
<211> LENGTH: 10
<212> TYPE: RNA
<213> ORGANISM: Artificial Sequence
<220> FEATURE:
<223> OTHER INFORMATION: synthetic oligonucleotide

<400> SEQUENCE: 425
uuguggguca                                                              10

<210> SEQ ID NO 426
<211> LENGTH: 10
<212> TYPE: RNA
<213> ORGANISM: Artificial Sequence
<220> FEATURE:
<223> OTHER INFORMATION: synthetic oligonucleotide

<400> SEQUENCE: 426
uugugugccc                                                              10

<210> SEQ ID NO 427
<211> LENGTH: 10
<212> TYPE: RNA
<213> ORGANISM: Artificial Sequence
<220> FEATURE:
<223> OTHER INFORMATION: synthetic oligonucleotide

<400> SEQUENCE: 427
uugugugucu                                                              10

<210> SEQ ID NO 428
<211> LENGTH: 26
<212> TYPE: RNA
<213> ORGANISM: Artificial Sequence
<220> FEATURE:
<223> OTHER INFORMATION: synthetic oligonucleotide

<400> SEQUENCE: 428
uuguguuugg agcgccuguu uuugcu                                            26

<210> SEQ ID NO 429
<211> LENGTH: 20
<212> TYPE: RNA
<213> ORGANISM: Artificial Sequence
<220> FEATURE:
<223> OTHER INFORMATION: synthetic oligonucleotide
```

```
<400> SEQUENCE: 429
uuguuguugu uguuguuguu                                              20

<210> SEQ ID NO 430
<211> LENGTH: 24
<212> TYPE: RNA
<213> ORGANISM: Artificial Sequence
<220> FEATURE:
<223> OTHER INFORMATION: synthetic oligonucleotide

<400> SEQUENCE: 430
uuguuguuuu guuguuuugu uguu                                         24

<210> SEQ ID NO 431
<211> LENGTH: 22
<212> TYPE: RNA
<213> ORGANISM: Artificial Sequence
<220> FEATURE:
<223> OTHER INFORMATION: synthetic oligonucleotide

<400> SEQUENCE: 431
uuguuguuuu uggugguugu ug                                           22

<210> SEQ ID NO 432
<211> LENGTH: 26
<212> TYPE: RNA
<213> ORGANISM: Artificial Sequence
<220> FEATURE:
<223> OTHER INFORMATION: synthetic oligonucleotide

<400> SEQUENCE: 432
uuguuuagaa auccccugcu ucugcu                                       26

<210> SEQ ID NO 433
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 433
uuguuuuugu guguc                                                   15

<210> SEQ ID NO 434
<211> LENGTH: 20
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (3)..(3)
<223> OTHER INFORMATION: n represents a, c, g, u, t, or i (inosine)
<220> FEATURE:
<221> NAME/KEY: misc_feature
<222> LOCATION: (6)..(6)
<223> OTHER INFORMATION: n represents a, c, g, u, t, or i (inosine)
<220> FEATURE:
<221> NAME/KEY: misc_feature
<222> LOCATION: (9)..(9)
<223> OTHER INFORMATION: n represents a, c, g, u, t, or i (inosine)
<220> FEATURE:
<221> NAME/KEY: misc_feature
<222> LOCATION: (12)..(12)
<223> OTHER INFORMATION: n represents a, c, g, u, t, or i (inosine)
<220> FEATURE:
<221> NAME/KEY: misc_feature
<222> LOCATION: (15)..(15)
<223> OTHER INFORMATION: n represents a, c, g, u, t, or i (inosine)
<220> FEATURE:
```

```
<221> NAME/KEY: misc_feature
<222> LOCATION: (18)..(18)
<223> OTHER INFORMATION: n represents a, c, g, u, t, or i (inosine)

<400> SEQUENCE: 434
uunuunuunu unuunuunuu                                              20

<210> SEQ ID NO 435
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 435
uuuaaacccc ugcuuuugcu                                              20

<210> SEQ ID NO 436
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 436
uuuaaacucc ugcuuuugcu                                              20

<210> SEQ ID NO 437
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 437
uuuaacuauc cuuagccaac uuugucuggu                                   30

<210> SEQ ID NO 438
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 438
uuuaaucucc ugcuuuugcu                                              20

<210> SEQ ID NO 439
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 439
uuuaucuauc cauagccaac uuuuucuggu                                   30

<210> SEQ ID NO 440
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 440
uuuaucuauc cuuagccaac uuugucuggu                                   30
```

```
<210> SEQ ID NO 441
<211> LENGTH: 10
<212> TYPE: RNA
<213> ORGANISM: Artificial Sequence
<220> FEATURE:
<223> OTHER INFORMATION: synthetic oligonucleotide

<400> SEQUENCE: 441
uuuaugauac                                                           10

<210> SEQ ID NO 442
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 442
uuuauuuauu uauuuauuua                                                20

<210> SEQ ID NO 443
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 443
uuuauuuguc uucgu                                                     15

<210> SEQ ID NO 444
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 444
uuuccaaaca agucucuucu cuuguuuggu                                     30

<210> SEQ ID NO 445
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 445
uuucucuugu cuggu                                                     15

<210> SEQ ID NO 446
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 446
uuucucuugu uuggu                                                     15

<210> SEQ ID NO 447
<211> LENGTH: 10
<212> TYPE: RNA
<213> ORGANISM: Artificial Sequence
<220> FEATURE:
<223> OTHER INFORMATION: synthetic oligonucleotide
```

```
<400> SEQUENCE: 447
uucuuauac                                                            10

<210> SEQ ID NO 448
<211> LENGTH: 26
<212> TYPE: RNA
<213> ORGANISM: Artificial Sequence
<220> FEATURE:
<223> OTHER INFORMATION: synthetic oligonucleotide

<400> SEQUENCE: 448
uuuggaaaag uaccccugcu ucugcu                                         26

<210> SEQ ID NO 449
<211> LENGTH: 10
<212> TYPE: RNA
<213> ORGANISM: Artificial Sequence
<220> FEATURE:
<223> OTHER INFORMATION: synthetic oligonucleotide

<400> SEQUENCE: 449
uuugucuggu                                                           10

<210> SEQ ID NO 450
<211> LENGTH: 10
<212> TYPE: RNA
<213> ORGANISM: Artificial Sequence
<220> FEATURE:
<223> OTHER INFORMATION: synthetic oligonucleotide

<400> SEQUENCE: 450
uuuguguguc                                                           10

<210> SEQ ID NO 451
<211> LENGTH: 30
<212> TYPE: RNA
<213> ORGANISM: Artificial Sequence
<220> FEATURE:
<223> OTHER INFORMATION: synthetic oligonucleotide

<400> SEQUENCE: 451
uuuguguguc ucucuuguuu uugugugucu                                     30

<210> SEQ ID NO 452
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 452
uuuguuguua agcgu                                                     15

<210> SEQ ID NO 453
<211> LENGTH: 10
<212> TYPE: RNA
<213> ORGANISM: Artificial Sequence
<220> FEATURE:
<223> OTHER INFORMATION: synthetic oligonucleotide

<400> SEQUENCE: 453
uuuguuuggu                                                           10

<210> SEQ ID NO 454
<211> LENGTH: 15
<212> TYPE: RNA
```

```
<213> ORGANISM: Artificial Sequence
<220> FEATURE:
<223> OTHER INFORMATION: synthetic oligonucleotide

<400> SEQUENCE: 454
uuuguuuguc uucgu                                                    15

<210> SEQ ID NO 455
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 455
uuuguuuguu uguuuguuug                                               20

<210> SEQ ID NO 456
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 456
uuuguuuuuc uccgu                                                    15

<210> SEQ ID NO 457
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 457
uuuguuuuuc uucgu                                                    15

<210> SEQ ID NO 458
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 458
uuuguuuuuu cucgu                                                    15

<210> SEQ ID NO 459
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 459
uuuuauuuua uuuuauuuua                                               20

<210> SEQ ID NO 460
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 460 uuuccccug cuuuugcuaa                                                20
```

-continued

```
<210> SEQ ID NO 461
<211> LENGTH: 16
<212> TYPE: RNA
<213> ORGANISM: Artificial Sequence
<220> FEATURE:
<223> OTHER INFORMATION: synthetic oligonucleotide

<400> SEQUENCE: 461
uuuucggcgc gcgccg                                                    16

<210> SEQ ID NO 462
<211> LENGTH: 16
<212> TYPE: RNA
<213> ORGANISM: Artificial Sequence
<220> FEATURE:
<223> OTHER INFORMATION: synthetic oligonucleotide

<400> SEQUENCE: 462
uuuucggcgg ccgccg                                                    16

<210> SEQ ID NO 463
<211> LENGTH: 10
<212> TYPE: RNA
<213> ORGANISM: Artificial Sequence
<220> FEATURE:
<223> OTHER INFORMATION: synthetic oligonucleotide

<400> SEQUENCE: 463
uuuucuccgu                                                           10

<210> SEQ ID NO 464
<211> LENGTH: 10
<212> TYPE: RNA
<213> ORGANISM: Artificial Sequence
<220> FEATURE:
<223> OTHER INFORMATION: synthetic oligonucleotide

<400> SEQUENCE: 464
uuuucuucgu                                                           10

<210> SEQ ID NO 465
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 465
uuuuguuuug uuuuguuuug                                                20

<210> SEQ ID NO 466
<211> LENGTH: 10
<212> TYPE: RNA
<213> ORGANISM: Artificial Sequence
<220> FEATURE:
<223> OTHER INFORMATION: synthetic oligonucleotide

<400> SEQUENCE: 466
uuuuucccgu                                                           10

<210> SEQ ID NO 467
<211> LENGTH: 10
<212> TYPE: RNA
<213> ORGANISM: Artificial Sequence
<220> FEATURE:
<223> OTHER INFORMATION: synthetic oligonucleotide
```

```
<400> SEQUENCE: 467
uuuuucgcgu                                                           10

<210> SEQ ID NO 468
<211> LENGTH: 10
<212> TYPE: RNA
<213> ORGANISM: Artificial Sequence
<220> FEATURE:
<223> OTHER INFORMATION: synthetic oligonucleotide

<400> SEQUENCE: 468
uuuuucucgu                                                           10

<210> SEQ ID NO 469
<211> LENGTH: 10
<212> TYPE: RNA
<213> ORGANISM: Artificial Sequence
<220> FEATURE:
<223> OTHER INFORMATION: synthetic oligonucleotide

<400> SEQUENCE: 469
uuuuucuggu                                                           10

<210> SEQ ID NO 470
<211> LENGTH: 20
<212> TYPE: RNA
<213> ORGANISM: Artificial Sequence
<220> FEATURE:
<223> OTHER INFORMATION: synthetic oligonucleotide

<400> SEQUENCE: 470
uuuuucuuuu uguguguccg                                                20

<210> SEQ ID NO 471
<211> LENGTH: 10
<212> TYPE: RNA
<213> ORGANISM: Artificial Sequence
<220> FEATURE:
<223> OTHER INFORMATION: synthetic oligonucleotide

<400> SEQUENCE: 471
uuuuugauac                                                           10

<210> SEQ ID NO 472
<211> LENGTH: 10
<212> TYPE: RNA
<213> ORGANISM: Artificial Sequence
<220> FEATURE:
<223> OTHER INFORMATION: synthetic oligonucleotide

<400> SEQUENCE: 472
uuuuuggggg                                                           10

<210> SEQ ID NO 473
<211> LENGTH: 10
<212> TYPE: RNA
<213> ORGANISM: Artificial Sequence
<220> FEATURE:
<223> OTHER INFORMATION: synthetic oligonucleotide

<400> SEQUENCE: 473
uuuuuuauac                                                           10

<210> SEQ ID NO 474
<211> LENGTH: 18
<212> TYPE: RNA
```

```
<213> ORGANISM: Artificial Sequence
<220> FEATURE:
<223> OTHER INFORMATION: synthetic oligonucleotide

<400> SEQUENCE: 474
uuuuuucggc ggccgccg                                                    18

<210> SEQ ID NO 475
<211> LENGTH: 11
<212> TYPE: RNA
<213> ORGANISM: Artificial Sequence
<220> FEATURE:
<223> OTHER INFORMATION: synthetic oligonucleotide

<400> SEQUENCE: 475
uuuuuugggg g                                                           11

<210> SEQ ID NO 476
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 476
uuuuuuguua agcgu                                                       15

<210> SEQ ID NO 477
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 477
uuuuuuuguc uucgu                                                       15

<210> SEQ ID NO 478
<211> LENGTH: 10
<212> TYPE: RNA
<213> ORGANISM: Artificial Sequence
<220> FEATURE:
<223> OTHER INFORMATION: synthetic oligonucleotide

<400> SEQUENCE: 478
uuuuuuuuuu                                                             10

<210> SEQ ID NO 479
<211> LENGTH: 30
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (17)..(17)
<223> OTHER INFORMATION: n represents thymine ribonucleotide
<220> FEATURE:
<221> NAME/KEY: misc_feature
<222> LOCATION: (19)..(19)
<223> OTHER INFORMATION: n represents thymine ribonucleotide
<220> FEATURE:
<221> NAME/KEY: misc_feature
<222> LOCATION: (23)..(24)
<223> OTHER INFORMATION: n represents thymine ribonucleotide
<220> FEATURE:
<221> NAME/KEY: misc_feature
<222> LOCATION: (28)..(29)
<223> OTHER INFORMATION: n represents thymine ribonucleotide
```

-continued

```
<400> SEQUENCE: 479
acgcgaaaaa aacgcgnana aannaagnna                               30

<210> SEQ ID NO 480
<211> LENGTH: 33
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (2)..(3)
<223> OTHER INFORMATION: n represents thymine ribonucleotide
<220> FEATURE:
<221> NAME/KEY: misc_feature
<222> LOCATION: (10)..(12)
<223> OTHER INFORMATION: n represents thymine ribonucleotide
<220> FEATURE:
<221> NAME/KEY: misc_feature
<222> LOCATION: (15)..(15)
<223> OTHER INFORMATION: n represents thymine ribonucleotide
<220> FEATURE:
<221> NAME/KEY: misc_feature
<222> LOCATION: (18)..(18)
<223> OTHER INFORMATION: n represents thymine ribonucleotide
<220> FEATURE:
<221> NAME/KEY: misc_feature
<222> LOCATION: (22)..(22)
<223> OTHER INFORMATION: n represents thymine ribonucleotide
<220> FEATURE:
<221> NAME/KEY: misc_feature
<222> LOCATION: (27)..(28)
<223> OTHER INFORMATION: n represents thymine ribonucleotide

<400> SEQUENCE: 480
anngaagagn nngancangg cncagannga acg                           33

<210> SEQ ID NO 481
<211> LENGTH: 24
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (5)..(5)
<223> OTHER INFORMATION: n represents thymine ribonucleotide
<220> FEATURE:
<221> NAME/KEY: misc_feature
<222> LOCATION: (7)..(7)
<223> OTHER INFORMATION: n represents thymine ribonucleotide
<220> FEATURE:
<221> NAME/KEY: misc_feature
<222> LOCATION: (10)..(10)
<223> OTHER INFORMATION: n represents thymine ribonucleotide
<220> FEATURE:
<221> NAME/KEY: misc_feature
<222> LOCATION: (13)..(13)
<223> OTHER INFORMATION: n represents thymine ribonucleotide
<220> FEATURE:
<221> NAME/KEY: misc_feature
<222> LOCATION: (15)..(15)
<223> OTHER INFORMATION: n represents thymine ribonucleotide
<220> FEATURE:
<221> NAME/KEY: misc_feature
<222> LOCATION: (18)..(18)
<223> OTHER INFORMATION: n represents thymine ribonucleotide
<220> FEATURE:
<221> NAME/KEY: misc_feature
<222> LOCATION: (20)..(20)
<223> OTHER INFORMATION: n represents thymine ribonucleotide
<220> FEATURE:
<221> NAME/KEY: misc_feature
<222> LOCATION: (22)..(23)
<223> OTHER INFORMATION: n represents thymine ribonucleotide
```

```
<400> SEQUENCE: 481
caccncncan gcncngcncn cnnc                                              24

<210> SEQ ID NO 482
<211> LENGTH: 21
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (20)..(21)
<223> OTHER INFORMATION: n represents thymine ribonucleotide

<400> SEQUENCE: 482
cagagcuuug gagucagcan n                                                 21

<210> SEQ ID NO 483
<211> LENGTH: 25
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (2)..(2)
<223> OTHER INFORMATION: n represents thymine ribonucleotide
<220> FEATURE:
<221> NAME/KEY: misc_feature
<222> LOCATION: (7)..(7)
<223> OTHER INFORMATION: n represents thymine ribonucleotide
<220> FEATURE:
<221> NAME/KEY: misc_feature
<222> LOCATION: (10)..(10)
<223> OTHER INFORMATION: n represents thymine ribonucleotide
<220> FEATURE:
<221> NAME/KEY: misc_feature
<222> LOCATION: (16)..(17)
<223> OTHER INFORMATION: n represents thymine ribonucleotide
<220> FEATURE:
<221> NAME/KEY: misc_feature
<222> LOCATION: (24)..(24)
<223> OTHER INFORMATION: n represents thymine ribonucleotide

<400> SEQUENCE: 483
cngcgcngcn gcaagnnacg gaang                                             25

<210> SEQ ID NO 484
<211> LENGTH: 21
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (20)..(21)
<223> OTHER INFORMATION: n represents thymine ribonucleotide

<400> SEQUENCE: 484
cuggacuucc agaagaacan n                                                 21

<210> SEQ ID NO 485
<211> LENGTH: 25
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (9)..(9)
<223> OTHER INFORMATION: n represents thymine ribonucleotide
<220> FEATURE:
```

```
<221> NAME/KEY: misc_feature
<222> LOCATION: (12)..(12)
<223> OTHER INFORMATION: n represents thymine ribonucleotide
<220> FEATURE:
<221> NAME/KEY: misc_feature
<222> LOCATION: (16)..(17)
<223> OTHER INFORMATION: n represents thymine ribonucleotide
<220> FEATURE:
<221> NAME/KEY: misc_feature
<222> LOCATION: (22)..(22)
<223> OTHER INFORMATION: n represents thymine ribonucleotide

<400> SEQUENCE: 485
gcgcgaaanc angacnnaac gncag                                    25

<210> SEQ ID NO 486
<211> LENGTH: 25
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (3)..(3)
<223> OTHER INFORMATION: n represents thymine ribonucleotide
<220> FEATURE:
<221> NAME/KEY: misc_feature
<222> LOCATION: (10)..(12)
<223> OTHER INFORMATION: n represents thymine ribonucleotide
<220> FEATURE:
<221> NAME/KEY: misc_feature
<222> LOCATION: (15)..(16)
<223> OTHER INFORMATION: n represents thymine ribonucleotide
<220> FEATURE:
<221> NAME/KEY: misc_feature
<222> LOCATION: (24)..(24)
<223> OTHER INFORMATION: n represents thymine ribonucleotide

<400> SEQUENCE: 486
gcnagaccgn nnccnngaac accng                                    25

<210> SEQ ID NO 487
<211> LENGTH: 19
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (10)..(10)
<223> OTHER INFORMATION: n represents thymine ribonucleotide
<220> FEATURE:
<221> NAME/KEY: misc_feature
<222> LOCATION: (13)..(13)
<223> OTHER INFORMATION: n represents thymine ribonucleotide

<400> SEQUENCE: 487
gggggacgan cgncggggg                                           19

<210> SEQ ID NO 488
<211> LENGTH: 30
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (2)..(2)
<223> OTHER INFORMATION: n represents thymine ribonucleotide
<220> FEATURE:
<221> NAME/KEY: misc_feature
<222> LOCATION: (4)..(4)
<223> OTHER INFORMATION: n represents thymine ribonucleotide
<220> FEATURE:
```

```
<221> NAME/KEY: misc_feature
<222> LOCATION: (14)..(14)
<223> OTHER INFORMATION: n represents thymine ribonucleotide
<220> FEATURE:
<221> NAME/KEY: misc_feature
<222> LOCATION: (17)..(17)
<223> OTHER INFORMATION: n represents thymine ribonucleotide
<220> FEATURE:
<221> NAME/KEY: misc_feature
<222> LOCATION: (20)..(20)
<223> OTHER INFORMATION: n represents thymine ribonucleotide
<220> FEATURE:
<221> NAME/KEY: misc_feature
<222> LOCATION: (23)..(24)
<223> OTHER INFORMATION: n represents thymine ribonucleotide

<400> SEQUENCE: 488
gnancaaaaa agangangan acnnggaaga                               30

<210> SEQ ID NO 489
<211> LENGTH: 14
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (9)..(14)
<223> OTHER INFORMATION: n represents thymine ribonucleotide

<400> SEQUENCE: 489
gugugugunn nnnn                                                14

<210> SEQ ID NO 490
<211> LENGTH: 21
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (17)..(17)
<223> OTHER INFORMATION: n represents thymine ribonucleotide

<400> SEQUENCE: 490
guuguguacg gcgccgngcc g                                        21

<210> SEQ ID NO 491
<211> LENGTH: 27
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: n represents thymine ribonucleotide
<220> FEATURE:
<221> NAME/KEY: misc_feature
<222> LOCATION: (9)..(9)
<223> OTHER INFORMATION: n represents thymine ribonucleotide
<220> FEATURE:
<221> NAME/KEY: misc_feature
<222> LOCATION: (12)..(12)
<223> OTHER INFORMATION: n represents thymine ribonucleotide
<220> FEATURE:
<221> NAME/KEY: misc_feature
<222> LOCATION: (24)..(25)
<223> OTHER INFORMATION: n represents thymine ribonucleotide

<400> SEQUENCE: 491
naaggaggng anccaaccgc aggnncc                                  27
```

```
<210> SEQ ID NO 492
<211> LENGTH: 20
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: n represents thymine ribonucleotide
<220> FEATURE:
<221> NAME/KEY: misc_feature
<222> LOCATION: (5)..(5)
<223> OTHER INFORMATION: n represents thymine ribonucleotide
<220> FEATURE:
<221> NAME/KEY: misc_feature
<222> LOCATION: (10)..(11)
<223> OTHER INFORMATION: n represents thymine ribonucleotide
<220> FEATURE:
<221> NAME/KEY: misc_feature
<222> LOCATION: (14)..(14)
<223> OTHER INFORMATION: n represents thymine ribonucleotide
<220> FEATURE:
<221> NAME/KEY: misc_feature
<222> LOCATION: (17)..(17)
<223> OTHER INFORMATION: n represents thymine ribonucleotide
<220> FEATURE:
<221> NAME/KEY: misc_feature
<222> LOCATION: (20)..(20)
<223> OTHER INFORMATION: n represents thymine ribonucleotide

<400> SEQUENCE: 492
nccangacgn nccngangcn                                          20

<210> SEQ ID NO 493
<211> LENGTH: 19
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: n represents thymine ribonucleotide
<220> FEATURE:
<221> NAME/KEY: misc_feature
<222> LOCATION: (4)..(4)
<223> OTHER INFORMATION: n represents thymine ribonucleotide
<220> FEATURE:
<221> NAME/KEY: misc_feature
<222> LOCATION: (7)..(9)
<223> OTHER INFORMATION: n represents thymine ribonucleotide
<220> FEATURE:
<221> NAME/KEY: misc_feature
<222> LOCATION: (19)..(19)
<223> OTHER INFORMATION: n represents thymine ribonucleotide

<400> SEQUENCE: 493
ncgncgnnng uuguguaan                                           19

<210> SEQ ID NO 494
<211> LENGTH: 10
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: n represents thymine ribonucleotide
<220> FEATURE:
<221> NAME/KEY: misc_feature
<222> LOCATION: (4)..(4)
<223> OTHER INFORMATION: n represents thymine ribonucleotide
<220> FEATURE:
```

```
<221> NAME/KEY: misc_feature
<222> LOCATION: (7)..(10)
<223> OTHER INFORMATION: n represents thymine ribonucleotide

<400> SEQUENCE: 494 ncgncgnnnn                                                              10

<210> SEQ ID NO 495
<211> LENGTH: 22
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(22)
<223> OTHER INFORMATION: phosphorothioate internucleotide linkages
<220> FEATURE:
<221> NAME/KEY: misc_feature
<222> LOCATION: (1)..(1)
<223> OTHER INFORMATION: n represents thymine ribonucleotide
<220> FEATURE:
<221> NAME/KEY: misc_feature
<222> LOCATION: (4)..(4)
<223> OTHER INFORMATION: n represents thymine ribonucleotide
<220> FEATURE:
<221> NAME/KEY: misc_feature
<222> LOCATION: (7)..(10)
<223> OTHER INFORMATION: n represents thymine ribonucleotide

<400> SEQUENCE: 495
ncgncgnnnn cggcgcgcgc cg                                                22

<210> SEQ ID NO 496
<211> LENGTH: 22
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: n represents thymine ribonucleotide
<220> FEATURE:
<221> NAME/KEY: misc_feature
<222> LOCATION: (4)..(4)
<223> OTHER INFORMATION: n represents thymine ribonucleotide
<220> FEATURE:
<221> NAME/KEY: misc_feature
<222> LOCATION: (7)..(10)
<223> OTHER INFORMATION: n represents thymine ribonucleotide

<400> SEQUENCE: 496
ncgncgnnnn cggcggccgc cg                                                22

<210> SEQ ID NO 497
<211> LENGTH: 24
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: n represents thymine ribonucleotide
<220> FEATURE:
<221> NAME/KEY: misc_feature
<222> LOCATION: (4)..(4)
<223> OTHER INFORMATION: n represents thymine ribonucleotide
<220> FEATURE:
<221> NAME/KEY: misc_feature
<222> LOCATION: (7)..(10)
<223> OTHER INFORMATION: n represents thymine ribonucleotide
<220> FEATURE:
```

```
<221> NAME/KEY: misc_feature
<222> LOCATION: (12)..(12)
<223> OTHER INFORMATION: n represents thymine ribonucleotide
<220> FEATURE:
<221> NAME/KEY: misc_feature
<222> LOCATION: (15)..(18)
<223> OTHER INFORMATION: n represents thymine ribonucleotide
<220> FEATURE:
<221> NAME/KEY: misc_feature
<222> LOCATION: (20)..(20)
<223> OTHER INFORMATION: n represents thymine ribonucleotide
<220> FEATURE:
<221> NAME/KEY: misc_feature
<222> LOCATION: (23)..(24)
<223> OTHER INFORMATION: n represents thymine ribonucleotide

<400> SEQUENCE: 497
ncgncgnnnn gncgnnnngn cgnn                                              24

<210> SEQ ID NO 498
<211> LENGTH: 24
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: n represents thymine ribonucleotide
<220> FEATURE:
<221> NAME/KEY: misc_feature
<222> LOCATION: (4)..(4)
<223> OTHER INFORMATION: n represents thymine ribonucleotide
<220> FEATURE:
<221> NAME/KEY: misc_feature
<222> LOCATION: (7)..(10)
<223> OTHER INFORMATION: n represents thymine ribonucleotide

<400> SEQUENCE: 498
ncgncgnnnn guuguuugu uguu                                               24

<210> SEQ ID NO 499
<211> LENGTH: 21
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: n represents thymine ribonucleotide
<220> FEATURE:
<221> NAME/KEY: misc_feature
<222> LOCATION: (4)..(4)
<223> OTHER INFORMATION: n represents thymine ribonucleotide
<220> FEATURE:
<221> NAME/KEY: misc_feature
<222> LOCATION: (7)..(11)
<223> OTHER INFORMATION: n represents thymine ribonucleotide
<220> FEATURE:
<221> NAME/KEY: misc_feature
<222> LOCATION: (15)..(15)
<223> OTHER INFORMATION: n represents thymine ribonucleotide
<220> FEATURE:
<221> NAME/KEY: misc_feature
<222> LOCATION: (18)..(21)
<223> OTHER INFORMATION: n represents thymine ribonucleotide

<400> SEQUENCE: 499
ncgncgnnnn ncggncgnnn n                                                 21

<210> SEQ ID NO 500
<211> LENGTH: 22
<212> TYPE: RNA
```

```
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: n represents thymine ribonucleotide
<220> FEATURE:
<221> NAME/KEY: misc_feature
<222> LOCATION: (4)..(4)
<223> OTHER INFORMATION: n represents thymine ribonucleotide
<220> FEATURE:
<221> NAME/KEY: misc_feature
<222> LOCATION: (7)..(10)
<223> OTHER INFORMATION: n represents thymine ribonucleotide

<400> SEQUENCE: 500
ncgncgnnnn uggugguugu ug                                         22

<210> SEQ ID NO 501
<211> LENGTH: 13
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(5)
<223> OTHER INFORMATION: n represents thymine ribonucleotide

<400> SEQUENCE: 501
nnnnngugug ugu                                                   13

<210> SEQ ID NO 502
<211> LENGTH: 24
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: n represents thymine ribonucleotide
<220> FEATURE:
<221> NAME/KEY: misc_feature
<222> LOCATION: (4)..(4)
<223> OTHER INFORMATION: n represents thymine ribonucleotide
<220> FEATURE:
<221> NAME/KEY: misc_feature
<222> LOCATION: (7)..(10)
<223> OTHER INFORMATION: n represents thymine ribonucleotide
<220> FEATURE:
<221> NAME/KEY: misc_feature
<222> LOCATION: (12)..(12)
<223> OTHER INFORMATION: n represents thymine ribonucleotide
<220> FEATURE:
<221> NAME/KEY: misc_feature
<222> LOCATION: (15)..(18)
<223> OTHER INFORMATION: n represents thymine ribonucleotide
<220> FEATURE:
<221> NAME/KEY: misc_feature
<222> LOCATION: (20)..(20)
<223> OTHER INFORMATION: n represents thymine ribonucleotide
<220> FEATURE:
<221> NAME/KEY: misc_feature
<222> LOCATION: (23)..(24)
<223> OTHER INFORMATION: n represents thymine ribonucleotide

<400> SEQUENCE: 502
nugnugnnnn gnugnnnngn ugnn                                       24

<210> SEQ ID NO 503
<211> LENGTH: 22
<212> TYPE: RNA
```

```
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: n represents thymine ribonucleotide
<220> FEATURE:
<221> NAME/KEY: misc_feature
<222> LOCATION: (4)..(4)
<223> OTHER INFORMATION: n represents thymine ribonucleotide
<220> FEATURE:
<221> NAME/KEY: misc_feature
<222> LOCATION: (7)..(10)
<223> OTHER INFORMATION: n represents thymine ribonucleotide

<400> SEQUENCE: 503
nugnugnnnn uggugguugu ug                                           22

<210> SEQ ID NO 504
<211> LENGTH: 21
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (20)..(21)
<223> OTHER INFORMATION: n represents thymine ribonucleotide

<400> SEQUENCE: 504
ugcugacucc aaagcucugn n                                            21

<210> SEQ ID NO 505
<211> LENGTH: 20
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (20)..(20)
<223> OTHER INFORMATION: n represents thymine ribonucleotide

<400> SEQUENCE: 505
uguucuucug gaaguccagn                                              20

<210> SEQ ID NO 506
<211> LENGTH: 25
<212> TYPE: RNA
<213> ORGANISM: Artificial Sequence
<220> FEATURE:
<223> OTHER INFORMATION: synthetic oligonucleotide

<400> SEQUENCE: 506
gagcacgaau ccuaaaccuc aaaga                                        25

<210> SEQ ID NO 507
<211> LENGTH: 25
<212> TYPE: RNA
<213> ORGANISM: Artificial Sequence
<220> FEATURE:
<223> OTHER INFORMATION: synthetic oligonucleotide

<400> SEQUENCE: 507
ucuuugaggu uuaggauucg ugcuc                                        25

<210> SEQ ID NO 508
<211> LENGTH: 10
<212> TYPE: RNA
```

```
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: (1)..(1)
<223> OTHER INFORMATION: um (2'-O-methyl uridine)

<400> SEQUENCE: 508
uuuuuuuuuu                                                          10
```

IMMUNE STIMULATORY OLIGORIBONUCLEOTIDE ANALOGS CONTAINING MODIFIED OLIGOPHOSPHATE MOIETIES

This application corresponds to the national phase of International Application No. PCT/IB2008/002940 filed Oct. 30, 2008, which, in turn, claims priority to U.S. Provisional Application No. 61/002,049 filed Nov. 6, 2007, the contents of which are incorporated by reference herein in their entirety.

BACKGROUND OF THE INVENTION

In recent years a number of nucleic acid molecules, including synthetic oligonucleotides, have been described as immunostimulatory molecules. These immunostimulatory nucleic acid molecules include CpG-containing oligodeoxynucleotides (ODN), which signal through Toll-like receptor 9 (TLR9), as well as double-stranded RNA (dsRNA), which signals through Toll-like receptor 3 (TLR3), and single-stranded RNA and oligoribonucleotides (ORN), which signal through Toll-like receptors 7 and 8 (TLR7 and TLR8).

Very potent induction of interferon by short single-stranded RNAs (ssRNAs), which were obtained by in vitro transcription with T3, T7 and Sp6 RNA polymerases, has also been reported. Kim D H et al. (2004) *Nat Biotechnol* 22:321-5. This report further disclosed that a 5'-triphosphate on the in vitro-transcribed ORN is required for interferon (IFN) induction. These findings were also disclosed in U.S. Patent Application Publication US 2006/0178334 A1.

It was separately reported that 5'-triphosphate RNA is the ligand for retinoic-acid-inducible protein I (RIG-I) and that the 5'-triphosphate group serves as molecular signature for the detection of viral RNA leading to strong IFN induction. Hornung V et al. (2006) *Science* 314:994-7.

5'-Triphosphate groups are energetically activated compounds with a propensity to self-decompose by hydrolysis. Under in vivo conditions, triphosphates are metabolically cleaved, e.g. by 5'-phosphatases such as calf intestinal phosphatase (CIP), and RNA is capped, such that most, if not all, cytoplasmic RNA lacks exposed 5'-triphosphates.

SUMMARY OF THE INVENTION

The present invention provides immunostimulatory oligoribonucleotides (ORN) and oligoribonucleotide analogs with improved metabolic and chemical stability and improved biological activity, compositions containing said immunostimulatory molecules, and methods for the preparation and use thereof.

In certain aspects the immunostimulatory molecules of the invention are characterized in part by having at least one 5'-terminal oligophosphate analog, e.g., a 5'-triphosphate analog. The immunostimulatory molecules according to this aspect can include, in one embodiment, RNA that is otherwise unmodified RNA. According to this embodiment the ORN has a modified 5'-terminal oligophosphate and an otherwise unmodified RNA. Despite having unmodified RNA, the ORN according to this embodiment cannot be obtained by in vitro transcription with T3, T7 and Sp6 RNA polymerases because these enzymes cannot incorporate the 5'-terminal oligophosphate analog. Further according to this aspect of the invention, in one embodiment the immunostimulatory molecules can include RNA that is otherwise characterized by having at least one modified internucleotide linkage, sugar residue, nucleobase, or any combination thereof. According to this embodiment the ORN has a modified 5'-terminal oligophosphate and an RNA that is otherwise modified. ORN according to this embodiment cannot be obtained by in vitro transcription with T3, T7 and Sp6 RNA polymerases because these enzymes cannot incorporate either the 5'-terminal oligophosphate analog or the at least one other RNA modification.

In certain aspects the immunostimulatory molecules of the invention are characterized in part by having at least one 5'-terminal triphosphate. The immunostimulatory molecules according to this aspect can include, in one embodiment, RNA that is otherwise characterized by having at least one modified internucleotide linkage, sugar residue, nucleobase, or any combination thereof. According to this embodiment the ORN has a 5'-terminal triphosphate and an RNA that is otherwise modified. ORN according to this embodiment cannot be obtained by in vitro transcription with T3, T7 and Sp6 RNA polymerases because these enzymes cannot incorporate the at least one RNA modification.

In one embodiment ORN of the invention can be administered using a delivery system, such as a lipid formulation.

The invention in one aspect is an isolated oligoribonucleotide (ORN) including a 5'-triphosphate analog provided as

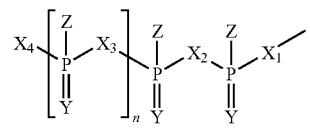

wherein $X_1$ is selected from O, S, and NH and is linked to a 5' carbon of a 5' terminal nucleotide of the ORN;

$X_2$ and each $X_3$, when present, is independently selected from O, S, NH, $CH_2$, $CCl_2$, CHF, and $CF_2$;

$X_4$ is selected from OH, OR, SH, NHR, R, imidazole, and Nu-O—P(Z)(Y)$X_3$, wherein R is selected from a $C_1$-$C_{12}$ alkyl and a $C_6$-$C_{10}$ aryl, and wherein Nu is a nucleoside;

each Y, independent of any other, is selected from O, S, and NH; and each Z, independent of any other, is selected from H, OH, SH, $NH_2$, NHR', $BH_3$, $CF_2H$, $OPO_3H$, OR', and R', wherein R' is selected from $C_1$-$C_{12}$ alkyl, $C_2$-$C_{12}$ alkenyl, $C_2$-$C_{12}$ alkinyl, $C_6$-$C_{10}$ aryl, and $C_7$-$C_{22}$ alkylaryl; and n is an integer between 0 and 3, inclusive, provided that n is 0 only when $X_4$ is imidazole;

proviso the 5'-triphosphate analog is not 5'-triphosphate, and pharmaceutically acceptable salts of said ORN.

In one embodiment n is an integer between 1 and 3, inclusive. In one embodiment n is 1. In one embodiment n is 2. In one embodiment n is 3.

In one embodiment each Y is O.

In one embodiment $X_4$ is selected from OH and O-phenyl. In one embodiment $X_4$ is OH.

In one embodiment the 5'-triphosphate analog is selected from the group consisting of

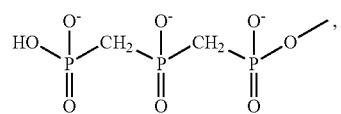

In one embodiment the 5'-triphosphate analog is provided as

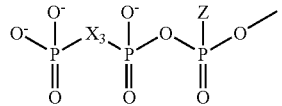

wherein
$X_3$ is selected from O, S, NH, $CH_2$, $CCl_2$, CHF, and $CF_2$; and
Z is selected from H, OH, SH, $NH_2$, NHR', $BH_3$, $CF_2H$, OR', and R', wherein R' is selected from $C_1$-$C_{12}$ alkyl, $C_2$-$C_{12}$ alkenyl, $C_2$-$C_{12}$ alkinyl, $C_6$-$C_{10}$ aryl, and $C_7$-$C_{22}$ alkylaryl; proviso the 5'-triphosphate analog is not 5'-triphosphate.

In one embodiment the 5' terminal nucleotide is G.

In one embodiment the 5' terminal G is part of a dinucleotide selected from GU, GC, and GT.

In one embodiment the 5' terminal nucleotide is not G. For example, the 5' terminal nucleotide can be selected from A, C, U, and T.

The invention in one aspect is an isolated oligoribonucleotide (ORN) including a 5'-triphosphate analog provided as

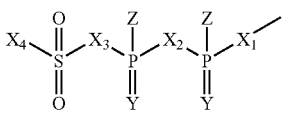

wherein
$X_1$ is selected from O, S, NH, and $CH_2$ and is linked to a 5' carbon of a 5' terminal nucleotide of the ORN;
$X_2$ is selected from O, S, NH, $CH_2$, $CCl_2$, CHF, and $CF_2$;
$X_3$ is selected from O, NH, $CH_2$, $CCl_2$, CHF, and $CF_2$;
$X_4$ is selected from OH, OR, $NH_2$, and R, wherein R is selected from a $C_1$-$C_{12}$ alkyl and a $C_6$-$C_{10}$ aryl;
each Y, independent of the other, is selected from O, S, and NH; and
each Z, independent of the other, is selected from H, OH, SH, NHR', $BH_3$, and $CH_3$, wherein R' is selected from $C_1$-$C_{12}$ alkyl, $C_2$-$C_{12}$ alkenyl, $C_2$-$C_{12}$ alkinyl, $C_6$-$C_{10}$ aryl, and $C_7$-$C_{22}$ alkylaryl, and
and pharmaceutically acceptable salts of said ORN.

In one embodiment each Y is O.

In one embodiment $X_4$ is selected from OH and O-phenyl. In one embodiment $X_4$ is OH.

The invention in one aspect is an isolated oligoribonucleotide (ORN) comprising a 5'-triphosphate analog selected from

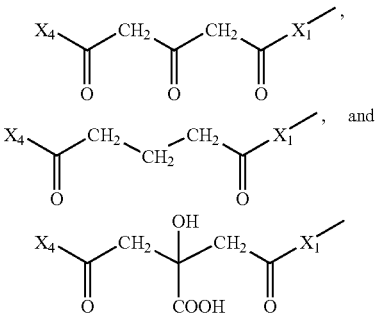

wherein $X_1$ is selected from O and NH and is linked to a 5' carbon of a 5' terminal nucleotide of the ORN; and $X_4$ is selected from OH, OR, $NH_2$, and R, wherein R is selected from a $C_1$-$C_{12}$ alkyl and a $C_6$-$C_{10}$ aryl, and pharmaceutically acceptable salts of said ORN.

In one embodiment $X_4$ is selected from OH and O-phenyl.

In one embodiment $X_4$ is OH.

The invention in one aspect is an isolated oligoribonucleotide (ORN) comprising a 5'-triphosphate analog selected from

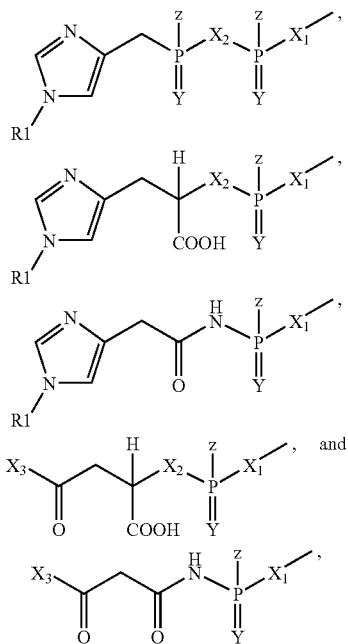

wherein $X_1$ is selected from O, S, and NH and is linked to a 5' carbon of a 5' terminal nucleotide of the ORN;

$X_2$ is selected from O, S, NH, $CH_2$, $CCl_2$, CHF, and $CF_2$;

$X_3$ is selected from OH, OR, R, and $NH_2$, wherein R is selected from $C_1$-$C_{12}$ alkyl and $C_6$-$C_{10}$ aryl;

R1 is selected from H and $C_1$-$C_6$ alkyl;

each Y, independent of any other, is selected from O, S, and NH; and each Z, independent of any other, is selected from H, OH, SH, $NH_2$, NHR', $BH_3$, and $CH_3$, wherein R' is selected from $C_1$-$C_{12}$ alkyl and $C_6$-$C_{10}$ aryl, and pharmaceutically acceptable salts of said ORN.

In one embodiment each Y is O.

In one embodiment $X_3$ is selected from OH and O-phenyl.

In one embodiment $X_3$ is OH.

The invention in one aspect is an isolated oligoribonucleotide (ORN) comprising a 5' terminal end provided as

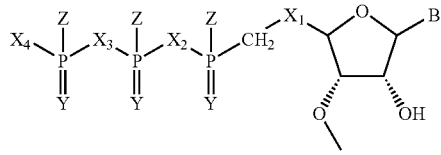

wherein $X_1$ is selected from O, S, and NH;

$X_2$ and each $X_3$ is independently selected from O, S, NH, $CH_2$, $CCl_2$, CHF, and $CF_2$;

$X_4$ is selected from OH, OR, SH, NHR, R, imidazole, and Nu-O—P(Z)(Y)$X_3$, wherein R is selected from a $C_1$-$C_{12}$ alkyl and a $C_6$-$C_{10}$ aryl, and wherein Nu is a nucleoside;

each Y, independent of any other, is selected from O, S, and NH; and each Z, independent of any other, is selected from H, OH, SH, $NH_2$, NHR', $BH_3$, $CF_2H$, $OPO_3H$, OR', and R', wherein R' is selected from $C_1$-$C_{12}$ alkyl, $C_2$-$C_{12}$ alkenyl, $C_2$-$C_{12}$ alkinyl, $C_6$-$C_{10}$ aryl, and $C_7$-$C_{22}$ alkylaryl; and B is H or is a nucleobase selected from guanine, adenine, cytosine, uracil, thymine, and hypoxanthine, and pharmaceutically acceptable salts of said ORN.

In one embodiment each Y is O.

In one embodiment $X_4$ is selected from OH and O-phenyl.

In one embodiment $X_4$ is OH.

For each aspect of the invention:

In one embodiment the ORN comprises at least one immunostimulatory motif selected from the group consisting of RURGY, GUAGU, GUUGB, GUGUG, GUGUU, G/C-U-A/C-G-G-C-A-C, UUGUGG, UGGUUG, GUGUGU, GGGUUU, CUGU, UUGU, CUUU, and UUUU, wherein R is purine; Y is pyrimidine; B is G, C, T, or U; G/C is G or C; and A/C is A or C.

In one embodiment the ORN comprises at least one immunostimulatory motif selected from the group consisting of NCUCAN and UCA, wherein N is C, A, or G.

In one embodiment the ORN further comprises at least one modified internucleoside linkage. In one embodiment the modified internucleoside linkage is selected from the group consisting of phosphorothioate and phosphorodithioate. In one embodiment the modified internucleoside linkage is phosphorothioate.

In one embodiment the ORN further comprises at least one modified sugar residue. In one embodiment the modified sugar residue is selected from the group consisting of α-arabinofuranose, β-D-ribose, β-D-xylo-furanose, α-L-ribose, 2'-[O—($C_1$-$C_6$)alkyl-O—($C_1$-$C_6$)alkyl]-ribose, 2'-amino-2'-deoxyribose, 2'-fluoro arabinofuranose, 2'-fluoro-2'-deoxyribose, 2'-O—($C_1$-$C_6$)alkyl-ribose, 2'-O—($C_2$-$C_6$)alkenyl-ribose, 2'-O-methylribose, 2'-O,4'-C-alkylene-bridged ribose (for example 2'-O,4'-C-methylene-bridged ribose (LNA) and 2'-O,4'-C-ethylene-bridged ribose (ENA)), and β-L-ribose.

In one embodiment the ORN further comprises at least one modified nucleobase. In one embodiment the modified nucleobase is selected from the group consisting of 2,6-diaminopurine; 2-amino-6-chloropurine; 2-aminopurine; 2-thiouracil; 4-thiouracil; 5-($C_1$-$C_6$)-alkylcytosine; 5-($C_1$-$C_6$)-alkyluracil; 5-($C_2$-$C_6$)-alkenylcytosine; 5-($C_2$-$C_6$)-alkenyluracil; 5-($C_2$-$C_6$)-alkynylcytosine; 5-($C_2$-$C_6$)-alkynyluracil; 5-(hydroxymethyl)uracil; 5-aminouracil; 5-bromocytosine; 5-bromouracil; 5-chlorocytosine; 5-chlorouracil; 5-fluorocytosine; 5-fluorouracil; 5-iodouracil; 5-hydroxycytosine; 5-methylcytosine; 5-methyluracil; N4-ethylcytosine; 6-thioguanine; 7-deaza-7-($C_2$-$C_6$)-alkynylguanine; 7-deaza-7-substituted guanine; 7-deaza-7-substituted purine; 7-deaza-8-substituted guanine; 7-deaza-8-substituted purine; 7-deazaguanine; 8-azaguanine; 8-azapurine; 8-hydroxyguanine; 8-hydroxy-adenine; dihydrouracil; hydrogen (abasic nucleotide); hypoxanthine; $N^2$-dimethylguanine; pseudouracil; and substituted 7-deazapurine.

In one embodiment the ORN further comprises at least one abasic nucleotide.

In one embodiment the ORN comprises at least one deoxyribonucleotide.

In one embodiment the ORN is single-stranded.

In one embodiment the ORN is double-stranded.

In one embodiment the ORN is double-stranded and the complementary strands are covalently linked together either by nucleotides or by non-nucleotidic moieties. Such double-stranded ORN include hairpin (or, equivalently, stem-loop) structures, e.g., shRNA which can be processed to remove the loop and leave duplex RNA.

In one embodiment a 3' end of the ORN is conjugated by a linker to a 3' end of another oligonucleotide.

In one embodiment the ORN further comprises a lipophilic moiety conjugated to the ORN. In one embodiment the lipophilic moiety is selected from the group consisting of cholesteryl, palmityl, hexadecylglyceryl, octadecylglyceryl, dihexadecylglyceryl, dioctadecylglyceryl, and fatty acyl. In one embodiment the lipophilic moiety is conjugated to a 3' end of the ORN.

In one embodiment the ORN comprises a poly-G domain. As used herein, apoly-G domain refers to a sequence of at least three consecutive G nucleotides, more preferably at least four consecutive G nucleotides, or in one embodiment a first group of at least three consecutive G nucleotides linked to a second group of at least three consecutive G nucleotides by an intervening UU or TT dinucleotide (i.e., GGGUUGGG or GGGTTGGG). In one embodiment the poly-G sequence enables the formation of G-tetrads. In one embodiment the poly-G domain is composed of G-containing ribonucleotides, deoxynucleotides, LNA-nucleotides, ENA-nucleotides, 2'-O-alkyl-nucleotides (e.g., 2'-O-methyl-nucleotides), 2'-[O—($C_1$-$C_6$)alkyl-O—($C_1$-$C_6$)alkyl]-ribose, 2'-amino-2'-deoxyribose, 2'-fluoro-2'-deoxynucleotides, or any combination thereof. In one embodiment the poly-G domain occurs anywhere in the ORN except for a 5' end. In one embodiment the poly-G domain occurs at a 3' end of the ORN.

In one embodiment the ORN can form higher order structures in solution. In one embodiment the higher order structures are facilitated by G-tetrad formation. In one embodiment the higher order structures are facilitated by Watson-Crick duplex formation.

In one embodiment the ORN further includes a phosphate or phosphate analog linked to the 3' end of the ORN.

In one embodiment the ORN further includes a 2'-O-methyl nucleoside at the 3' end of the ORN.

In one embodiment the ORN further includes a 3'-O-methyl nucleoside at the 3' end of the ORN.

In one embodiment the ORN further includes a poly-A tail at the 3' end. In one embodiment the poly-A tail at the 3' end of the ORN is linked to the ORN via a 3'5' linkage. In one embodiment the poly-A tail at the 3' end of the ORN is linked to the ORN via a 2'5' linkage. A poly-A tail is a sequence of at least 3-100 consecutive A nucleotides. For example, a poly-A tail in one embodiment is AAAAAAAAAAAA (SEQ ID NO: 1). For a poly-A tail at the 3' end of the ORN linked to the ORN via a 3'5' linkage, a poly-A tail in one embodiment is 10-50 consecutive A nucleotides. For a poly-A tail at the 3' end of the ORN linked to the ORN via a 2'5' linkage, a poly-A tail in one embodiment is 3-10 consecutive A nucleotides.

In one embodiment the ORN is 2-100 nucleotides long.

In one embodiment the ORN is 4-40 nucleotides long.

In one embodiment the ORN is 6-30 nucleotides long.

In one embodiment the ORN has a sequence provided as UUGUUGUUGUUGUUGUUGUU (SEQ ID NO: 429).

In one aspect the invention is a pharmaceutical composition that includes an isolated oligoribonucleotide of the invention, and a pharmaceutically acceptable carrier. In one embodiment the pharmaceutical composition further includes an antigen.

In one embodiment the ORN is formulated so as to direct the ORN to cytosol, liposomes, or to both cytosol and liposomes. In one embodiment the ORN is administered as part of a nucleic acid delivery system. In one embodiment the nucleic acid delivery system includes a cationic lipid. In one embodiment the nucleic acid delivery system delivers the ORN to the cytosol of a cell. In one embodiment the nucleic acid delivery system delivers the ORN to the endosomal compartment of a cell, where the ORN can encounter certain TLRs such as TLR7 and TLR8.

In one aspect the invention is a method of enhancing an immune response in a subject. The method according to this aspect of the invention includes the step of administering to a subject in need of an enhanced immune response an effective amount of an oligoribonucleotide of the invention to enhance the immune response in the subject.

In one embodiment the immune response comprises production of a cytokine selected from the group consisting of interferon alpha (IFN-☐), interleukin 12 (IL-12), and a combination thereof.

In one embodiment the immune response is a Th1-type immune response.

In one embodiment the subject has immune suppression resulting from chemotherapy and/or therapeutic radiation exposure.

In one embodiment the subject has immune suppression resulting from accidental radiation exposure.

In one aspect the invention is a method of treating a subject having cancer. The method according to this aspect of the invention includes the step of administering to the subject an effective amount of an oligoribonucleotide of the invention to treat the cancer.

The invention in one aspect is a method of treating a subject having an allergic condition, other than asthma. The method according to this aspect of the invention includes the step of administering to the subject an effective amount of an oligoribonucleotide of the invention to treat the allergic condition.

The invention in one aspect is a method of treating a subject having asthma. The method according to this aspect of the invention includes the step of administering to the subject an effective amount of an oligoribonucleotide of the invention to treat the asthma. In one embodiment the asthma is allergic asthma.

The invention in one aspect is a method of treating a subject having an infection. The method according to this aspect of the invention includes the step of administering to the subject an effective amount of an oligoribonucleotide of any one of claims A1-F24 to treat the infection. In one embodiment the infection is a viral infection. In one embodiment the infection is a bacterial infection.

The invention in one aspect is a method of vaccinating a subject against an antigen. The method according to this aspect of the invention includes the step of administering to the subject an effective amount of an oligoribonucleotide of the invention and the antigen. In one embodiment the antigen is selected from the group consisting of proteins, peptides, carbohydrates, lipids, DNA vaccines, RNA vaccines, and any combination thereof.

The invention in one aspect is a method for preparing an ORN of the invention. The method according to this aspect includes the step of chemically synthesizing the ORN.

The invention in one aspect is a method for preparing an ORN of the invention. The method according to this aspect includes the step of synthesizing the ORN on a solid support.

The invention in one aspect is a method for preparing an ORN of the invention. The method according to this aspect includes the steps of activating an ORN with a 5'-monophosphate with an activating reagent and then reacting the activated ORN with pyrophosphate or a pyrophosphate analog, to give a triphosphate or triphosphate analog.

The invention in one aspect is a method for preparing an ORN of the invention. The method according to this aspect includes the steps of synthesizing the ORN on a solid support; reacting a nucleotide at a 5'-end of the ORN with 2-chloro-4H-1,3,2-benzodioxa-phosphorin-4-one in a suitable solvent and in the presence of a base; reacting the ORN with pyrophosphate or a pyrophosphate analog; oxidizing the ORN with an oxidizing reagent; and deprotecting the ORN, to give a triphosphate or triphosphate analog.

In one embodiment the base is diisopropylethylamine.

In one embodiment the solvent is dichloromethane.

In one embodiment the pyrophosphate or pyrophosphate analog is a tetra-n-butylammonium salt.

In one embodiment the pyrophosphate or pyrophosphate analog is a tri-n-butylammonium salt.

In one embodiment the oxidizing reagent is iodine.

In one embodiment the oxidizing reagent is a peroxide.

In one embodiment the oxidizing reagent is sulfurization reagent.

In one embodiment the oxidizing reagent is a borane.

The invention in one aspect is a method for preparing a pharmaceutical composition. The method according to this aspect includes the step of mixing at least one ORN of the invention with a physiologically acceptable excipient or carrier. In one embodiment the carrier comprises a cationic lipid.

The invention in one aspect is an isolated ORN of the invention, wherein the ORN comprises a sequence complementary to a target RNA.

In one embodiment the target RNA is a viral RNA.

In one embodiment the target RNA is derived from a tumor-causing gene.

The invention in one aspect is an isolated ORN of the invention, wherein the ORN is part of a double-stranded RNA and wherein at least one strand of the double-stranded RNA is complementary to a target RNA.

In one embodiment the target RNA is a viral RNA.

In one embodiment the target RNA is derived from a tumor-causing gene.

In one embodiment both strands of the double-stranded RNA have a 5'-triphosphate or 5'-triphosphate analog.

DETAILED DESCRIPTION OF THE INVENTION

Chemical synthesis of ORN with a triphosphate or modified triphosphate at the 5'-end has not previously been described in the literature. ORN with a 5'-triphosphate group can be prepared by in vitro transcription using T3, T7 and Sp6 RNA polymerases. For example, preparation of ORN-5'-triphosphates has been achieved previously using T7 RNA polymerase and templates of synthetic DNA which contain the T7 promoter. Milligan et al. (1987) *Nucleic Acids Res* 15:8783-8. Furthermore, enzymatic preparation is done in small quantities only. The RNA polymerases accept unmodified nucleoside triphosphates and nucleoside-[alpha-S]-triphosphates, the latter resulting in enantiomerically pure phosphorothioate-modified ORN with a 5'-[alpha-S]-triphosphate.

The polymerase promoters and polymerases have certain additional limitations. The 5'-nucleotide (+1) must be a G and the second nucleotide at the 5'-end (+2) must be G or A. Therefore, ORN with pyrimidines at the 5'-end can not be made by in vitro transcription (Promega Notes 94, August 2006). In addition, the enzymatic method appears not to be appropriate to prepare larger quantities of ORN-5'-triphosphates required for therapeutic applications. In contrast, chemical synthesis of ORN with modified triphosphate groups can provide any sequence, and synthesis can be performed on a scale suitable for therapeutic applications.

Figure 1:
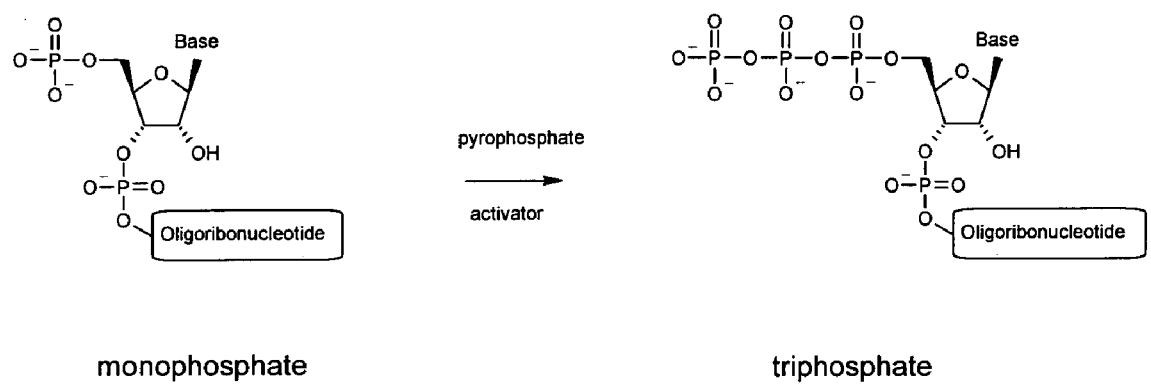
FIG. 1 depicts a post-synthesis derivativization of oligoribonucleotide-5'-monophosphate to yield oligoribonucleotide 5'-triphosphate.

In principle, there are two basic strategies of how ORN-5'-triphosphates and derivatives thereof can be chemically synthesized. Firstly, the ORN can be synthesized by standard oligonucleotide synthesis methods as ORN-5'-monophosphate, which is optionally purified and then converted post-synthesis to the corresponding ORN-5'-triphosphate. The ORN-5'-monophosphate can be activated by condensation reagents, such as cyanogen bromide/Imidazole, N-cyanoimidazole, or carbodiimides (CDI), and then reacted with pyrophosphate or a modified pyrophosphate to yield the corresponding ORN-5'-triphosphate derivative. See FIG. 1.

Alternatively, ORN-5'-triphosphate can be synthesized on solid support. The basic chemistry underlying this route has been described for the synthesis of monomeric nucleoside-5'-triphosphates. Ludwig and Eckstein (1989) *J Org Chem* 54:631-5. This synthetic route has later been adapted for the synthesis of short DNA with a 5'-triphosphate. Lebedev A V et al. Nucleosides, *Nucleotides & Nucleic Acids* (2001) 20(4-7):1403-9).

Figure 2:
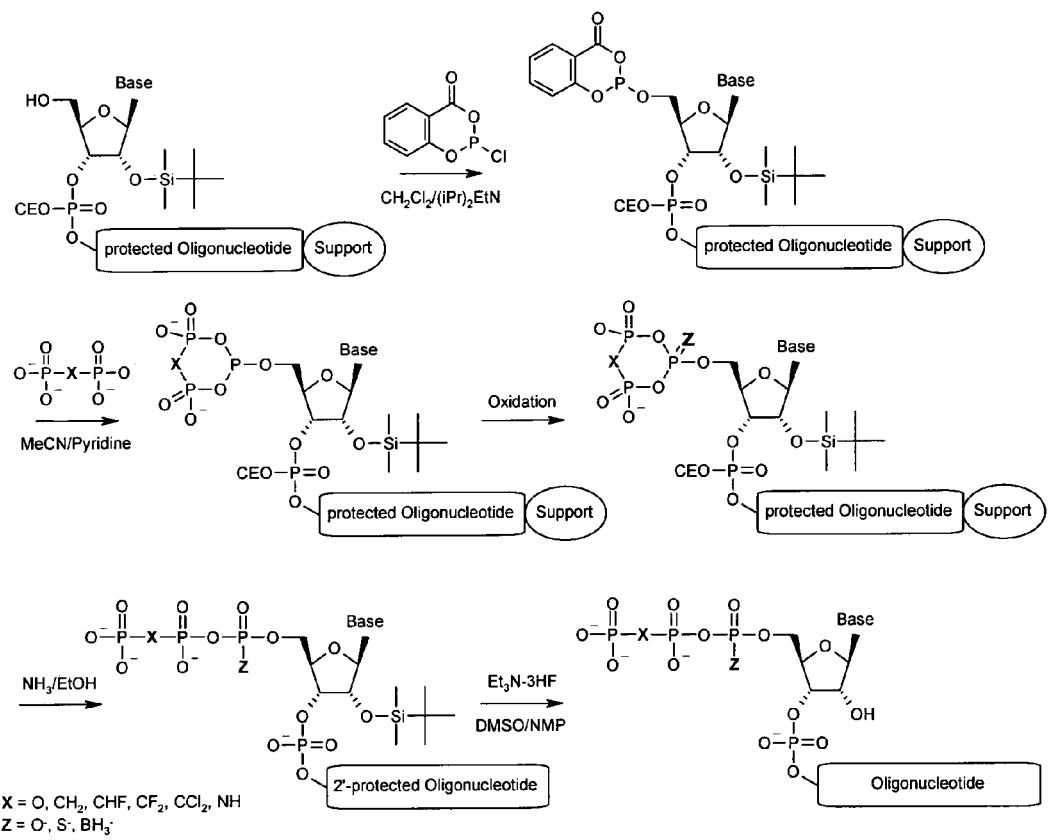
FIG. 2 depicts a solid-phase synthesis of oligoribonucleotide 5'-triphosphate.

This basic method has now been further developed by the applicant for the synthesis of RNA with a 5'-triphosphate and also with modified 5'-triphosphate moieties. See FIG. 2. The ORN can be synthesized on the polymer support using standard phosphoramidite RNA synthesis. After coupling of the last nucleotide, the dimethoxytrityl (DMT) group is cleaved from the last nucleotide, resulting in an unprotected 5'-hydroxyl group which is reacted with 2-chloro-4H-1,3,2-benzodioxa-phosphorin-4-one and diisopropylethylamine (DIPEA) in dichloromethane to give the trivalent salicyl phosphite intermediate. The use of DIPEA in dichloromethane resulted in higher yields as compared to the dioxane/pyridine (4:1) mixture originally described by Lebedev et al. The reactive intermediate is subsequently converted to the cyclic 5'-triphosphite by reaction with pyrophosphate (X is O) or a modified pyrophosphate (X is different from O; e.g., $CH_2$, $CCl_2$, NH, or $CF_2$). The pyrophosphate as tetra-butylammonium salt appears to give higher yields of triphosphate as compared to the tri-butylammonium salt. The cyclic triphosphite is then oxidized with iodine/water, phenylacetyldisulfide (PADS) or borane-diisopropylethylamine (DIPEA) complex, respectively, to give after treatment with ammonia/ethanol the corresponding triphosphate (Z is O), α-thiotriphosphate (Z is S) or a-boranotriphosphate (Z is $BH_3$), respectively. The ammonia treatment also cleaves the ORN from the solid support and removes all protecting groups, except the 2'-O-tert-butyl-dimethylsilyl group, which is removed by subsequent fluoride treatment.

Depending on the type of pyrophosphate and oxidation reagent, a large variety of differently modified ORN-5'-triphosphate analogs can be prepared. Some examples of and triphosphate analogs as well as used pyrophosphates and oxidizing reagents are shown in Table 1.

TABLE 1

Typical examples for triphosphates and reagents used for their synthesis.

| Abbreviation | Triphosphate analog | Pyrophosphate | Oxidizer |
|---|---|---|---|
| — | (standard triphosphate) | (standard pyrophosphate) | Iodine/water |
| —$CH_2$— | (methylene-bridged, H substituent) | (methylene-bridged) | Iodine/water |
| —$CCl_2$— | (dichloromethylene-bridged) | (dichloromethylene-bridged) | Iodine/water |
| —*— | (phosphorothioate, S⁻ on β-P) | (standard pyrophosphate) | PADS |
| —&— | (boranophosphate, $BH_3$ on β-P) | (standard pyrophosphate) | Borane/DIPEA |
| —NH— | (imido-bridged, NH) | (imido-bridged, NH) | Iodine/water |
| —CHF— | (fluoromethylene-bridged, CHF) | (fluoromethylene-bridged, CHF) | Iodine/water |
| —$CF_2$— | (difluoromethylene-bridged, $CF_2$) | (difluoromethylene-bridged, $CF_2$) | Iodine/water |

The invention provides a number of oligoribonucleotides (ORN) that include a 5'-triphosphate or 5'-triphosphate analog attached to a 5' terminal nucleotide of the ORN. As used herein, the term "oligoribonucleotide" refers in general to a polymer of 2-100 ribonucleotides and/or ribonucleotide analogs. Oligoribonucleotides that include at least one ribonucleotide analog are also referred to as oligoribonucleotide analogs. The invention thus contemplates oligoribonucleotides which, apart from a 5'-triphosphate or 5'-triphosphate analog, are traditional oligoribonucleotides, as well as oligoribonucleotides which, apart from a 5'-triphosphate or 5'-triphosphate analog, are oligoribonucleotide analogs.

Except as may be specified otherwise herein, the terms "ribonucleotide" and "nucleotide" are used interchangeably to refer to a molecule composed of a D-ribose sugar linked to a phosphoric acid group and a heterocyclic nucleobase (such as guanine, adenine, cytosine, or uracil). A base-sugar unit is called a nucleoside, and a base-sugar-phosphoric acid unit is called a nucleotide.

In one embodiment the oligoribonucleotide is a linear polymer. In one embodiment the oligoribonucleotide is a branched polymer that includes at least one 5'-triphosphate or 5'-triphosphate analog.

In one embodiment the ORN has a 5'-triphosphate attached to a 5' terminal nucleotide of the ORN. As used herein a 5'-triphosphate has its usual meaning and has a structural formula provided as

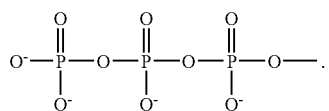

It will be understood by persons skilled in the art that any one or more of the O⁻ groups can equivalently be represented by hydroxyl (OH). The ORN according to this embodiment is an oligoribonucleotide analog that includes at least one modified nucleotide and cannot be made by enzymatic means, for example by in vitro transcription using T3, T7 or Sp6 RNA polymerases. As described in detail elsewhere herein, a modified nucleotide includes a sugar, phosphate, and/or heterocyclic nucleobase that is modified compared to corresponding features of natural nucleotides G, A, C, and U.

In one embodiment the ORN has a 5'-triphosphate analog attached to a 5' terminal nucleotide of the ORN. As used herein a 5'-triphosphate analog has a structure as disclosed herein and excludes 5'-triphosphate. The ORN according to this embodiment can, but need not necessarily, include at least one modified nucleotide. Thus in one embodiment the invention provides a traditional oligoribonucleotide except for the presence of a 5'-triphosphate analog. In another embodiment the invention provides an oligoribonucleotide analog further modified by the presence of a 5'-triphosphate analog. It should be noted that ORN of the invention having a 5'-triphosphate analog generally cannot be made by enzymatic means, for example by in vitro transcription using T3, T7 or Sp6 RNA polymerases.

The 5'-triphosphate or 5'-triphosphate analog is linked to a 5' terminal nucleotide of the ORN. As used herein, a "5'-triphosphate" has its usual meaning and denotes a triphosphate group (shown above) covalently linked to the 5' carbon of a 5' terminal nucleotide of an ORN. As used herein, a "5'-triphosphate analog" has a corresponding meaning and denotes a triphosphate analog (as disclosed herein) covalently linked to the 5' carbon of a 5' terminal nucleotide of an ORN. A 5' terminal nucleotide of an ORN refers to the first nucleotide in an ORN as represented in 5'-to-3' orientation; it is also referred to as the nucleotide in the +1 position.

In one embodiment the 5'-triphosphate analog refers to

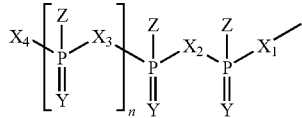

wherein $X_1$ is selected from O, S, and NH and is linked to a 5' carbon of a 5' terminal nucleotide of the ORN;

$X_2$ and each $X_3$, when present, is independently selected from O, S, NH, $CH_2$, $CCl_2$, CHF, and $CF_2$;

$X_4$ is selected from OH, OR, SH, NHR, R, imidazole, and Nu—O—P(Z)(Y)$X_3$, wherein R is selected from a $C_1$-$C_{12}$ alkyl and a $C_6$-$C_{10}$ aryl, and wherein Nu is a nucleoside;

each Y, independent of any other, is selected from O, S, and NH; and each Z, independent of any other, is selected from H, OH, SH, $NH_2$, NHR', $BH_3$, $CF_2H$, $OPO_3H$, OR', and R', wherein R' is selected from $C_1$-$C_{12}$ alkyl, $C_2$-$C_{12}$ alkenyl, $C_2$-$C_{12}$ alkinyl, $C_6$-$C_{10}$ aryl, and $C_7$-$C_{22}$ alkylaryl; and n is an integer between 0 and 3, inclusive, provided that n is 0 only when $X_4$ is imidazole.

In respect of Z and $X_4$ it will be understood by persons of skill in the art that any one or more of OH, SH, $BH_3$, and $OPO_3H$ groups can equivalently be represented as $O^-$, $S^-$, $BH3^-$, and $OPO_3^-$, respectively.

$C_1$-$C_{12}$ alkyl refers to methyl, ethyl, propyl, butyl, pentyl, hexyl, heptyl, octyl, nonyl, decyl, undecyl, and dodecyl, either unbranched (n-alkyl) or branched (e.g., iso-alkyl, such as iso-propyl, iso-butyl, iso-amyl, iso-bornyl, iso-menthyl, tertiary-butyl), or for $C_{\geq 6}$ also cyclo-alkyl, such as cyclohexyl.

$C_6$-$C_{10}$ aryl includes but is not limited to phenyl, pyridyl, naphthyl, quinolinyl, and isoquinolinyl.

$C_2$-$C_{12}$ alkenyl includes but is not limited to ethylenyl, propylenyl, 1-butenyl, 1-pentenyl, 1-hexenyl-1-heptenyl, 1-octenyl, 1-nonenyl, 1-decenyl, cis-2-butenyl, trans-2-butenyl, isobutenyl, cis-2-pentenyl, trans-2-pentenyl, 3-methyl-1-butenyl, 2-methyl-2-butenyl, 2,3-dimethyl-2-butenyl, hexadienolyl, geranyl, and phytyl.

$C_2$-$C_{12}$ alkinyl includes but is not limited to acetylenyl, propynyl, 1-butynyl, 1-pentynyl, 1-hexynyl, 1-heptynyl, 1-octynyl, 1-nonynyl, 1-decynyl, 2-butynyl, 2-pentynyl, 3-methyl-1-butynyl, 2-hexynyl, 3-hexynyl, 3,3-dimethyl-1-butynyl, 4-octynyl, and 5-decynyl.

$C_7$-$C_{22}$ alkylaryl includes but is not limited to benzyl, phenyl, phenyl-2-ethyl, and phenyl-3-propyl. In one embodiment R' is tocopheryl (a $C_{2-9}$ alkylaryl).

In one embodiment the ORN comprises a 5' terminal nucleoside or 5' terminal nucleoside analog linked to a 5'-triphosphate or 5'-triphosphate analog provided as

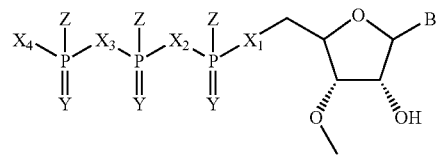

wherein $X_1$ is selected from O, S, and NH;

$X_2$ and each $X_3$ is independently selected from O, S, NH, $CH_2$, $CCl_2$, CHF, and $CF_2$;

$X_4$ is selected from OH, OR, SH, NHR, R, imidazole, and Nu—O—P(Z)(Y)$X_3$, wherein R is selected from a $C_1$-$C_{12}$ alkyl and a $C_6$-$C_{10}$ aryl, and wherein Nu is a nucleoside;

each Y, independent of any other, is selected from O, S, and NH; and each Z, independent of any other, is selected from H, OH, SH, $NH_2$, NHR', $BH_3$, $CF_2H$, $OPO_3H$, OR', and R', wherein R' is selected from $C_1$-$C_{12}$ alkyl, $C_2$-$C_{12}$ alkenyl, $C_2$-$C_{12}$ alkinyl, $C_6$-$C_{10}$ aryl, and $C_7$-$C_{22}$ alkylaryl; and B is H or is a nucleobase selected from adenine, cytosine, uracil, thymine, and hypoxanthine.

In respect of Z and $X_4$ it will be understood by persons of skill in the art that any one or more of OH, SH, $BH_3$, and $OPO_3H$ groups can equivalently be represented as $O^-$, $S^-$, $BH3^-$, and $OPO_3^-$, respectively. $C_1$-$C_{12}$ alkyl, $C_6$-$C_{10}$ aryl, $C_2$-$C_{12}$ alkenyl, $C_2$-$C_{12}$ alkinyl, and $C_7$-$C_{22}$ alkylaryl are as described above.

In one embodiment the 5'-triphosphate analog refers to

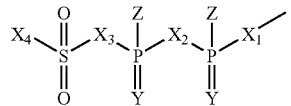

wherein $X_1$ is selected from O, S, NH, and $CH_2$ and is linked to a 5' carbon of a 5' terminal nucleotide of the ORN;

$X_2$ is selected from O, S, NH, $CH_2$, $CCl_2$, CHF, and $CF_2$;

$X_3$ is selected from O, NH, $CH_2$, $CCl_2$, CHF, and $CF_2$;

$X_4$ is selected from H, OH, OR, $NH_2$, and R, wherein R is selected from a $C_1$-$C_{12}$ alkyl and a $C_6$-$C_{10}$ aryl;

each Y, independent of the other, is selected from O, S, and NH; and each Z, independent of the other, is selected from OH, SH, NHR', $BH_3$, and $CH_3$, wherein R' is selected from $C_1$-$C_{12}$ alkyl, $C_2$-$C_{12}$ alkenyl, $C_2$-$C_{12}$ alkinyl, $C_6$-$C_{10}$ aryl, and $C_7$-$C_{22}$ alkylaryl.

In respect of Z and $X_4$ it will be understood by persons of skill in the art that any one or more of OH, SH, and $BH_3$ groups can equivalently be represented as $O^-$, $S^-$, and $BH3^-$, respectively. $C_1$-$C_{12}$ alkyl, $C_6$-$C_{10}$ aryl, $C_2$-$C_{12}$ alkenyl, $C_2$-$C_{12}$ alkinyl, and $C_7$-$C_{22}$ alkylaryl are as described above.

In one embodiment the 5'-triphosphate analog refers to a 5'-triphosphate analog selected from wherein $X_1$ is selected from O and NH and is linked to a 5' carbon of a 5' terminal nucleotide of the ORN; and $X_4$ is selected from OH, OR, $NH_2$, and R, wherein R is selected from a $C_1$-$C_{12}$ alkyl and a $C_6$-$C_{10}$ aryl.

In respect of $X_4$ it will be understood by persons of skill in the art that OH can equivalently be represented as $O^-$. It will also be understood by persons of skill in the art that COOH can equivalently be represented as $COO^-$. $C_1$-$C_{12}$ alkyl and $C_6$-$C_{10}$ aryl are as described above.

In one embodiment the 5'-triphosphate analog refers to a 5'-triphosphate analog selected from wherein $X_1$ is selected from O, S, and NH and is linked to a 5' carbon of a 5' terminal nucleotide of the ORN;

$X_2$ is selected from O, S, NH, $CH_2$, $CCl_2$, CHF, and $CF_2$;

$X_3$ is selected from OH, OR, R, and $NH_2$, wherein R is selected from $C_1$-$C_{12}$ alkyl and $C_6$-$C_{10}$ aryl;

R1 is selected from H and $C_1$-$C_6$ alkyl;

each Y, independent of any other, is selected from O, S, and NH; and each Z, independent of any other, is selected from H, OH, SH, NHR', $BH_3$, and $CH_3$, wherein R' is selected from $C_1$-$C_{12}$ alkyl and $C_6$-$C_{10}$ aryl.

In respect of Z and $X_3$ it will be understood by persons of skill in the art that any one or more of OH, SH, and $BH_3$ groups can equivalently be represented as $O^-$, $S^-$, and $BH3^-$, respectively. It will also be understood by persons of skill in the art that COOH can equivalently be represented as $COO^-$. $C_1$-$C_{12}$ alkyl and $C_6$-$C_{10}$ aryl are as described above.

In one embodiment the ORN comprises a 5' terminal end provided as wherein $X_1$ is selected from O, S, and NH;

$X_2$ and each $X_3$ is independently selected from O, S, NH, $CH_2$, $CCl_2$, CHF, and $CF_2$;

$X_4$ is selected from OH, OR, SH, NHR, R, imidazole, and Nu—O—P(Z)(Y)$X_3$, wherein R is selected from a $C_1$-$C_{12}$ alkyl and a $C_6$-$C_{10}$ aryl, and wherein Nu is a nucleoside;

each Y, independent of any other, is selected from O, S, and NH; and each Z, independent of any other, is selected from H, OH, SH, $NH_2$, NHR', $BH_3$, $CF_2H$, $OPO_3H$, OR', and R', wherein R' is selected from $C_1$-$C_{12}$ alkyl, $C_2$-$C_{12}$ alkenyl, $C_2$-$C_{12}$ alkinyl, $C_6$-$C_{10}$ aryl, and $C_7$-$C_{22}$ alkylaryl; and B is H or is a nucleobase selected from guanine, adenine, cytosine, uracil, thymine, and hypoxanthine.

In respect of Z and $X_4$ it will be understood by persons of skill in the art that any one or more of OH, SH, $BH_3$, and $OPO_3H$ groups can equivalently be represented as $O^-$, $S^-$, $BH3^-$, and $OPO_3^-$, respectively. $C_1$-$C_{12}$ alkyl, $C_6$-$C_{10}$ aryl, $C_2$-$C_{12}$ alkenyl, $C_2$-$C_{12}$ alkinyl, and $C_7$-$C_{22}$ alkylaryl are as described above.

The invention also contemplates pharmaceutically acceptable salts of any of the ORN of the invention. As used herein, the term "pharmaceutically acceptable salts" has its usual meaning as understood in the pharmaceutical arts and specifically includes, without limitation, those salts prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Generally, pharmaceutically acceptable salts can also be prepared as alkaline metal or alkaline earth salts, such as sodium, potassium, or calcium salts. Pharmaceutically acceptable salts, of particular interest in connection with ORN of the invention, specifically also include, without limitation, those salts prepared from the following bases: ammonia, pyridine, piperidine, trimethylamine, triethylamine, tributylamine, picoline, dicyclohexylamine, diethanolamine, tris(hydroxymethylamino)-methane, phenylethylbenzylamine, spermine, spermidine, lysine, and arginine.

ORN of the invention are immunostimulatory and are useful whenever it is desirable to enhance an immune response. In one embodiment an ORN of the invention includes at least one immunostimulatory motif provided as a specific RNA sequence motif. Such immunostimulatory RNA sequence motif can include at least one of the following sequences: RURGY, wherein R is purine and Y is pyrimidine; GUAGU; GUUGB, wherein B is G, C, T, or U; GUGUG; GUGUU; G/C-U-A/C-G-G-C-A-C, wherein G/C is G or C and A/C is A or C; UUGUGG; UGGUUG; GUGUGU; GGGUUU; CUGU; UUGU; CUUU; and UUUU. In addition to GUAGU, RURGY specifically includes but is not limited to GUGGC, GUGGU, AUGGC, AUGGU, GUAGC, AUAGC, and AUAGU. GUUGB specifically includes GUUGG, GUUGC, GUUGU, and GUUGT. G/C-U-A/C-G-G-C-A-C specifically includes GUAGGCAC, GUCGGCAC, CUAGGCAC, and CUCGGCAC. Immunostimulatory RNA sequence motifs can also include NCUCAN (wherein each N is independently C, A, or G, but not U) as well as UCA. NCUCAN specifically includes CCUCAC, CCUCAA, CCUCAG, ACUCAC, ACUCAA, ACUCAG, GCUCAC, GCUCAA, and GCUCAG.

Exemplary sequences of ORN of the invention include but are not limited to the following:

```
                                          (SEQ ID NO: 3)
AAAAUAAAAUAAAAUAAAAU (SEQ ID NO: 4)
AAAAUCAUCAUCUCUUGUUUUUGUGUGUCU (SEQ ID NO: 5)
AAACAACAAACACACAAACC (SEQ ID NO: 6)
AAACUCUUGUCUGGU (SEQ ID NO: 7)
AAAUAAAUAAAUAAAUAAAU (SEQ ID NO: 8)
AACACGUAUCCAUAUUUCCCCUUGUUCGGU (SEQ ID NO: 9)
AACAUCUACCUGCUUUUGCU (SEQ ID NO: 10)
AACAUUAUUAACCCCUGCUUCUGCU (SEQ ID NO: 11)
AACCCUGCUUUUGCU (SEQ ID NO: 12)
AACUGGACUUCCAGAAGAACAUU (SEQ ID NO: 13)
AAUAUCUACCUGCUUUCGCU (SEQ ID NO: 14)
AAUAUCUACCUGCUUUGCU (SEQ ID NO: 15)
AAUCACUAUAGUUUUUUGUUUUUCUCCGU (SEQ ID NO: 16)
AAUCAGUACCUGCUUUCGCU (SEQ ID NO: 17)
AAUCAGUACCUGCUUUUGCU (SEQ ID NO: 18)
AAUCUCCUGCUUUUG (SEQ ID NO: 19)
AAUCUUAGCU (SEQ ID NO: 20)
AAUGCUGACUCCAAAGCUCUGUU (SEQ ID NO: 21)
AAUGGUUUAUUUGUCUUCGU (SEQ ID NO: 22)
AAUGGUUUGUUUGUCUUCGU (SEQ ID NO: 23)
AAUGGUUUUUUGUCUUCGU (SEQ ID NO: 24)
AAUUUCCCCUGCUUUUGCU (SEQ ID NO: 25)
ACCCAUCUAUUAUAUAACUC (SEQ ID NO: 26)
ACCCCUGCUUUUGCU (SEQ ID NO: 27)
ACCGAUAUCCCAUCUUCAUUUUCCCCUUGG (SEQ ID NO: 28)
ACUCCUGCUUUUGCU (SEQ ID NO: 29)
AGCCAUUUUGACUGCCUGUUUUUGCU (SEQ ID NO: 30)
AGCGAAAGCAGGUCAAUUAU (SEQ ID NO: 31)
AGCUCCGCUUCUGCU (SEQ ID NO: 32)
AGUCUCUUCUCUUGUUUGGU (SEQ ID NO: 33)
AGUUUCUUCUCUUGUUUGGU (SEQ ID NO: 34)
AGUUUUUCCUCUUGUUUGGU (SEQ ID NO: 35)
AGUUUUUUCUCUUGUUUGGU (SEQ ID NO: 36)
AUAAUUGACCUGCUUUCGCU (SEQ ID NO: 37)
AUAAUUGACCUGCUUUUCGU (SEQ ID NO: 38)
AUAAUUGCGCUGCUUUCGCU

AUAGGCAC (SEQ ID NO: 39)
AUAUAUAUAUAUAUAUAUAU (SEQ ID NO: 40)
AUAUCAAUUAGUUUUUUUGUUUUUUCUCGU (SEQ ID NO: 41)
AUAUUAGAAAAUGCAACGCUUCUGCU
```

AUAUUCAUUCUCCCCUUGGU (SEQ ID NO: 42)

AUAUUUUCGGC (SEQ ID NO: 43)

AUCAUCAUCUUUUUUGAUAC (SEQ ID NO: 44)

AUCAUCUCUUGUUUUUGUGUGUCU (SEQ ID NO: 45)

AUCCAUUCAAAUGGUUUCGCUGCUUUCGCU (SEQ ID NO: 46)

AUCCAUUCAAAUGGUUUGCCUGCUUUCGCU (SEQ ID NO: 47)

AUCCAUUCAAAUGGUUUGCCUGCUUUUGCU (SEQ ID NO: 48)

AUCCAUUCAAGUGGUUUGCCUGCUUUUGCU (SEQ ID NO: 49)

AUCCCAUACAUGUUUUUCUCUUGUUUGGU (SEQ ID NO: 50)

AUCUCUUGUUUUUGUGUGUC (SEQ ID NO: 51)

AUCUUCAUUUUCCCCUUGGU (SEQ ID NO: 52)

AUCUUCUUUUUCCCCUUGGU (SEQ ID NO: 53)

AUGGUUUCGCUGCUUUCGCU (SEQ ID NO: 54)

AUGGUUUGCCUGCUUUCGCU (SEQ ID NO: 55)

AUGGUUUGCCUGCUUUUGCU (SEQ ID NO: 56)

AUGGUUUUUUGUUAAGCGU (SEQ ID NO: 57)

AUGUCAUCUUGAAAACGCUCCGCUUCUGCU (SEQ ID NO: 58)

AUUCAAAUGGUUUGCCUGCUUUCGCU (SEQ ID NO: 59)

AUUCAUUUAAACCCCUGCUUUCGCU (SEQ ID NO: 60)

AUUCCAAACAAGUUUCUUCUCUUGUUUGGU (SEQ ID NO: 61)

AUUCCAAACAAGUUUUUCCUCUUGUUUGGU (SEQ ID NO: 62)

AUUCCAAACAUGUUUCUUCUCUUGUUUGGU (SEQ ID NO: 63)

AUUCCAUACACGUUUUUUCUCUUGUCUGGU (SEQ ID NO: 64)

AUUCCAUACAUGUUUCUUCUCUUGUUUGGU (SEQ ID NO: 65)

AUUCCAUGCAAGUUUUUUCUCUUGUUUGGU (SEQ ID NO: 66)

AUUCUUCUUUCUUUUUGUGUGUCCG (SEQ ID NO: 67)

AUUGGUUUGUUUUUCUUCGU (SEQ ID NO: 68)

AUUGGUUUUUUUGUCUUCGU (SEQ ID NO: 69)

AUUUGGAUUCAUUUUAAUCUCCUGCUUUUG (SEQ ID NO: 70)

AUUUUAAGAAAGUGCGUGCUUCUGCU (SEQ ID NO: 71)

AUUUUAAUCUCCUGCUUUUG (SEQ ID NO: 72)

AUUUUCCCCUGCUUUUGCUA (SEQ ID NO: 73)

AUUUUGGAUCAGUACCUGCUUUCGCU (SEQ ID NO: 74)

CAAAAUCAUCAUCUCUUGUUUUUGUGUGUC (SEQ ID NO: 75)

CACACACUGCUUAAGCGCUUGCCUGCUUAAGUAGUGUGUG (SEQ ID NO: 76)

CACCCUGCUUUUGCU (SEQ ID NO: 77)

CAGAGCUUUGGAGUCAGCAUU (SEQ ID NO: 78)

CAGGUCUGUGAU (SEQ ID NO: 79)

CAGUGAGUGAUUAUCAACCCUGCUUUUGCU (SEQ ID NO: 80)

CAGUGAGUGAUUAUUAACCCUGCUUUUGCU (SEQ ID NO: 81)

CAUAGCCAACUUUUUCUGGU (SEQ ID NO: 82)

CAUAUUCAAUAUAAUUGACCUGCUUUUCGU (SEQ ID NO: 83)

CAUAUUGAAUAUAAUUGACCUGCUUUCGCU (SEQ ID NO: 84)

CAUAUUGAAUAUAAUUGCGCUGCUUUCGCU (SEQ ID NO: 85)

CAUAUUCCCCUUGUUCGGU (SEQ ID NO: 86)

CAUCUUCAUUUUCCCCUUGG (SEQ ID NO: 87)

CAUCUUGAAAACGCUCCGCUUCUGCU (SEQ ID NO: 88)

CAUCUUUAUGAUAC (SEQ ID NO: 89)

CAUCUUUUUGAUAC (SEQ ID NO: 90)

CAUUCUCCCCUUGGU (SEQ ID NO: 91)

CAUUGAGUGAUUAUCUACCCUGCUUUUGCU (SEQ ID NO: 92)

CAUUUUCCCCUUGGU (SEQ ID NO: 93)

CCAACAUCCCAUCUUCUUUUUCCCCUUGGU (SEQ ID NO: 94)

CCAACUUUGUCUGGU (SEQ ID NO: 95)

-continued

CCAACUUUGUUUGGU (SEQ ID NO: 96)

CCAACUUUUUCUGGU (SEQ ID NO: 97)

CCAAUAUCCCAUAUUCAUUCUCCCCUUGGU (SEQ ID NO: 98)

CCAAUAUCCCAUCUUCAUUUUCCCCUUGGU (SEQ ID NO: 99)

CCAGCUUUGUCUGGU (SEQ ID NO: 100)

CCAGCUUUGUUUGGU (SEQ ID NO: 101)

CCAUUAUGUCUUUGUCACCCUGCUUUUGCU (SEQ ID NO: 102)

CCCCUGCUUUUGCUA (SEQ ID NO: 103)

CCCCUUUUGGGGG (SEQ ID NO: 104)

CCCUGCUUUUGCUAA (SEQ ID NO: 105)

CCGAGCCAUAUAUAUC (SEQ ID NO: 106)

CCGAGCCAUAUAUCCC (SEQ ID NO: 107)

CCGAGCCGAAGAUACC (SEQ ID NO: 108)

CCGAGCCGAAGCUACC (SEQ ID NO: 109)

CCGAGCCGAAGCUCCC (SEQ ID NO: 110)

CCGAGCCGAAGCUGCC (SEQ ID NO: 111)

CCGAGCCGAAGGCACC (SEQ ID NO: 112)

rC*rC*rG*rA*rG*rC*rC*rG*rA*rA*rG*rG*rC*rA*rC*rC (SEQ ID NO: 113)

CCGAGCCGAAGGUACC (SEQ ID NO: 114)

CCGAGCCGAAGGUCCC (SEQ ID NO: 115)

CCGAGCCGAAGGUGCC (SEQ ID NO: 116)

CCGAGCCGAAUAACCC (SEQ ID NO: 117)

CCGAGCCGAAUCCCCC (SEQ ID NO: 118)

CCGAGCCGAAUGUACC (SEQ ID NO: 119)

CCGAGCCGAAUUCACC (SEQ ID NO: 120)

CCGAGCCGAAUUUACC (SEQ ID NO: 121)

rC*rC*mG*rA*rG*rC*rC*rG*rA*rC*rC*rU*rU*rG*rU*rA*rC*rC (SEQ ID NO: 122)

CCGAGCCGACUGUACC (SEQ ID NO: 123)

CCGAGCCGACUUUACC (SEQ ID NO: 124)

CCGAGCCGAGCUCACC (SEQ ID NO: 125)

CCGAGCCGAGUUCACC (SEQ ID NO: 126)

CCGAGCCGAGUUUACC (SEQ ID NO: 127)

CCGAGCCGANUGUACC (SEQ ID NO: 128)

CCGAGCCGANUUCACC (SEQ ID NO: 129)

CCGAGCCGAUAUUACC (SEQ ID NO: 130)

CCGAGCCGAUCUCACC (SEQ ID NO: 131)

CCGAGCCGAUCUUACC (SEQ ID NO: 132)

CCGAGCCGAUGUUACC (SEQ ID NO: 133)

CCGAGCCGAUNUNACC (SEQ ID NO: 134)

CCGAGCCGAUUCNACC (SEQ ID NO: 135)

CCGAGCCGAUUGAACC (SEQ ID NO: 136)

CCGAGCCGAUUGCACC (SEQ ID NO: 137)

mC*rC*rG*rA*rG*rC*rC*rG*rA*rU*rU*rG*rU*rA*rC*rC (SEQ ID NO: 138)

rC*rC*rG*rA*rG*rC*rC*rG*rA*rU*rU*rG*rU*rA*rC*rC (SEQ ID NO: 139)

rC*rC*rG*rA*rG*rC*rC*mG*rA*rU*rU*rG*rU*rA*rC*rC (SEQ ID NO: 140)

rC*rC*rG*rA*rG*rC*rC*rG*mA*rU*rU*rG*rU*rA*rC*rC (SEQ ID NO: 141)

rC*rC*rG*rA*rG*rC*rC*rG*rA*mU*rU*rG*rU*rA*rC*rC (SEQ ID NO: 142)

rC*rC*rG*rA*rG*rC*rC*rG*rA*rU*mU*rG*rU*rA*rC*rC (SEQ ID NO: 143)

rC*rC*rG*rA*rG*rC*rC*rG*rA*rU*rU*mG*rU*rA*rC*rC (SEQ ID NO: 144)

rC*rC*rG*rA*rG*rC*rC*rG*rA*rU*rU*rG*mU*rA*rC*rC (SEQ ID NO: 145)

rC*rC*rG*rA*rG*rC*rC*rG*rA*rU*rU*rG*rU*mA*rC*rC (SEQ ID NO: 146)

rC*rC*rG*rA*rG*rC*rC*rG*rA*rU*rU*rG*rU*rA*mC*rC (SEQ ID NO: 147)

rC*rC*rG*rA*rG*rC*rC*rG*rA*rU*rU*rG*rU*rA*rC*rC (SEQ ID NO: 148)

CCGAGCCGAUUUAACC (SEQ ID NO: 149)

|  |  |
|---|---|
| CCGAGCCGAUUUCACC | (SEQ ID NO: 150) |
| CCGAGCCGAUUUNACC | (SEQ ID NO: 151) |
| CCGAGCCGCAUAACCC | (SEQ ID NO: 152) |
| CCGAGCCGCAUACCCC | (SEQ ID NO: 153) |
| CCGAGCCGCAUAUCCC | (SEQ ID NO: 154) |
| CCGAGCCGCAUCCCCC | (SEQ ID NO: 155) |
| CCGAGCCGCAUUACCC | (SEQ ID NO: 156) |
| CCGAGCCGCAUUCCCC | (SEQ ID NO: 157) |
| CCGAGCCGCCGCCCCC | (SEQ ID NO: 158) |
| CCGAGCCGCCUAACCC | (SEQ ID NO: 159) |
| CCGAGCCGCCUACCCC | (SEQ ID NO: 160) |
| CCGAGCCGCUAUACCC | (SEQ ID NO: 161) |
| CCGAGCCGCUAUCCCC | (SEQ ID NO: 162) |
| CCGAGCCGCUAUUCCC | (SEQ ID NO: 163) |
| CCGAGCCGCUUAACCC | (SEQ ID NO: 164) |
| rC*rC*rG*rA*rG*rC*rC*rG*mC*rU*rU*rG*rU*rC*rC*rC | (SEQ ID NO: 165) |
| rC*rC*rG*rA*rG*rC*rC*rG*rC*rU*rU*rG*rU*mC*rC*rC | (SEQ ID NO: 166) |
| rC*rC*rG*rA*rG*rC*rC*rG*rC*rU*rU*rG*rU*rC*rC*rC | (SEQ ID NO: 167) |
| CCGAUAUCCCAUCUUCUUUUUCCCCUUGGU | (SEQ ID NO: 168) |
| CCGUCUGUUGUGUGACAG | (SEQ ID NO: 169) |
| rC-rC-rG-rU-rC-rU-rG-rU-rU-rG-rU-rG-rU-rG-rA-rC-rU-rC | (SEQ ID NO: 170) |
| rC*rC*rG*rU*rC*rU*rG*rU*rU*rG*rU*rG*rU*rG*rA*rC* rU*rC | (SEQ ID NO: 171) |
| CCGUCUGUUGUUGGACUC | (SEQ ID NO: 172) |
| CCUGCUUUUG | (SEQ ID NO: 173) |
| CGACUCUCUCUUCAGUUG | (SEQ ID NO: 174) |
| CGAGCCGAAUACCCC | (SEQ ID NO: 175) |
| CGAGCCGCUUACCCC | (SEQ ID NO: 176) |
| CGCAAGUUUGUUGUACGCAUUUUUUCGCGU | (SEQ ID NO: 177) |
| CGCACCGCUUCUGCU | (SEQ ID NO: 178) |
| CGCAUUUUUUCCCGU | (SEQ ID NO: 179) |
| CGCAUUUUUUCGCGU | (SEQ ID NO: 180) |
| CGCUCCGCUUCUGCU | (SEQ ID NO: 181) |
| CGCUUCUGCU | (SEQ ID NO: 182) |
| CGGCGCGCGCCGUUUU | (SEQ ID NO: 183) |
| CGGCGGCCGCCGUUUU | (SEQ ID NO: 184) |
| CGGCGGCCGCCGUUUUUU | (SEQ ID NO: 185) |
| CGGCUUUUGCCG | (SEQ ID NO: 186) |
| CGGUGAGAGAUUAUCUACCCUGCUUUUGCU | (SEQ ID NO: 187) |
| CGGUGAGUGAUUAUCUACCCUGCUUUUGCU | (SEQ ID NO: 188) |
| CGUAUCGCUUCUGCU | (SEQ ID NO: 189) |
| CGUUUUUUCUCUUGUCUGGU | (SEQ ID NO: 190) |
| CUAAAAAUUCUUCUUUCUUUUUGUGUGCCC | (SEQ ID NO: 191) |
| CUACCUGCUUUCGCU | (SEQ ID NO: 192) |
| CUACCUGCUUUUGCU | (SEQ ID NO: 193) |
| CUACUACUACUACUACUCUAGGCAC | (SEQ ID NO: 194) |
| CUCAUCAUCUUUUAUGAUAC | (SEQ ID NO: 195) |
| CUCAUCUUUCAACAUCUACCUGCUUUUGCU | (SEQ ID NO: 196) |
| CUCAUCUUUCAAUAUCUACCUGCUUUCGCU | (SEQ ID NO: 197) |
| CUCAUCUUUCAAUAUCUACCUGCUUUUGCUCUCGGCAC | (SEQ ID NO: 198) |
| CUCUCUCUCUCUCUCUCUCU | (SEQ ID NO: 199) |
| CUCUUAAACUCUUGUCUGGU | (SEQ ID NO: 200) |
| CUGAGCUUAGUCAAGUUACUUUUCUUAUAC | (SEQ ID NO: 201) |

CUGAGCUUAGUCAAGUUACUUUUUUAUAC (SEQ ID NO: 202)

CUGGUUGUUAAGCGU (SEQ ID NO: 203)

CUGGUUUUGUUGUUAAGCGU (SEQ ID NO: 204)

CUGUUGUGUGACAG (SEQ ID NO: 205)

CUUAAAGCUCCGCUUCUGCU (SEQ ID NO: 206)

CUUACCCAACUUUGUUUGGU (SEQ ID NO: 207)

CUUACCCAGCUUUGUCUGGU (SEQ ID NO: 208)

CUUACCCAGCUUUGUUUGGU (SEQ ID NO: 209)

CUUAGCCAACUUUGUCUGGU (SEQ ID NO: 210)

CUUCGGCUUCGG (SEQ ID NO: 211)

CUUCUCUUGUUUGGU (SEQ ID NO: 212)

CUUGUCUGGU (SEQ ID NO: 213)

CUUGUUCGGU (SEQ ID NO: 214)

CUUGUUUGGU (SEQ ID NO: 215)

CUUUUCUUCUCUGGUUUUGUUGUUAAGCGU (SEQ ID NO: 216)

CUUUUGCUAA (SEQ ID NO: 217)

CUUUUUCCCCUUGGU (SEQ ID NO: 218)

CUUUUUGUGUGUCCG (SEQ ID NO: 219)

GAAAACGCUCCGCUUCUGCU (SEQ ID NO: 220)

GAAAAUAGCCAAUCUUAGCU (SEQ ID NO: 221)

GAAAAUGCUCUGCUUCUGCU (SEQ ID NO: 222)

GACAUUUCCAAUCCCCUGCUUCUGCU (SEQ ID NO: 223)

GACAUUUCGGAUCCCCUGCUUCUGCU (SEQ ID NO: 224)

GACUAAACAAAUGCUCUGCUUCUGCU (SEQ ID NO: 225)

GAGAUGGGUGCGAGAGCGUCAGUAUU (SEQ ID NO: 226)

GAGUGAUUAUCUACCCUGCUUUUGCU (SEQ ID NO: 227)

rG*mA*mU*rA*rC*rU*rU*rA*rC*rC*rU*rG (SEQ ID NO: 228)

rG*mA*rU*rA*rC*rU*rU*rA*rC*rC*rU*rG (SEQ ID NO: 229)

rG*rA*mU*rA*rC*rU*rU*rA*rC*rC*rU*rG (SEQ ID NO: 230)

rG-rA-mU-rA-rC-rU-rU-rA-rC-rC-rU-rG (SEQ ID NO: 231)

rG*rA*rU*rA*rC*rU*rU*rA*rC*rC*rU*rG (SEQ ID NO: 232)

GAUCAGUACCUGCUUUCGCU (SEQ ID NO: 233)

GAUCAGUACCUGCUUUUGCU (SEQ ID NO: 234)

GAUCUUUCGGC (SEQ ID NO: 235)

GAUCUUUUGAUC (SEQ ID NO: 236)

GAUUCUCUGUUUGGU (SEQ ID NO: 237)

GAUUUCCAUAAUCCCCUGCUUCUGCU (SEQ ID NO: 238)

GAUUUCCCCUGCUUUUGCU (SEQ ID NO: 239)

GCCACCGAGCCGAAGGCACC (SEQ ID NO: 240)

GCCACCGAGCCGAAUAUACC (SEQ ID NO: 241)

GCCCGACAGAAGAGAGACAC (SE ID NO: 242)

mG*rC*rC*rG*rA*rC*rC*rG*rA*rU*rU*rG*rU*rA*rC*rC (SEQ ID NO: 243)

GCCCGUCUGUUGUGUGACUC (SEQ ID NO: 244)

GCGAUUUCUGACCGCUUUUUUGUCAG (SEQ ID NO: 245)

GCGUUUUUUCGCGU (SEQ ID NO: 246)

GCUUUUGCUA (SEQ ID NO: 247)

GGACUUUGGUCC (SEQ ID NO: 248)

GGAUACAUAUCUCUUAAACUCUUGUCUGGU (SEQ ID NO: 249)

GGAUUCAUUUUGAACUCCUGCUUUUGCUAA (SEQ ID NO: 250)

GGCAAAUCAAACGCACCGCUUCUGCU (SEQ ID NO: 251)

GGCUCCGCUUCUGCU (SEQ ID NO: 252)

rG*rG*rC*rU*rU*rA*rU*rC*rC*rA*rU*rU*rG*rC*mA*rC*rU*rC*rC*rG (SEQ ID NO: 253)

rG*rG*rC*rU*rU*rA*rU*rC*rC*rA*rU*rU*rG*rC*rA*rC*rU*rC*rC*rG*rG (SEQ ID NO: 254)

```
                                                      (SEQ ID NO: 255)
rG*rG*rG*rG-rA-rA-rA-rA-rA-rA-rA-rA-rA-rG*rG*
rG*rG*rG*rG*rG (SEQ ID NO: 256)
GGGGGGGUUGUGU (SEQ ID NO: 257)
GGGGGGGUUGUGUGGGGG (SEQ ID NO: 258)
GGGGGGGUGUGUGU (SEQ ID NO: 259)
GGGGGUUUUU (SEQ ID NO: 260)
rG*rG*rG*rG*rU*rU*rA*rU*rU*rA*rU*rU*rA*rU*rG*rG*
rG*rG*rG*rG*rG (SEQ ID NO: 261)
rG*rG*rG*rG*rU*rU*rG*rU*rU*rG*rU*rU*rG*rU*rG*rG*
rG*rG*rG*rG*rG

GGGGUUUU (SEQ ID NO: 262)
GGGGUUUUCCCC (SEQ ID NO: 263)
GGGGUUUUGGGG (SEQ ID NO: 264)
GGGGUUUUGGGGG (SEQ ID NO: 265)
rG*rG*rG*rG*rU*rU*rU*rU*rU*rU*rU*rU*rU*rG*rG*
rG*rG*rG*rG*rG (SEQ ID NO: 266)
rG*rG*rG*rG-rU-rU-rU-rU-rU-rU-rU-rU-rU-rG*rG*
rG*rG*rG*rG*rG (SEQ ID NO: 267)
GGUUGCUUUUAUUUCCCCUGCUUUUGCUA (SEQ ID NO: 268)
GUACCUGCUUUCGCU (SEQ ID NO: 269)
GUACCUGCUUUUGCU

GUAGGCAC

GUAGUAG (SEQ ID NO: 270)
GUAGUAGUAGUAGUAGU

GUAGUGU (SEQ ID NO: 271)
GUAGUGUGUG (SEQ ID NO: 272)
GUCGGCGUUGAC (SEQ ID NO: 273)
GUCGUCGUCGUCGUCGU (SEQ ID NO: 274)
GUCUGUUGUGUG (SEQ ID NO: 275)
GUGGAUAUUAGAAAAUGCUCUGCUUCUGCU (SEQ ID NO: 276)
GUGGGUUUGCCUGCUUUUGCU

GUGU
GUGUG

GUGUGU

GUGUGUGU (SEQ ID NO: 277)
GUGUGUGUGGGGG (SEQ ID NO: 278)
GUGUGUGUGUGUGUGUGUGU

GUGUUUAC

GUUG

GUUGB (SEQ ID NO: 279)
GUUGCUUUUAUUUCCCCUGCUUUUGCUAA

GUUUGU

GUUUGUG (SEQ ID NO: 280)
GUUUGUGGUUGUGGUUGUG

GUUUGUGU rG*rU*rU*rG*rU*rG*rU rG*rU*rU*rG*rU*rG*rU-Acr rG*rU*rU*rG*rU*rG*rU-BIOT rG*rU*rU*rG*rU*rG*rU-CHOL rG*rU*rU*rG*rU*rG*rU-FAM rG*rU*rU*rG*rU*rG*rU-HEX rG*rU*rU*rG*rU*rG*rU-TEG

GUUUGUGUA (SEQ ID NO: 281)
rG*rU*rU*rG*rU*rG*rU*rA*rA*rA*rA*rA

GUUUGUGdA (SEQ ID NO: 282)
rG*rU*rU*rG*rU*rU*rG*rU*rE*rG*rG*rG rG*rU*rU*rG*rU*rU*rG*rU*rG*rG (SEQ ID NO: 283)
GUUUGUGUGGGGG (SEQ ID NO: 284)
rG*rU*rU*rG*rU*rG*rU*rG*rG*rG*rG (SEQ ID NO: 285)
rG*rU*rU*rG*rU*rG*rU*G*G*G*G (SEQ ID NO: 286)
G*rU*rU*rG*rU*rG*rU*rG*rG*rG*rG (SEQ ID NO: 287)
GUUUGUGUUUUUACGGCGCCGUGCCG

GUUUGUUU (SEQ ID NO: 288)
GUUUGUUUUGUUGUU (SEQ ID NO: 289)
GUUUGUGUGGG
```

-continued

GUUUGUGUGGG (SEQ ID NO: 290)

GUUUUGU

GUUUUUG

GUUUUUU

GUUUUUUUGUUUUUCUCCGU (SEQ ID NO: 291)

GUUUUUUUGUUUUUCUCGU (SEQ ID NO: 292)

NNNNNANANANANNNNNNN (SEQ ID NO: 293)

NNNNNNANANNNNNNNNN (SEQ ID NO: 294)

NNNNNNNUUGUNNNNNNNN (SEQ ID NO: 295)

NNNNNNUUUUNNNNNNNN (SEQ ID NO: 296)

NUANUANUANUANUANUANU (SEQ ID NO: 297)

dTdCdGdTdCdGdTdTdTGUUGUGUdAdAdT (SEQ ID NO: 298)

UAAAAAACCUUUUUUCUUUUUGUGUGUCCG (SEQ ID NO: 299)

UAAAAAUUCUUCUUUCUUUUUGUGUGUCCG (SEQ ID NO: 300)

UAACUUAAUUUAUACGCGUUUUUUUCGCGU (SEQ ID NO: 301)

UAAGAAUGCUAUGGUUUGUUUUCUUCGU (SEQ ID NO: 302)

UAAUGAUAAUAAUGGUUUGUUUGUCUUCGU (SEQ ID NO: 303)

UAAUGGUAAUAAUGGUUUGUUUGUCUUCGU (SEQ ID NO: 304)

UAAUGUUAUCAAUGGUUUAUUUGUCUUCGU (SEQ ID NO: 305)

UAAUUAUAUUAAUGGUUUGUUUGUCUUCGU (SEQ ID NO: 306)

UAAUUGUAAGAAUGGUUUUUUUUGUCUUCGU (SEQ ID NO: 307)

UAAUUGUAAUAAUGGUUUUUUUGUCUUCGU (SEQ ID NO: 308)

UACCCUGCUUUUGCU (SEQ ID NO: 309)

UAGAACGAUCCUUACCCAGCUUUUGUCUGGU (SEQ ID NO: 310)

UAGACCGAUCCUUACCCAACUUUGUUUGGU (SEQ ID NO: 311)

UAGCCAAUCUUAGCU (SEQ ID NO: 312)

UAGUACGCAUUUUUCGCGU (SEQ ID NO: 313)

UAUACCUAUCCUUACCCAGCUUUUGUUUGGU (SEQ ID NO: 314)

UAUACGCGUUUUUUCGCGU (SEQ ID NO: 315)

UAUAUAU (SEQ ID NO: 316)

UAUAUUCAUCUUAAAGGCUCCGCUUCUGCU (SEQ ID NO: 317)

UAUCCAUCUUGAAAAUAGCCAAUCUUAGCU (SEQ ID NO: 318)

UAUGUCUUUGUCACCCUGCUUUUGCU (SEQ ID NO: 319)

UAUUUUCCCCUGCUUUUGCU (SEQ ID NO: 320)

UCAAACGCACCGCUUCUGCU (SEQ ID NO: 321)

UCAAACGUAUCGCUUCUGCU (SEQ ID NO: 322)

UCAAGUUACUUUUCUUAUAC (SEQ ID NO: 323)

UCAAGUUACUUUUUUUAUAC (SEQ ID NO: 324)

UCACAGAUUCUCUGUUUGGU (SEQ ID NO: 325)

UCACCGAUUCUCUGUUUGGU (SEQ ID NO: 326)

UCACGGAUUCUCUGUUUGGU (SEQ ID NO: 327)

UCAUUUCCCCUUGG (SEQ ID NO: 328)

UCCCCUGCUUUUGCU (SEQ ID NO: 329)

UCCCCUUGGU (SEQ ID NO: 330)

UCCGCAAUGGACGAAAGUCUGACGGA (SEQ ID NO: 331)

UCCUGCUUUUGCUAA

UCCUUUCUU (SEQ ID NO: 332)

UCGACGUCGAUUUU (SEQ ID NO: 333)

UCGACGUCGAUUUUCGGCGCGCGCCG (SEQ ID NO: 334)

UCUCCUGCUUUUGCU

UCUCUCU (SEQ ID NO: 335)

UCUCUUGUUUUUGUGUGUCU (SEQ ID NO: 336)

UCUGUUUGGU (SEQ ID NO: 337)

UCUUCCAAGUAUCAUCAUCUUUUUUGAUAC (SEQ ID NO: 338)

UCUUUCAAUAUCUACCUGCUUUCGCU (SEQ ID NO: 339)

UCUUUCUUUUUGUGUGUCCG

-continued

| | |
|---|---|
| UCUUUUUGUGUGCCC | (SEQ ID NO: 340) |
| UGAACUCCUGCUUUUGCUAA | (SEQ ID NO: 341) |
| UGAAGGAACAUCUGCUUGUUUUUGCU | (SEQ ID NO: 342) |
| UGACCUGCUUUCGCU | (SEQ ID NO: 343) |
| UGACCUGCUUUUCGU | (SEQ ID NO: 344) |
| UGAGAAGAAAAUGCUGUGCUUCUGCU | (SEQ ID NO: 345) |
| UGAUUUUAUAUGGUUUUUUGUUAAGCGU | (SEQ ID NO: 346) |
| UGCAAGUUUGUAGUACGCAUUUUUCGCGU | (SEQ ID NO: 347) |
| UGCAAGUUUGUUGUACGCAUUUUUCCCGU | (SEQ ID NO: 348) |
| UGCGCUGCUUUCGCU | (SEQ ID NO: 349) |
| UGCUCUGCUUCUGCU | (SEQ ID NO: 350) |
| UGCUUCUGCU | (SEQ ID NO: 351) |
| UGCUUCUUCUUUGGUUUUGUUGUUAAGCGU | (SEQ ID NO: 352) |
| UGCUUUCGCU | (SEQ ID NO: 353) |
| UGCUUUUCGU | (SEQ ID NO: 354) |
| UGCUUUUGCU | (SEQ ID NO: 355) |
| UGGU | |
| UGGUGGUUGUUG | (SEQ ID NO: 356) |
| UGGUUGAUUUAAUUUUCCCCUGCUUUUGCU | (SEQ ID NO: 357) |
| UGGUUGAUUUGAUUUCCCCUGCUUUUGCU | (SEQ ID NO: 358) |
| UGGUUGAUUUUAUUUUCCCCUGCUUUUGCU | (SEQ ID NO: 359) |
| UGGUUGCUUUUAUUUUCCCCUGCUUUUGCU | (SEQ ID NO: 360) |
| UGGUUGGUUUUAUUUUCCCCUGCUUUUGCU | (SEQ ID NO: 361) |
| UGGUUGUAUUUAUUUUCCCCUGCUUUUGCU | (SEQ ID NO: 362) |
| UGGUUGUUUUAUUUUCCCCUGCUUUUGCU | (SEQ ID NO: 363) |
| UGUAACAUAACUCAUCAUCUUUUAUGAUAC | (SEQ ID NO: 364) |

| | |
|---|---|
| UGUCAUGUCAAGUGCUUGUUUUUGCU | (SEQ ID NO: 365) |
| UGUG | |
| UGUGU | |
| UGUGUCUUCUUUGAUCUGGUUGUUAAGCGU | (SEQ ID NO: 366) |
| UGUGUGU | |
| UGUGUGUCCG | (SEQ ID NO: 367) |
| UGUUAAGCGU | (SEQ ID NO: 368) |
| UGUUCUUCUGGAAGUCCAGUU | (SEQ ID NO: 369) |
| UGUUUCUUCUCUUGUUGGU | (SEQ ID NO: 370) |
| UGUUUUAUUUCCCCUGCUUUUGCU | (SEQ ID NO: 371) |
| UGUUUUUGUGUGUCU | (SEQ ID NO: 372) |
| UGUUUUUUCUCUUGUUGGU | (SEQ ID NO: 373) |
| UGUUUUUUCUUUGAUCUGGUUGUUAAGCGU | (SEQ ID NO: 374) |
| UUAAAGGCUCCGCUUCUGCU | (SEQ ID NO: 375) |
| UUACAGAUUCUCUGUUUGGU | (SEQ ID NO: 376) |
| UUACCAAGCAAGUUUCUUCUCUUGUUUGGU | (SEQ ID NO: 377) |
| UUACGGAUUCUCUGUUUGGU | (SEQ ID NO: 378) |
| UUACUUUUCUUAUAC | (SEQ ID NO: 379) |
| UUACUUUUUUAUAC | (SEQ ID NO: 380) |
| UUAGGCAC | |
| UUAUAUUCAUCUUAAAGCUCCGCUUCUGCU | (SEQ ID NO: 381) |
| UUAUCAACCCUGCUUUUGCU | (SEQ ID NO: 382) |
| UUAUCGUAACUCACCGAUUCUCUGUUUGGU | (SEQ ID NO: 383) |
| UUAUCGUAACUCACGGAUUCUCUGUUUGGU | (SEQ ID NO: 384) |
| UUAUCGUAACUUACGGAUUCUCUGUUUGGU | (SEQ ID NO: 385) |
| UUAUCGUACCUCACAGAUUCUCUGUUUGGU | (SEQ ID NO: 386) |
| UUAUCGUACCUUACAGAUUCUCUGUUUGGU | (SEQ ID NO: 387) |
| UUAUCUACCCUGCUUUUGCU | (SEQ ID NO: 388) |

UUAUGGCAAAUCAAACGCACCGCUUCUGCU (SEQ ID NO: 389)

UUAUGGCAAAUCAAACGUAUCGCUUCUGCU (SEQ ID NO: 390)

UUAUUAACCCUGCUUUUGCU (SEQ ID NO: 391)

UUAUUAU

UUAUUAUUAUUAUUAUU (SEQ ID NO: 392)

UUCAUCUUAAAGGCUCCGCUUCUGCU (SEQ ID NO: 393)

UUCAUUUUGUAUCCCCUGCUUUUGCU (SEQ ID NO: 394)

UUCCAUUCUGAAUCAGUACCUGCUUUUGCU (SEQ ID NO: 395)

UUCCAUUUCGAAUCAGUACCUGCUUUCGCU (SEQ ID NO: 396)

UUCCAUUUCGGAUCAGUACCUGCUUUUGCU (SEQ ID NO: 397)

UUCCAUUUUGAAUCAGUACCUGCUUUUGCU (SEQ ID NO: 398)

UUCCAUUUUGGAUCAGUACCUGCUUUCGCU (SEQ ID NO: 399)

UUCCAUUUUGGAUCAGUACCUGCUUUUGCU (SEQ ID NO: 400)

UUCCCAAGCAAGUCUCUUCUCUUGUUGGU (SEQ ID NO: 401)

UUCCCAGACAAGUUUCUUCUCUUGUUGGU (SEQ ID NO: 402)

UUCCCCUUGG (SEQ ID NO: 403)

UUCCCCUUGUUCGGU (SEQ ID NO: 404)

UUCCUCUUGUUUGGU (SEQ ID NO: 405)

UUCGCG

UUCGCUGCUUUCGCU (SEQ ID NO: 406)

UUCUAAGAAUAUGCUCUGCUUCUGCU (SEQ ID NO: 407)

UUCUCUGUCCAUCGCUUGUUUUUGCU (SEQ ID NO: 408)

UUCUUUCUUUUUGUGUGCCC (SEQ ID NO: 409)

UUGAACUAUCCUUACCCAACUUUGUUGGU (SEQ ID NO: 410)

UUGAAUAUAAUUGACCUGCUUUCGCU (SEQ ID NO: 411)

UUGAUCUAUCCUUACCCAACUUUGUUGGU (SEQ ID NO: 412)

UUGAUCUGGUUGUUAAGCGU (SEQ ID NO: 413)

UUGCCUGCUUUCGCU (SEQ ID NO: 414)

UUGCCUGCUUUUGCU (SEQ ID NO: 415)

UUGGAUUCAUUUUAAUCUCCUGCUUUUGCU (SEQ ID NO: 416)

UUGGUUUUGUUGUUAAGCGU (SEQ ID NO: 417)

UUGU

UUGUACGCAUUUUUUCCCGU (SEQ ID NO: 418)

UUGUACGCAUUUUUUCGCGU (SEQ ID NO: 419)

UUGUAUUAGGAAUGGUUUUUUUGUCUUCGU (SEQ ID NO: 420)

UGUAUUCAUUUUAAACCCCUGCUUUUGCU (SEQ ID NO: 421)

UUGUAUUCAUUUUAAACUCCUGCUUUUGCU (SEQ ID NO: 422)

UUGUCAUAUAAUUGGUUUUUUUGUCUUCGU (SEQ ID NO: 423)

UUGUCUUCGU (SEQ ID NO: 424)

UUGUG rU*rU*rG*rU*rG*rG*rG*rG*rG

UUGUGGGUCA (SEQ ID NO: 425)

UUGUGU

UUGUGUGCCC (SEQ ID NO: 426)

UUGUGUGUCU (SEQ ID NO: 427)

UUGUGUUUGGAGCGCCUGUUUUUGCU (SEQ ID NO: 428)

UUGUUGU

UUGUUGUUGUUGUUGUUGUU (SEQ ID NO: 429)

UUGUUGUUUUGUUGUUUUGUUGUU (SEQ ID NO: 430)

UUGUUGUUUUUGGUGGUUGUUG (SEQ ID NO: 431)

UUGUUUAGAAAUCCCCUGCUUCUGCU (SEQ ID NO: 432)

UUGUUUUUGUGUGUC (SEQ ID NO: 433)

UUNUUNUUNUUNUUNUNUNUU (SEQ ID NO: 434)

UUUAAACCCCUGCUUUUGCU (SEQ ID NO: 435)

UUUAAACUCCUGCUUUUGCU (SEQ ID NO: 436)

UUUAACUAUCCUUAGCCAACUUUGUCUGGU (SEQ ID NO: 437)

UUUAAUCUCCUGCUUUUGCU (SEQ ID NO: 438)

UUUAUCUAUCCAUAGCCAACUUUUUCUGGU (SEQ ID NO: 439)

UUUAUCUAUCCUUAGCCAACUUUGUCUGGU (SEQ ID NO: 440)

UUUAUGAUAC (SEQ ID NO: 441)

UUUAUUUAUUUAUUUAUUUA (SEQ ID NO: 442)

UUUAUUUGUCUUCGU (SEQ ID NO: 443)

UUUCCAAACAAGUCUCUUCUCUUGUUUGGU (SEQ ID NO: 444)

UUUCUCUUGUCUGGU (SEQ ID NO: 445)

UUUCUCUUGUUUGGU (SEQ ID NO: 446)

UUUCUUAUAC (SEQ ID NO: 447)

UUUGGAAAAGUACCCCUGCUUCUGCU (SEQ ID NO: 448)

UUUGUCUGGU (SEQ ID NO: 449)

UUUGUGU (SEQ ID NO: 450)

UUUGUGUGUC (SEQ ID NO: 451)

UUUGUGUGUCUCUCUUGUUUUUGUGUGUCU (SEQ ID NO: 452)

UUUGUUGUUAAGCGU (SEQ ID NO: 453)

UUUGUUUGGU (SEQ ID NO: 454)

UUUGUUUGUCUUCGU (SEQ ID NO: 455)

UUUGUUUGUUUGUUUGUUUG (SEQ ID NO: 456)

UUUGUUUUUCUCCGU (SEQ ID NO: 457)

UUUGUUUUUCUUCGU (SEQ ID NO: 458)

UUUGUUUUUUCUCGU (SEQ ID NO: 459)

UUUU (SEQ ID NO: 460)

UUUUAUUUAUUUAUUUA (SEQ ID NO: 461)

UUUUCCCUGCUUUUGCUAA

UUUUCGCG

UUUUCGGCGCGCGCCG

UUUUCGGCGGCCGCCG (SEQ ID NO: 462)

UUUUCUCCGU (SEQ ID NO: 463)

UUUUCUUCGU (SEQ ID NO: 464)

UUUUGGGG

UUUUGGGGG rU*rU*rU*rU*rU*rG*rG*rG*rG*rG

UUUUGUUUGUUUGUUUG (SEQ ID NO: 465)

UUUUU

UUUUUCCCGU (SEQ ID NO: 466)

UUUUUCGCGU (SEQ ID NO: 467)

UUUUUCUCGU (SEQ ID NO: 468)

UUUUUCUGGU (SEQ ID NO: 469)

UUUUUCUUUUGUGUGUCCG (SEQ ID NO: 470)

UUUUUGAUAC (SEQ ID NO: 471)

UUUUUGGGGG (SEQ ID NO: 472)

UUUUUGU

UUUUUU

UUUUUUAUAC (SEQ ID NO: 473)

UUUUUUCGGCGGCCGCCG (SEQ ID NO: 474)

UUUUUUGGGGG (SEQ ID NO: 475)

UUUUUUGUUAAGCGU (SEQ ID NO: 476)

UUUUUUU rU*rU*rU*rU*rU*rU*rU

UUUUUUUGUCUUCGU (SEQ ID NO: 477)

UUUUUUUU

UUUUUUUUU

UUUUUUUUUU (SEQ ID NO: 478)

wherein A, C, G, T, and U have their usual meanings and refer to ribonucleotides (except when preceded by "d" to indicate deoxynucleotide), Acr represents acridine; B represents C, G, T, or U (not A); BIOT represents biotin; CHOL represents cholesterol; E represents 7-deaza-rG; FAM represents fluorescein; HEX represents hexadecyl glycerol; mA represents 2'-O-methyl adenosine; mC represents 2'-O-methyl cytidine; mG represents 2'-O-methyl guanosine; mU represents 2'-O- methyl uridine; N represents A, C, G, U, T, or I (inosine); TEG represents triethylene glycol; "-" between nucleotides represents phosphodiester linkage; and "*" between nucleotides represents phosphorothioate linkage.

Exemplary sequences of ORN of the invention also include but are not limited to the following, wherein A, C, G, T, and U have their usual meanings and refer to ribonucleotides:

ACGCGAAAAAAACGCGTATAAATTAAGTTA (SEQ ID NO: 479)

ATTGAAGAGTTTGATCATGGCTCAGATTGAACG (SEQ ID NO: 480)

CACCTCTCATGCTCTGCTCTCTTC (SEQ ID NO: 481)

CAGAGCUUUGGAGUCAGCATT (SEQ ID NO: 482)

CTGCGCTGCTGCAAGTTACGGAATG (SEQ ID NO: 483)

CUGGACUUCCAGAAGAACATT (SEQ ID NO: 484)

GCGCGAAATCATGACTTAACGTCAG (SEQ ID NO: 485)

GCTAGACCGTTTCCTTGAACACCTG (SEQ ID NO: 486)

GGGGGACGATCGTCGGGGG (SEQ ID NO: 487)

GTATCAAAAAGATGATGATACTTGGAAGA (SEQ ID NO: 488)

GUGUGUGUTTTTTT (SEQ ID NO: 489)

GUUGUGUACGGCGCCGTGCCG (SEQ ID NO: 490)

TAAGGAGGTGATCCAACCGCAGGTTCC (SEQ ID NO: 491)

TCCATGACGTTCCTGATGCT (SEQ ID NO: 492)

TCGTCGTTT

TCGTCGTTTGUUGUGUAAT (SEQ ID NO: 493)

TCGTCGTTTT (SEQ ID NO: 494)

T*C*G*T*C*G*T*T*T*T*C*G*G*C*G*C*G*C*G (SEQ ID NO: 495)

TCGTCGTTTTCGGCGGCCGCCG (SEQ ID NO: 496)

TCGTCGTTTTGTCGTTTTGTCGTT (SEQ ID NO: 497)

TCGTCGTTTTGUUGUUUUGUUGUU (SEQ ID NO: 498)

TCGTCGTTTTCGGTCGTTTT (SEQ ID NO: 499)

TCGTCGTTTTUGGUGGUUGUUG (SEQ ID NO: 500)

TTTTTGUGUGUGU (SEQ ID NO: 501)

TUGTUGTTTTGTUGTTTTGTUGTT (SEQ ID NO: 502)

TUGTUGTTTTUGGUGGUUGUUG (SEQ ID NO: 503)

UGCUGACUCCAAAGCUCUGTT (SEQ ID NO: 504)

UGUUCUUCUGGAAGUCCAGT (SEQ ID NO: 505)

In one embodiment the invention can exclude any one or more of the foregoing exemplary sequences of ORN.

ORN of the invention in one embodiment include at least one modified internucleoside linkage. In one embodiment the at least one internucleoside linkage does not occur within or immediately adjacent to an immunostimulatory RNA sequence motif. In one embodiment a modified internucleoside linkage is a stabilized internucleoside linkage. A stabilized internucleoside linkage is relatively resistant, compared to a phosphodiester internucleoside linkage, to nuclease digestion under physiologic conditions.

In one embodiment a modified internucleoside linkage is a phosphorothioate linkage.

In one embodiment a modified internucleoside linkage is a phosphorodithioate linkage.

In yet other embodiments a modified internucleoside linkage can be methylphosphonate, other alkylphosphonate, arylphosphonate, methylphosphorothioate, other alkylphosphorothioate, arylphosphorothioate, p-ethoxy, other p-alkyloxy, and morpholino. This list is not meant to be limiting.

Any combination of modified and unmodified (i.e., phosphodiester) internucleoside linkages within an ORN is contemplated by the invention.

Modified backbones such as phosphorothioates may be synthesized using automated techniques employing either phosphoramidate or H-phosphonate chemistries. Aryl- and alkyl-phosphonates can be made, e.g., as described in U.S. Pat. No. 4,469,863; and alkylphosphotriesters (in which the charged oxygen moiety is alkylated as described in U.S. Pat. No. 5,023,243 and European Pat. No. 092,574) can be prepared by automated solid phase synthesis using commercially available reagents. Methods for making other backbone modifications and substitutions have been described. Uhlmann E et al. (1990) *Chem Rev* 90:544; Goodchild J (1990) *Bioconjugate Chem* 1:165.

ORN of the invention also encompass ORN having unusual internucleotide linkages, including specifically 5'-5', 3'-3',2'-2', 2'-3', and 2'-5' internucleotide linkages. In one embodiment such unusual linkages are excluded from the immunostimulatory RNA motif, even though one or more of such linkages may occur elsewhere within the polymer. For polymers having free ends, inclusion of one 3'-3' internucleotide linkage can result in a polymer having two free 5' ends. Conversely, for polymers having free ends, inclusion of one 5'-5' internucleotide linkage can result in a polymer having two free 3' ends.

ORN of the invention can contain two or more ORN which can be linked through a branching unit. The internucleotide linkages can be 3'-5', 5'-5',3'-3', 2'-2',2'-3', or 2'-5' linkages. Thereby, the nomenclature 2'-5' is chosen according to the carbon atom of ribose. However, if unnatural sugar moieties are employed, such as ring-expanded sugar analogs (e.g., hexanose, cyclohexene or pyranose) or bi- or tricyclic sugar analogs, then this nomenclature changes according to the nomenclature of the monomer. The unusual internucleotide linkage can be a phosphodiester linkage, but it can alternatively be modified as phosphorothioate or any other modified linkage as described herein. The structure below shows a general structure for branched RNA oligomers and modified oligoribonucleotide analogs of the invention via a nucleotidic branching unit. Thereby $Nu_1$, $Nu_2$, and $Nu_3$ can be linked through 3'-5', 5'-5',3'-3', 2'-2',2'-3', or 2'-5'-linkages. Branching of RNA oligomers can also involve the use of non-nucleotidic linkers and abasic spacers. In one embodiment, $Nu_1$, $Nu_2$, and $Nu_3$ represent identical or different immunostimulatory RNA motifs. In another embodiment, $Nu_1$, $Nu_2$, and $Nu_3$ comprises at least one immunostimulatory RNA motif and at least one immunostimulatory CpG DNA motif.

The ORN may contain a doubler or trebler unit (Glen Research, Sterling, Va.), in particular those modified oligoribonucleotide analogs with a 3'-3' linkage. A doubler unit in one embodiment can be based on 1,3-bis-[5-(4,4'-dimethoxytrityloxy)pentylamido]propyl-2-[(2-cyanoethyl)-(N,N-diisopropyl)]-phosphoramidite. A trebler unit in one embodiment can be based on incorporation of Tris-2,2,2-[3-(4,4'-dimethoxytrityloxy)propyloxymethyl]ethyl-[(2-cyanoethyl)-(N,N-diisopropyl)]-phosphoramidite.

Branching of the modified oligoribonucleotide analogs by multiple doubler, trebler, or other multiplier units leads to dendrimers which are a further embodiment of this invention. Branched modified oligoribonucleotide analogs may lead to crosslinking of receptors for immunostimulatory RNA such as TLR3, TLR7, and TLR8, with distinct immune effects compared to non-branched forms of the analogs. In addition, the synthesis of branched or otherwise multimeric analogs may stabilize RNA against degradation and may enable weak or partially effective RNA sequences to exert a therapeutically useful level of immune activity. The modified oligoribonucleotide analogs may also contain linker units resulting from peptide modifying reagents or oligonucleotide modifying reagents (Glen Research). Furthermore, the modified oligoribonucleotide analogs may contain one or more natural or unnatural amino acid residues which are connected to the polymer by peptide (amide) linkages.

The 3'-5', 5'-5',3'-3', 2'-2',2'-3', and 2'-5' internucleotide linkages can be direct or indirect. Direct linkages in this context refers to a phosphate or modified phosphate linkage as disclosed herein, without an intervening linker moiety. An intervening linker moiety is an organic moiety which can include, for example, polyethylene glycol, triethylene glycol, hexaethylene glycol, abasic nucleotide, doubler unit, or trebler unit. The intervening linker can in one embodiment contain an additional phosphate or modified phosphate group. The intervening linker in one embodiment does not contain an additional phosphate or modified phosphate group.

The ORN of the invention in one embodiment can include at least one modified sugar residue. In one embodiment the modified sugar residue is selected from α-arabinofuranose, α-D-ribose, β-D-xylo-furanose, α-L-ribose, 2'-[O—($C_1$-$C_6$) alkyl-O—($C_1$-$C_6$)alkyl]ribose, 2'-amino-2'-deoxyribose, 2'-fluoro arabinofuranose, 2'-fluoro-2'-deoxyribose, 2'-O—($C_1$-$C_6$)alkyl-ribose, 2'-O—($C_2$-$C_6$)alkenyl-ribose, 2'-O,4'-C-methylene-bridged ribose (locked nucleic acid, LNA), 2'-O,4'-C-ethylene-bridged ribose (ENA), and β-L-ribose. In respect of LNA and ENA, see, for example U.S. Pat. Nos. 6,268,790 and 6,770,748 and Koizumi M et al. (2003) *Nucleic Acids Res* 31:3267-73, respectively.

In certain embodiments at least one β-ribose unit may be replaced by carbocyclic and/or open-chain sugar analogs (described, for example, in Vandendriessche et al. (1993) *Tetrahedron* 49:7223) and/or bicyclosugar analogs (described, for example, in Tarkov M et al. (1993) *Helv Chim Acta* 76:481).

ORN in which at least one ribose unit is replaced by 1,5-anhydrohexitol (Bouvere B et al. (1997) *Nucleosides Nucleotides* 16:973-6) or by D-Altritol (Allart B et al. (1999) *Chemistry—A European Journal* 5:2424-31) are also embodiments of this invention. In another embodiment, the ORN comprises at least one □-D-ribopyranosyl unit ("pyranosyl-RNA"). Pitsch S et al. (2003) *Helv Chim Acta* 86:4270-363. Alternatively, other ring-expanded or ring-condensed sugar analogs may replace ribose.

In another embodiment, at least one hydroxy group, preferably the 2'-hydroxy group, of the ribose unit is protected as a pro-drug, which is cleaved in vivo to release the ORN with unprotected ribose. Known pro-drugs of ribose are e.g. the corresponding valinates (Kong L et al. (2003) *Antivir Chem Chemother* 14:263-70), formates (Repta A et al. (1975) *J Pharm Sci* 64:392-6), or isopropyl ethers (Winkelmann E et al. (1988) *Arzneimiffelforschung* 38:1545-8).

ORN of the invention can include at least one modified nucleobase. In one embodiment a modified nucleobase is selected from the group consisting of 2,6-diaminopurine, 2-amino-6-chloropurine, 2-aminopurine, 2-thiouracil, 4-thiouracil, 5-($C_1$-$C_6$)-alkylcytosine, 5-($C_1$-$C_6$)-alkyluracil, 5-($C_2$-$C_6$)-alkenylcytosine, 5-($C_2$-$C_6$)-alkenyluracil, 5-($C_2$-$C_6$)-alkynylcytosine, 5-($C_2$-$C_6$)-alkynyluracil, 5-(hydroxymethyl)uracil, 5-aminouracil, 5-bromocytosine, 5-bromouracil, 5-chlorocytosine, 5-chlorouracil, 5-fluorocytosine, 5-fluorouracil, 5-iodouracil, 5-hydroxycytosine, 5-methylcytosine, 5-methyluracil, N4-ethylcytosine, 6-thioguanine, 7-deaza-7-($C_2$-$C_6$)alkynylguanine, 7-deaza-7-substituted guanine, 7-deaza-7-substituted purine, 7-deaza-8-substituted guanine, 7-deaza-8-substituted purine, 7-deazaguanine, 8-azaguanine, 8-azapurine, 8-hydroxyguanine, 8-hydroxyadenine, dihydrouracil, hydrogen (abasic nucleotide), hypoxanthine, $N^2$-dimethylguanine, pseudouracil, and substituted 7-deazapurine. In one embodiment a modified nucleobase is excluded from an immunostimulatory RNA sequence motif.

In one embodiment the ORN includes at least one abasic nucleotide. An "abasic nucleotide" as used herein refers to a nucleotide in which a hydrogen atom is substituted for the heterocyclic nucleobase.

In certain embodiments the ORN is covalently linked to a lipophilic moiety. The lipophilic moiety generally will occur at a 3' end, although in certain embodiments the lipophilic moiety can occur elsewhere along the ORN. In one embodiment the ORN has a 3' end and the lipophilic moiety is covalently linked to the 3' end. The lipophilic group in general can be a cholesteryl, a modified cholesteryl, a cholesterol derivative, a reduced cholesterol, a substituted cholesterol, cholestan, $C_{1-6}$ alkyl chain, $C_{1-8}$ alkyl chain, a bile acid, cholic acid, taurocholic acid, deoxycholate, oleyl litocholic acid, oleoyl cholenic acid, a glycolipid, a phospholipid, a sphingolipid, an isoprenoid, such as steroids, vitamins, such as vitamin E (tocopherol), saturated fatty acids, unsaturated fatty acids, fatty acid esters, such as triglycerides, pyrenes, porphyrines, Texaphyrine, adamantane, acridines, biotin, coumarin, fluorescein, rhodamine, Texas-Red, digoxygenin, dimethoxytrityl, t-butyldimethylsilyl, t-butyldiphenylsilyl, cyanine dyes (e.g. Cy3 or Cy5), Hoechst 33258 dye, psoralen, or ibuprofen. In certain embodiments the lipophilic moiety is chosen from cholesteryl, palmityl, and fatty acyl. In one embodiment the lipohilic moiety is cholesteryl. It is believed that inclusion of one or more of such lipophilic moieties in the ORN of the invention confers upon them yet additional stability against degradation by nucleases, as well as improved cellular uptake. Where there are two or more lipophilic moieties in a single ORN of the invention, each lipophilic moiety can be selected independently of any other.

In one embodiment the lipophilic group is attached to a 2'-position of a nucleotide or nucleotide analog of the ORN. A lipophilic group can alternatively or in addition be linked to the heterocyclic nucleobase of a nucleotide or nucleotide analog of the ORN. The lipophilic moiety can be covalently linked to the ORN via any suitable direct or indirect linkage. In one embodiment the linkage is direct and is an ester or an amide. In one embodiment the linkage is indirect and includes a spacer moiety, for example one or more abasic nucleotide residues, oligoethyleneglycol, such as triethyleneglycol (spacer 9) or hexaethyleneglycol (spacer 18), or an alkanediol, such as butanediol.

In one embodiment the ORN of the invention is advantageously combined with a cationic lipid. Cationic lipids are believed to assist in trafficking of the ORN into cells, either to the endosomal compartment, where TLR7 and TLR8 (as well as TLR9) are found, or to the cytosol, where RIG-I is found. In one embodiment the cationic lipid is DOTAP methosulfate (N-(2,3-dioleoyloxy)-1-propyl)-N,N,N-trimethylammonium methyl sulfate). In one embodiment the cationic lipid is DOTAP chloride (N-[1-(2,3-dioleoyloxy)propyl]-N,N,N-trimethylammonium chloride). Although DOTAP appears to deliver the ORNs preferentially to the endosomal compartment, part of the ORN will also be delivered to the cytosol. Other delivery agents, such as lipofectin, lipofectamine, and cellfectin appear to deliver the ORN more effectively to the cytosol than does DOTAP. Assuming that the ORN has appropriate motifs to stimulate TLR7/8, and depending on the ratio of ORN delivered to the endosomal compartment to ORN delivered to the cytosol, ORN of the invention can preferentially activate TLR7/8 or RIG-I, respectively.

As used herein, "TLR7/8" shall refer to TLR7 alone, TLR8 alone, or both TLR7 and TLR8.

In certain aspects the invention further provides a pharmaceutical composition containing, as an active ingredient, at least one ORN of the invention, or a pharmaceutically acceptable salt thereof, and a pharmaceutically acceptable carrier.

The pharmaceutical compositions according the invention include a pharmaceutically acceptable carrier. Pharmaceutical compositions of the invention contain an effective amount of active ingredient and optionally other therapeutic agents included in a pharmaceutically acceptable carrier. The term "pharmaceutically acceptable carrier" means one or more compatible solid or liquid filler, diluents or encapsulating substances which are suitable for administration to a human or other vertebrate animal. The term "carrier" denotes an organic or inorganic ingredient, natural or synthetic, with which the active ingredient is combined to facilitate the application. The components of the pharmaceutical compositions are capable of being commingled with each other in a manner such that there is no interaction which would substantially impair the desired pharmaceutical efficacy.

The invention further contemplates methods for the manufacture of the pharmaceutical compositions of the invention. Such methods include the step of placing an amount of active ingredient of the pharmaceutical composition of the invention in a pharmaceutically acceptable carrier. The methods for manufacture of the pharmaceutical compositions of the invention can further include a step or steps that involve shaping or formulating the pharmaceutical composition for a particular route of administration, such as is described elsewhere herein.

In one embodiment the pharmaceutical composition of the invention further includes an antigen. An "antigen" as used herein refers to a molecule capable of provoking an adaptive immune response specific for the antigen. An antigen is thus distinct from a TLR agonist or an adjuvant as used herein, although a TLR agonist or adjuvant can boost an adaptive immune response to an antigen.

Antigens include but are not limited to cells, cell extracts, proteins, polypeptides, peptides, polysaccharides, polysaccharide conjugates, peptide and non-peptide mimics of polysaccharides and other molecules, small molecules, lipids, glycolipids, carbohydrates, viruses and viral extracts, multicellular organisms such as parasites, and allergens.

The term "antigen" can encompass allergens, cancer antigens, microbial antigens, and, in the context of autoimmunity, autoantigens (i.e., inappropriate self-antigens).

Allergens are discussed below.

A "cancer antigen" as used herein is a compound, such as a peptide or protein, associated with a tumor or cancer cell surface and which is capable of provoking an immune response when expressed on the surface of an antigen-presenting cell (APC) in the context of a major histocompatibility complex (MHC) molecule. Some of these antigens are encoded, although not necessarily expressed, by normal cells. These antigens can be characterized as those which are normally silent (i.e., not expressed) in normal cells, those that are expressed only at certain stages of differentiation and those that are temporally expressed such as embryonic and fetal antigens. Other cancer antigens are encoded by mutant cellular genes, such as oncogenes (e.g., activated ras oncogene), suppressor genes (e.g., mutant p53), fusion proteins resulting from internal deletions or chromosomal translocations. Still other cancer antigens can be encoded by viral genes such as those carried on RNA and DNA tumor viruses.

Cancer antigens can be prepared from cancer cells either by preparing crude extracts of cancer cells, for example, as described in Cohen et al. (1994) *Cancer Research,* 54:1055, by partially purifying the antigens, by recombinant technology, or by de novo synthesis of known antigens. Cancer antigens include but are not limited to antigens that are recombinantly expressed, an immunogenic portion of, or a whole tumor or cancer. Such antigens can be isolated or prepared recombinantly or by any other means known in the art.

Examples of cancer antigens include MAGE, MART-1/Melan-A, gp100, dipeptidyl peptidase IV (DPPIV), adenosine deaminase-binding protein (ADAbp), cyclophilin b, colorectal associated antigen (CRC)—0017-1A/GA733, carcinoembryonic antigen (CEA) and its immunogenic epitopes CAP-1 and CAP-2, etv6, aml1, prostate specific antigen (PSA) and its immunogenic epitopes PSA-1, PSA-2, and PSA-3, prostate-specific membrane antigen (PSMA), T-cell receptor/CD3-zeta chain, MAGE-family of tumor antigens (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-05), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p21 ras, RCAS1, α-fetoprotein, E-cadherin, α-catenin, β-catenin, γ-catenin, p120ctn, gp100$^{Pmel117}$, PRAME, NY-ESO-1, cdc27, adenomatous polyposis coli protein (APC), fodrin, Connexin 37, Ig-idiotype, p15, gp75, GM2 and GD2 gangliosides, viral products such as human papillomavirus proteins, Smad family of tumor antigens, Imp-1, P1A, EBV-encoded nuclear antigen (EBNA)-1, brain glycogen phosphorylase, SSX-1, SSX-2 (HOM-MEL-40), SSX-1, SSX-4, SSX-5, SCP-1, CT-7, and c-erbB-2. This list is not meant to be limiting.

Cancers associated with specific cancer antigens include, for example, acute lymphoblastic leukemia (etv6; aml1; cyclophilin b); B cell lymphoma (Ig-idiotype); glioma (E-cadherin; α-catenin; β-catenin; γ-catenin; p120ctn); bladder cancer (p21 ras); biliary cancer (p21 ras); breast cancer (MUC family; HER2/neu; c-erbB-2); cervical carcinoma (p53; p21 ras); colon carcinoma (p21 ras; HER2/neu; c-erbB-2; MUC family); colorectal cancer (C017-1A/GA733; APC); choriocarcinoma (CEA); epithelial cell cancer (cyclophilin b); gastric cancer (HER2/neu; c-erbB-2; ga733 glycoprotein); hepatocellular cancer (α-fetoprotein); Hodgkins lymphoma (Imp-1; EBNA-1); lung cancer (CEA; MAGE-3; NY-ESO-1); lymphoid cell-derived leukemia (cyclophilin b); melanoma (Melan-A/MART-1; cdc27; MAGE-3; p21ras; gp100$^{Pmel117}$; p15 protein; gp75; oncofetal antigen; GM2 amd GD2 gangliosides); myeloma (MUC family; p21 ras); non-small cell lung carcinoma (HER2/neu; c-erbB-2); nasopharyngeal cancer (Imp-1; EBNA-1); ovarian cancer (MUC family; HER2/neu; c-erbB-2); prostate cancer (prostate specific antigen (PSA) and its immunogenic epitopes PSA-1, PSA-2, and PSA-3; PSMA; HER2/neu; c-erbB-2); pancreatic cancer (p21 ras; MUC family; HER2/neu; c-erbB-2; ga733 glycoprotein); renal cell carcinoma (HER2/neu; c-erbB-2); squamous cell cancers of cervix and esophagus (viral products such as human papillomavirus proteins); testicular cancer (NY-ESO-1); and T cell leukemia (HTLV-1 epitopes).

A "microbial antigen" as used herein is an antigen of a microorganism and includes but is not limited to viral antigens, bacterial antigens, parasite antigens, and fungal antigens. Such antigens include the intact microorganism as well as natural isolates and fragments or derivatives thereof and also synthetic compounds which are identical to or similar to natural microorganism antigens and induce an immune response specific for that microorganism. A compound is similar to a natural microorganism antigen if it induces an immune response (humoral and/or cellular) to a natural microorganism antigen. Such antigens are used routinely in the art and are well known to those of ordinary skill in the art.

Examples of bacterial antigens are well known in the art and include immunogenic components of vaccines directed against specific bacteria, e.g., diphtheria, *Mycobacterium tuberculosis*. Examples of viral antigens are well known in the art and include immunogenic components of vaccines directed against specific viruses, e.g., hepatitis B virus, measles (rubeola) virus, German measles (rubella) virus, mumps virus, polio virus.

The invention in some aspects relates to methods of use of ORN of the invention, and similarly pharmaceutical compositions of the invention, to modulate an immune response in a subject. In certain aspects the invention provides methods of enhancing an immune response in a subject. As used herein, "enhancing an immune response in a subject" refers in one embodiment to inducing an immune response in a subject. As used herein, "enhancing an immune response in a subject" refers in one embodiment to augmenting an immune response in a subject. Thus enhancing an immune response according to methods of the invention results in a more robust immune response than would normally occur, e.g., apart from the methods of the invention.

As used herein, the term "immune response" refers to any aspect of an innate or adaptive immune response that reflects activation of an immune cell or population of immune cells to proliferate, to perform an effector immune function, or to produce one or more gene products involved in an immune response. An "immune cell" as used herein refers to any bone marrow-derived cell that can participate in an innate or adaptive immune response. Cells of the immune system include, without limitation, dendritic cells (DC), natural killer (NK) cells, monocytes, macrophages, granulocytes, B lymphocytes, plasma cells, T lymphocytes, and precursor cells thereof. In one embodiment an immune cell is a TLR7-expressing immune cell. In one embodiment an immune cell is a TLR8-expressing immune cell. In one embodiment an immune cell is a RIG-I-expressing immune cell. Since RIG-I appears to be expressed in the cytoplasm of many cells and its expression can be induced by, e.g., dsRNA, IFN-γ, and IL-1β, its activation by ORN having a 5'-triphosphate or 5'-triphosphate analog is not limited to the immune cells mentioned above. Furthermore, the ORN with a 5'-triphosphate or 5'-triphosphate analog can have in addition a nucleotide motif for TLR7/8 which allows activation of both TLR7/8 and RIG-I. It is conceivable that activation of TLR7/8 through the immune stimulating RNA motif can trigger increased expression of RIG-I, which in turn can be activated by the ORN 5'-triphosphate or 5'-triphosphate analog, leading to strong induction of cytokines. Gene products involved in an immune response can include secreted products (e.g., antibodies, cytokines, and chemokines) as well as intracellular and cell surface molecules characteristic of immune function (e.g., certain cluster of differentiation (CD) antigens, transcription factors, and gene transcripts). The term "immune response" can be applied to a single cell or to a population of cells.

Antibodies are well known in the art and generally include antibodies of any of the various classes (isotypes) IgG, IgA, IgM, IgE, and IgD, as well as their subclasses (e.g., IgG1, IgG2, etc.).

Cytokines are well known in the art and generally include interferons, interleukins, tumor necrosis factor (TNF), transforming growth factor beta (TGF-β), and chemokines. Interferons are well known in the art and generally include but are not limited to IFN-α, IFN-β, IFN-γ. Interleukins are well known in the art and generally include but are not limited to IL-1, IL-2, IL-4, IL-5, IL-6, IL-10, IL-12, IL-13, IL-15, and IL-18. Chemokines are well known in the art and generally include but are not limited to RANTES, MIP-1α, MIP-1β, and IP-10, to name but a few.

Production of cytokines can be assessed by any of several methods well known in the art, including biological response assays, enzyme-linked immunosorbent assay (ELISA), intracellular fluorescence-activated cell sorting (FACS) analysis, and reverse transcriptase/polymerase chain reaction (RT-PCR).

In one embodiment the immune response involves upregulation of cell surface markers of immune cell activation, such as CD25, CD80, CD86, and CD154. Methods for measuring cell surface expression of such markers are well known in the art and include FACS analysis.

The compound or pharmaceutical composition is administered to a subject in an effective amount. As used herein, "administering" refers to administering, either alone or in combination with at least one other agent, by any suitable route of administration. In one embodiment the administering is systemic administration, for example by enteral or parenteral administration. Enteral administration includes but is not limited to oral administration. Parenteral administration includes but is not limited to intravenous (i.v.), intramuscular (i.m.), intraperitoneal (i.p.), intranasal (i.n.), subcutaneous (s.c.), inhalational, mucosal, and topical administration. In one embodiment the administering is local administration. Local administration includes but is not limited to direct injection into a site to be treated, e.g., intralesional.

A "subject" as used herein refers to a mammal. In one embodiment a subject is a human. In one embodiment a subject is a non-human mammal, e.g., a mouse, rat, hamster, guinea pig, rabbit, cat, dog, pig, sheep, goat, horse, cow, monkey or other non-human primate.

As used herein, an "effective amount" is an amount that is sufficient to achieve a desired biological effect. Thus in one embodiment an effective amount is an amount sufficient to enhance an immune response in a subject. The effective amount for any particular application can vary depending on any of a number of factors, discussed in further detail below.

In one embodiment an immune response involves production of IFN-α. IFN-α was the first interferon to be identified and commercialized. It encompasses a family of about twenty structurally related proteins each encoded by a separate gene. IFN-α is generally secreted in large part by mononuclear phagocytes and so-called interferon producing cells (IPCs) recently identified as plasmacytoid dendritic cells (pDCs). Measurement of secreted IFN-α can be accomplished, for example, using subtype-specific or subtype-nonspecific IFN-α-specific ELISA. Major effects of IFN-α include inhibition of viral replication, inhibition of cell proliferation, activation of natural killer (NK) cell lytic functions, and upregulation of class I major histocompatibility complex (MHC). IFN-α has been reported to be useful in the treatment of a variety of diseases including certain malignancies (e.g., hairy cell leukemia, cutaneous T cell leukemia, chronic myeloid leukemia, non-Hodgkins lymphoma, AIDS-related Kaposi's sarcoma, malignant melanoma, multiple myeloma, renal cell carcinoma, bladder cell carcinoma, colon carcinoma, cervical dysplasia) and viral diseases (e.g., chronic hepatitis B, chronic hepatitis C, genital warts (papillomavirus)). Various recombinant forms of IFN-α are commercially available, including ROFERON®-A (IFN-α2a, Roche) and INTRON® A (IFN-α2b; Schering).

In one embodiment an immune response involves production of IL-12. IL-12 is a principal mediator of the early innate immune response to intracellular microbes and is a key inducer of cell-mediated immunity, the adaptive immune response to these microbes. IL-12 is responsible primarily for the induction of interferon gamma (IFN-γ) and tumor necrosis factor-alpha (TNF-α) from both NK cells and helper T cells. IL-12 also stimulates the rate at which NK cells and helper T cells proliferate following antigen activation. In addition, the lytic capacities of both NK and CD8$^+$ cytolytic T cells are increased by the presence of IL-12. IL-12 has the specialized function of directing naive CD4+T cells to differentiate toward the T helper 1 (Th1) phenotype in order to prepare for the release of IFN-γ and for the development of the cell-mediated immune response. Hsieh C S et al. (1993) Science 260:547-9.

In one embodiment an immune response enhanced according to a method of the invention is a Th1-type immune response. As used herein, a "Th1-type immune response" refers to an immune response with a predominantly Th1 character. Such an immune response is characterized by the presence of at least one of the following: IFN-γ, IL-12, IL-18, IgG1 (human) or IgG2a (mice), and cell-mediated immunity. A Th1-type immune response in one embodiment is a Th1 immune response. In contrast, a Th2-type immune response is characterized by at least one of the following: IL-4, IL-5, IL-13, IgE, and humoral immunity. It is recognized in the art that Th1 and Th2 immune responses are counter-regulatory, such that a Th1 immune response down-regulates a Th2 immune response, and a Th2 immune response down-regulates a Th1 immune response. The pharmaceutical compositions and methods of the invention thus are particularly useful whenever it is desirable to promote a Th1-type immune response or to inhibit a Th2-like immune response.

In one embodiment the subject being treated has immune suppression. Immune suppression is an undesirably weak or absent ability to mount an effective immune response to a suitable immune stimulus. Various factors and conditions are related to immune suppression, including congenital and acquired immunodeficiencies. Congenital immunodeficiencies include various forms of severe combined immunodeficiency (SCIDs), adenosine deaminase (ADA) deficiency, purine nucleoside phosphorylase (PNP) deficiency, X-linked agammaglobulinemia, Ig heavy chain deletions, DiGeorge syndrome, selective Ig isotype deficiencies, X-linked hyper-IgM syndrome, common variable immunodeficiency, X-linked lymphoproliferative syndrome, bare lymphocyte syndrome, transporter associated with antigen processing (TAP) deficiency, Wiskott-Aldrich syndrome, ataxia-telangiectasia, chronic granulomatous disease, leukocyte adhesion deficiency-1, leukocyte deficiency-2, and Chédiak-Higashi syndrome. This list is not meant to be limiting. Acquired immunodeficiencies include those related to human immunodeficiency virus (HIV) infection, protein-calorie malnutrition, burns, cancer, bone marrow transplantation, anti-rejection immunosuppressive drugs, other drugs, chemotherapy, and irradiation.

In one embodiment the subject being treated has immune suppression resulting from chemotherapy and/or therapeutic radiation exposure. Chemotherapy refers to administration of a chemotherapy agent for the treatment of cancer. Many chemotherapeutic agents are known in the art to induce immune suppression due to their toxic effects on bone marrow cells. Chemotherapeutic agents include, without limitation, methotrexate, vincristine, adriamycin, cisplatin, non-sugar containing chloroethylnitrosoureas, 5-fluorouracil, mitomycin C, bleomycin, doxorubicin, dacarbazine, taxol, fragyline, Meglamine GLA, valrubicin, carmustaine and poliferposan, MMI270, BAY 12-9566, RAS farnesyl transferase inhibitor, farnesyl transferase inhibitor, MMP, MTA/LY231514, LY264618/Lometexol, Glamolec, CI-994, TNP-470, Hycamtin/Topotecan, PKC412, Valspodar/PSC833, Novantrone/Mitroxantrone, Metaret/Suramin, Batimastat, E7070, BCH-4556, CS-682, 9-AC, AG3340, AG3433, Incel/VX-710, VX-853, ZD0101, IS1641, ODN 698, TA 2516/Marmistat, BB2516/Marmistat, CDP 845, D2163, PD183805, DX8951f, Lemonal DP 2202, FK 317, Picibanil/OK-432, AD 32Nalrubicin, Metastron/strontium derivative, Temodal/Temozolomide, Evacet/liposomal doxorubicin, Yewtaxan/Paclitaxel, Taxol/Paclitaxel, Xeload/Capecitabine, Furtulon/Doxifluridine, Cyclopax/oral paclitaxel, Oral Taxoid, SPU-077/Cisplatin, HMR 1275/Flavopiridol, CP-358 (774)/EGFR, CP-609 (754)/RAS oncogene inhibitor, BMS-182751/oral platinum, UFT(Tegafur/Uracil), Ergamisol/Levamisole, Eniluracil/776C85/5FU enhancer, Campto/Levamisole, Camptosar/Irinotecan, Tumodex/Ralitrexed, Leustatin/Cladribine, Paxex/Paclitaxel, Doxil/liposomal doxorubicin, Caelyx/liposomal doxorubicin, Fludara/Fludarabine, Pharmarubicin/Epirubicin, DepoCyt, ZD1839, LU 79553/Bis-Naphtalimide, LU 103793/Dolastain, Caelyx/liposomal doxorubicin, Gemzar/Gemcitabine, ZD 0473/Anormed, YM 116, Iodine seeds, CDK4 and CDK2 inhibitors, PARP inhibitors, D4809/Dexifosamide, Ifes/Mesnex/Ifosamide, Vumon/Teniposide, Paraplatin/Carboplatin, Plantinol/cisplatin, Vepeside/Etoposide, ZD 9331, Taxotere/Docetaxel, prodrug of guanine arabinoside, Taxane Analog, nitrosoureas, alkylating agents such as melphalan and cyclophosphamide, Aminoglutethimide, Asparaginase, Busulfan, Carboplatin, Chlorombucil, Cytarabine HCl, Dactinomycin, Daunorubicin HCl, Estramustine phosphate sodium, Etoposide (VP16-213), Floxuridine, Fluorouracil (5-FU), Flutamide, Hydroxyurea (hydroxycarbamide), Ifosfamide, Interferon Alfa-2a, Alfa-2b, Leuprolide acetate (LHRH-releasing factor analogue), Lomustine (CCNU), Mechlorethamine HCl (nitrogen mustard), Mercaptopurine, Mesna, Mitotane (o.p'-DDD), Mitoxantrone HCl, Octreotide, Plicamycin, Procarbazine HCl, Streptozocin, Tamoxifen citrate, Thioguanine, Thiotepa, Vinblastine sulfate, Amsacrine (m-AMSA), Azacitidine, Hexamethylmelamine (HMM), Mitoguazone (methyl-GAG; methyl glyoxal bis-guanylhydrazone; MGBG), Pentostatin (2'deoxycoformycin), Semustine (methyl-CCNU), Teniposide (VM-26), and Vindesine sulfate.

Therapeutic radiation exposure refers to administration of prescribed amounts of ionizing irradiation directed or delivered systemically or to specified portions of the body to treat a condition such as a cancer. This type of radiation exposure can include, for example, X-rays, gamma rays (e.g., from cobalt 60), particle beams (e.g., electron beam radiation), or other external beam irradiation; internal radiation therapy (brachytherapy, e.g., iodine seeds); and systemic radiation therapy (e.g., iodine 131 and strontium 89).

In one embodiment the subject being treated has immune suppression resulting from accidental radiation exposure. As used herein, accidental radiation exposure is any radiation exposure other than therapeutic radiation exposure. In one embodiment accidental radiation exposure is the result of uncontrolled release of ionizing radiation, for example from detonation of a nuclear weapon.

ORN of the invention have adjuvant activity. Accordingly, the invention in certain aspects relates to methods of vaccinating a subject against an antigen. In one aspect the method of vaccinating a subject against an antigen includes the step of administering to the subject an effective amount of an ORN of the invention, and the antigen. In one aspect the method of vaccinating a subject against an antigen includes the step of administering to the subject an effective amount of a pharmaceutically acceptable salt of an ORN of the invention, and the antigen. Antigens are described above and can include, in certain embodiments, bacterial antigens, viral antigens, and cancer antigens. The administering can be accomplished by any suitable route or routes with respect to the compound and the antigen. In one embodiment the antigen and the compound of the invention are administered together, for example either as a single preparation or as separate preparations administered substantially simultaneously. When separate preparations are administered substantially simultaneously, the individual preparations can be administered to the same or different sites, by the same or different routes of administration. In one embodiment the antigen and the compound of the invention are not administered substantially simultaneously. For example, in one embodiment the administering the compound of the invention takes place before the administering the antigen. In one embodiment the administering the antigen takes place before the administering the compound of the invention. The period between the administering of the antigen and the administering the compound of the invention can be minutes, hours, or days, even up to a week. The individual components, i.e., antigen and compound of the invention, can be administered to the same or different sites, by the same or different routes of administration.

Routes of administration for vaccination include, without limitation, intramuscular, subcutaneous, and mucosal. In one embodiment the compound is administered intravenously.

In one embodiment the amount of antigen administered to the subject, according this aspect of the invention, is less than an effective amount of the antigen by itself to induce protective immunity. Combined with administering the compound of the invention, however, the administering the same amount of antigen is effective to induce protective immunity, i.e., to vaccinate the subject, against the antigen.

The invention in certain aspects relates to methods of treating a subject having cancer. In one aspect the method of treating a subject having cancer includes the step of administering to the subject an effective amount of an ORN of the invention. In one aspect the method of treating a subject having cancer includes the step of administering to the subject an effective amount of a pharmaceutically acceptable salt of an ORN of the invention.

As used herein, "treat" or "treating" refers to preventing, ameliorating, or eliminating a disease or condition in a subject having the disease or condition. In one embodiment "treat" or "treating" refers to ameliorating or eliminating a disease or condition in a subject having the disease or condition.

In the context of cancer, in certain non-limiting embodiments treating can refer to reducing the size of a tumor (including a metastasis), slowing the rate of growth or the rate or extent of spreading of a cancer, inducing a remission of a cancer, or curing a cancer.

A "subject having cancer" is a subject that has at least one objective manifestation of a cancer.

"Cancer" as used herein refers to an uncontrolled growth of cells which interferes with the normal functioning of the bodily organs and systems. Cancers which migrate from their original location and seed vital organs can eventually lead to the death of the subject through the functional deterioration of the affected organs. Hematopoietic cancers, such as leukemia, are able to outcompete the normal hematopoietic compartments in a subject, thereby leading to hematopoietic failure (in the form of anemia, thrombocytopenia and neutropenia) ultimately causing death.

Cancers include, but are not limited to, basal cell carcinoma, biliary tract cancer; bladder cancer; bone cancer; brain and other central nervous system (CNS) cancer; breast cancer; cervical cancer; choriocarcinoma; colon and rectum cancer; connective tissue cancer; cancer of the digestive system; endometrial cancer; esophageal cancer; eye cancer; cancer of the head and neck; gastric cancer; intra-epithelial neoplasm; kidney cancer; larynx cancer; leukemias, including hairy cell leukemia; liver cancer; lung cancer (e.g. small cell and non-small cell); lymphomas including Hodgkin's and non-Hodgkin's lymphomas; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; renal cancer; cancer of the respiratory system; sarcoma; skin cancer; stomach cancer; testicular cancer; thyroid cancer; uterine cancer; cancer of the urinary system, as well as other carcinomas and sarcomas.

A metastasis is a region of cancer cells, distinct from the primary tumor location resulting from the dissemination of cancer cells from the primary tumor to other parts of the body. At the time of diagnosis of the primary tumor mass, the subject may be monitored for the presence of metastases. Metastases are most often detected through the sole or combined use of magnetic resonance imaging (MRI) scans, computed tomography (CT) scans, blood and platelet counts, liver function studies, chest X-rays and bone scans in addition to the monitoring of specific symptoms.

In one embodiment the cancer is melanoma (primary or metastatic). In one embodiment the cancer is breast cancer. In one embodiment the cancer is lung cancer. In one embodiment the cancer is prostate cancer. In one embodiment the cancer is colon cancer. In one embodiment the cancer is hairy cell leukemia.

In one embodiment the method of treating a subject having cancer further includes administering to the subject a cancer antigen. In one embodiment the cancer antigen and the compound of the invention are administered together, for example either as a single preparation or as separate preparations administered substantially simultaneously. When separate preparations are administered substantially simultaneously, the individual preparations can be administered to the same or different sites, by the same or different routes of administration. In one embodiment the cancer antigen and the compound of the invention are not administered substantially simultaneously. For example, in one embodiment the administering the compound of the invention takes place before the administering the cancer antigen. In one embodiment the administering the cancer antigen takes place before the administering the compound of the invention. The period between the administering of the cancer antigen and the administering the compound of the invention can be minutes, hours, or days, even up to a week. The individual components, i.e., cancer antigen and compound of the invention, can be administered to the same or different sites, by the same or different routes of administration.

The invention in certain aspects relates to methods of treating a subject having an infection. In one aspect the method of treating a subject having an infection includes the step of administering to the subject an effective amount of an ORN of the invention. In one aspect the method of treating a subject having an infection includes the step of administering to the subject an effective amount of a pharmaceutically acceptable salt of an ORN of the invention.

In the context of infection, in certain non-limiting embodiments treating can refer to reducing at least one symptom of an infection, shortening the duration of an infection, slowing the rate or extent of spreading of an infection, or curing an infection.

As used herein, an "infection" refers to an infectious disease arising from the invasion of a host, superficially, locally, or systemically, by an infectious microorganism or infectious agent. A subject having an infection is a subject that has at least one objective manifestation of an infection. Infectious microorganisms and infectious agents include viruses, bacteria, parasites, and fungi. A viral infection refers to an infection by a virus. A bacterial infection refers to an infection by bacteria.

Examples of viruses that have been found in humans include but are not limited to: Retroviridae (e.g. human immunodeficiency viruses, such as HIV-1 (also referred to as HDTV-III, LAVE or HTLV-III/LAV, or HIV-III, and other isolates, such as HIV-LP)); Picornaviridae (e.g. polio viruses, hepatitis A virus; enteroviruses, human Coxsackie viruses, rhinoviruses, echoviruses); Calciviridae (e.g. strains that cause gastroenteritis); Togaviridae (e.g. equine encephalitis viruses, rubella viruses); Flaviviridae (e.g. dengue viruses, encephalitis viruses, yellow fever viruses); Coronoviridae (e.g. coronaviruses); Rhabdoviradae (e.g. vesicular stomatitis viruses, rabies viruses); Filoviridae (e.g. ebola viruses); Paramyxoviridae (e.g. parainfluenza viruses, mumps virus, measles virus, respiratory syncytial virus); Orthomyxoviridae (e.g. influenza viruses); Bunyaviridae (e.g. Hantaan viruses, bunya viruses, phleboviruses and Nairo viruses); Arenaviridae (hemorrhagic fever viruses); Reoviridae (e.g. reoviruses, orbiviruses and rotaviruses); Birnaviridae; Hepadnaviridae (Hepatitis B virus); Parvoviridae (parvoviruses); Papovaviridae (papillomaviruses, polyoma viruses); Adenoviridae (most adenoviruses); Herpesviridae (herpes simplex virus (HSV) 1 and 2, varicella zoster virus, cytomegalovirus (CMV), herpes virus); Poxyiridae (variola viruses, vaccinia viruses, pox viruses); and Iridoviridae (e.g. African swine fever virus); and unclassified viruses (e.g. the agent of delta hepatitis (thought to be a defective satellite of hepatitis B virus), the agents of non-A, non-B hepatitis (class 1=internally transmitted; class 2=parenterally transmitted (i.e. Hepatitis C); Norwalk and related viruses, and astroviruses).

Gram positive bacteria include, but are not limited to, *Pasteurella* species, Staphylococci species, and *Streptococcus* species. Gram negative bacteria include, but are not limited to, *Escherichia coli*, *Pseudomonas* species, and *Salmonella* species. Specific examples of infectious bacteria include but are not limited to, *Helicobacter pyloris, Borrelia burgdorferi, Legionella pneumophilia, Mycobacteria* sps (e.g. *M. tuberculosis, M. avium, M. intracellulare, M. kansasii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus anthracis, Corynebacterium diphtheriae, Corynebacterium* sp., *Erysipelothrix rhusiopathiae, Clostridium perfringens, Clostridium tetani, Enterobacter aerogenes, Klebsiella pneumoniae, Pasturella multocida, Bacteroides* sp., *Bacteroides fragilis, Fusobacterium nucleatum, Streptobacillus moniliformis, Treponema paffidium, Treponema pertenue, Leptospira, Rickettsia*, and *Actinomyces israelli*.

Examples of fungi include *Cryptococcus neoformans, Histoplasma capsulatum, Coccidioides immitis, Blastomyces dermatitidis, Chlamydia trachomatis, Candida albicans, Pneumocyctis carinii, Aspergillus*.

Other infectious'organisms (i.e., protists) include *Plasmodium* spp. such as *Plasmodium falciparum, Plasmodium malariae, Plasmodium ovale*, and *Plasmodium vivax* and *Toxoplasma gondii*. Blood-borne and/or tissues parasites include *Plasmodium* spp., *Babesia microti, Babesia divergens, Leishmania tropica, Leishmania* spp., *Leishmania braziliensis, Leishmania donovani, Trypanosoma gambiense* and *Trypanosoma rhodesiense* (African sleeping sickness), *Trypanosoma cruzi* (Chagas' disease), and *Toxoplasma gondii*.

Other medically relevant microorganisms and infectious agents have been described extensively in the literature, e.g., see C. G. A Thomas, Medical Microbiology, Bailliere Tindall, Great Britain 1983, the entire contents of which is hereby incorporated by reference.

The invention in certain aspects relates to methods of treating a subject having an allergic condition. In one aspect the method of treating a subject having an allergic condition includes the step of administering to the subject an effective amount of an ORN of the invention. In one aspect the method of treating a subject having an allergic condition includes the step of administering to the subject an effective amount of a pharmaceutically acceptable salt of an ORN of the invention.

In the context of an allergic condition, in certain non-limiting embodiments treating can refer to preventing at least one symptom of an allergic condition, reducing at least one symptom of an allergic condition, or shortening the duration of an allergic condition. Also in the context of allergic condition, in a non-limiting embodiment treating can refer to reducing the frequency of developing at least one symptom of an allergic condition.

As used herein, an "allergic condition" refers to an acquired hypersensitivity to a substance (allergen). A subject having an allergic condition is a subject that has at least one objective manifestation of an allergic reaction in response to exposure to or contact with an allergen. Allergic conditions are thus often situational, but the subject having the allergic condition is continuously primed to respond to the allergen. A subject having an allergic condition can but need not necessarily have the at least one objective manifestation of an allergic reaction at the time the subject is treated according to the method of the invention.

Allergic conditions include, without limitation, eczema, allergic rhinitis or coryza, hayfever, allergic asthma, urticaria (hives), food allergies, and other atopic conditions.

In one embodiment the allergic condition is allergic asthma. As used herein, "asthma" has its usual meaning and refers to a disorder of the respiratory system characterized by inflammation, narrowing of the airways, and increased reactivity of the airways to inhaled agents. As used herein, "allergic asthma" refers to asthma triggered by contact of a susceptible subject with an allergen. A diagnosis of allergic asthma can be made even without knowledge of the identity of a specific triggering allergen. Although allergic asthma is a very common form of asthma, the compounds and pharmaceutical compositions of the invention are also believed to be useful for the treatment of other forms of asthma in addition to allergic asthma, e.g., asthma associated with upper respiratory tract infection, exercise-induced asthma, and cold (temperature)-induced asthma.

In one embodiment the allergic condition excludes allergic asthma. This embodiment includes other allergic conditions including, without limitation, eczema, allergic rhinitis or coryza, hayfever, urticaria (hives), food allergies, and combinations thereof.

In one embodiment the method of treating a subject having an allergic condition further includes administering to the subject an allergen.

An "allergen" as used herein is a molecule capable of provoking an immune response characterized by production of IgE. An allergen is also a substance that can induce an allergic or asthmatic response in a susceptible subject. Thus, in the context of this invention, the term allergen means a specific type of antigen which can trigger an allergic response which is mediated by IgE antibody.

The list of allergens is enormous and can include pollens, insect venoms, animal dander dust, fungal spores and drugs (e.g., penicillin). Examples of natural animal and plant allergens include proteins specific to the following genuses: *Canis* (*Canis familiaris*); *Dermatophagoides* (e.g., *Dermatophagoides farinae*); *Felis* (*Felis domesticus*); *Ambrosia* (*Ambrosia artemisiifolia*); *Lolium* (e.g., *Lolium perenne* and *Lolium multiflorum*); *Cryptomeria* (*Cryptomeria japonica*); *Alternaria* (*Alternaria alternata*); *Alder; Alnus* (*Alnus gultinosa*); *Betula* (*Betula verrucosa*); *Quercus* (*Quercus alba*); *Olea* (*Olea europa*); *Artemisia* (*Artemisia vulgaris*); *Plantago* (e.g., *Plantago lanceolata*); *Parietaria* (e.g., *Parietaria officinalis* and *Parietaria judaica*); *Blattella* (e.g., *Blattella germanica*); *Apis* (e.g., *Apis multiflorum*); *Cupressus* (e.g., *Cupressus sempervirens, Cupressus arizonica* and *Cupressus macrocarpa*); *Juniperus* (e.g., *Juniperus sabinoides, Juniperus virginiana, Juniperus communis*, and *Juniperus* ashes); *Thuya* (e.g., *Thuya orientalis*); *Chamaecyparis* (e.g., *Chamaecyparis obtusa*); *Periplaneta* (e.g., *Periplaneta americana*); *Agropyron* (e.g., *Agropyron repens*); *Secale* (e.g., *Secale cereale*); *Triticum* (e.g., *Triticum aestivum*); *Dactylis* (e.g., *Dactylis glomerata*); *Festuca* (e.g., *Festuca elatior*); *Poa* (e.g., *Poa pratensis* and *Poa compressa*); *Avena* (e.g., *Avena sativa*); *Holcus* (e.g., *Holcus lanatus*); *Anthoxanthum* (e.g., *Anthoxanthum odoratum*); *Arrhenatherum* (e.g., *Arrhenatherum elatius*); *Agrostis* (e.g., *Agrostis alba*); *Phleum* (e.g., *Phleum pratense*); *Phalaris* (e.g., *Phalaris arundinacea*); *Paspalum* (e.g., *Paspalum notatum*); *Sorghum* (e.g., *Sorghum halepensis*); and *Bromus* (e.g., *Bromus inermis*). This list is not meant to be limiting.

In one embodiment the allergen and the compound of the invention are administered together, for example either as a single preparation or as separate preparations administered substantially simultaneously. When separate preparations are administered substantially simultaneously, the individual preparations can be administered to the same or different sites, by the same or different routes of administration. In one embodiment the allergen and the compound of the invention are not administered substantially simultaneously. For example, in one embodiment the administering the compound of the invention takes place before the administering the allergen. In one embodiment the administering the allergen takes place before the administering the compound of the invention. The period between the administering of the allergen and the administering the compound of the invention can be minutes, hours, or days, even up to a week. The individual components, i.e., allergen and compound of the invention, can be administered to the same or different sites, by the same or different routes of administration.

The invention in certain aspects relates to methods of treating a subject having asthma. In one aspect the method of treating a subject having asthma includes the step of administering to the subject an effective amount of an ORN of the invention. In one aspect the method of treating a subject having asthma includes the step of administering to the subject an effective amount of a pharmaceutically acceptable salt of an ORN of the invention.

In the context of asthma, in certain non-limiting embodiments treating can refer to preventing at least one symptom of asthma, reducing at least one symptom of asthma, or shortening the duration of an asthma attack. Also in the context of asthma, in a non-limiting embodiment treating can refer to reducing the frequency of developing at least one symptom of asthma.

In one embodiment asthma is allergic asthma.

The ORN of the invention can also be used for inhibiting gene expression of particular targets in addition to exerting their immune stimulatory effects. ORN sequences can be selected on the basis of corresponding target sequences. The target sequences can be obtained by sequencing or from gene or other nucleic acid sequence databases. Thus, ORN with a dual mode of action can be generated, such as antisense RNA inhibitors to suppress the expression of disease-causing genes and additional immune stimulation by activation of RIG-I or TLR7/8. An antisense sequence is a sequence that is complementary to a target sequence. Therefore, a ORN sequence can be selected which is directed, e.g., against a viral RNA. As an example, the antisense sequence can be complementary to hepatitis C virus (HCV) RNA, such as the HCV internal ribosome entry site (IRES):

```
Viral RNA
5' GAGCACGAAUCCUAAACCUCAAAGA 3'    (SEQ ID NO: 506)

Antisense
5' UCUUUGAGGUUUAGGAUUCGUGCUC 3'    (SEQ ID NO: 507)
```

The antisense strand with a 5'-triphosphate or 5'-triphosphate analog is then expected to inhibit HCV replication while the ORN at the same time induces potent immune stimulation through activation of RIG-I and/or TLR7/8.

Short interfering RNA (siRNA) is used for silencing gene expression. Dorsett Y et al. (2004) *Nat Rev Drug Discov* 3:318-29. ORN of the invention can also be used as double-stranded siRNA, in which at least one strand of the duplex comprises a 5'-triphosphate or 5'-triphosphate analog. The siRNA duplex can be blunt-ended or have overhanging ends. For example, a blunt-ended siRNA for hepatitis C can have a sense strand with the sequence identified above as Viral RNA and an antisense strand with the sequence identified above as Antisense.

The sense and antisense strands can also be linked by nucleotides as in short hairpin RNA (shRNA) or by non-nucleotidic linkers, such as abasic residues, $C_{18}$, or polyethylene glycol residues.

By selecting appropriate sequences against various viruses, ORN of the invention can be used in the context of antisense or RNAi, for the treatment of disorders caused by various viruses, including HCV, hepatitis B virus (HBV), cytomegalovirus (CMV), human immunodeficiency virus (HIV), herpes simplex virus 1 (HSV-1), herpes simplex virus 2 (HSV-2), human papillomavirus (HPV), vesicular stomatitis virus (VSV), polio viruses, influenza virus, and reoviruses. This list is not meant to be limiting.

By selecting appropriate sequences against various cancer- or tumor-related targets, ORN of the invention can also be used in the context of antisense or RNAi for the treatment of cancer. Thus, it is possible to use oligonucleotide sequences which are directed against targets responsible for the development or growth of cancers, such as oncoproteins, e.g., c-myc, N-myc, c-myb, c-fos, c-fos/jun, PCNA, p120, EJ-ras, c-Ha-ras, N-ras, rrg, bcl-2, bcl-x, bcl-w, cdc-2, c-raf-1, c-mos, c-src, c-abl, and c-ets; against cellular receptors, e.g., EGF receptor, Her-2, c-erbA, VEGF receptor (KDR-1), and retinoid receptors; against protein kinases, e.g., c-fms, Tie-2, c-raf-1 kinase, PKC-alpha, and protein kinase A (R1 alpha); against growth factors, e.g., bFGF, VEGF, EGF, HB-EGF, PDGF and TGF-β; against cytokines, e.g., IL-10; against cell cycle proteins, e.g., cyclin-E; against tumor proteins, e.g., MAT-8; and against inhibitors of tumor suppressor genes, e.g., MDM-2. Also of use are antisense or siRNA sequences directed against components of spindle formation, such as eg5 and PLK1, or against targets to suppress metastasis, such as CXCR4. Also of use are antisense or siRNA sequences directed against factors which suppress apoptosis, such as survivin, stat3, and hdm2, or which suppress the expression of multiple drug resistance genes, such as MDR1 (P-glycoprotein).

The ORN can also mimic micro RNA (miRNA) which are single-stranded RNA molecules of about 21-23 nucleotides in length regulating gene expression. miRNAs are encoded by genes that are transcribed from DNA but not translated into protein (non-coding RNA); instead they are processed from primary transcripts known as pri-miRNA to short stem-loop structures called pre-miRNA and finally to functional miRNA. Mature miRNA molecules are partially complementary to one or more messenger RNA (mRNA) molecules, and their main function is to down-regulate gene expression. It appears that many miRNA sequences discovered in the human genome contribute to the development of cancer. Some miRNAs are significantly deregulated in cancer, e.g., let-7 miRNA is a tumor suppressor which is under-expressed in certain tumors. Substitution of natural let-7 by ORN which mimic the let-7 sequence and also have a 5'-triphosphate or 5'-triphosphate analog can stimulate immune response in addition to suppress tumor growth. Further, miRNA which is over-expressed (e.g., TGF-β2 receptor, RB1, and PLAG1) leading to tumor growth can be down-regulated using antisense and siRNA approaches as described before. A miRNA expression signature of human solid tumors defining cancer gene targets has recently been reported. Volinia S et al. (2006) *Proc NAtl Acad Sci USA* 103:2257-61.

ORN of the invention can be combined with other therapeutic agents. The ORN of the invention and other therapeutic agent may be administered simultaneously or sequentially. When the other therapeutic agents are administered simultaneously, they can be administered in the same or separate formulations, but are administered at the same time. The other therapeutic agents are administered sequentially with one another and with the ORN of the invention, when the administration of the other therapeutic agents and the ORN of the invention is temporally separated. The separation in time between the administration of these compounds may be a matter of minutes or it may be longer. Other therapeutic agents include but are not limited to anti-microbial agents, anti-cancer agents, anti-allergy agents, and anti-asthma agents.

The ORN of the invention may be administered to a subject with an anti-microbial agent. An anti-microbial agent, as used herein, refers to a naturally-occurring or synthetic compound which is capable of killing or inhibiting infectious microorganisms or infectious agents. The type of anti-microbial agent useful according to the invention will depend upon the type of microorganism or infectious agent with which the subject is infected or at risk of becoming infected. Anti-microbial agents include but are not limited to anti-bacterial agents, anti-viral agents, anti-fungal agents and anti-parasitic agents. Phrases such as "anti-infective agent", "anti-bacterial agent", "anti-viral agent", "anti-fungal agent", "anti-parasitic agent" and "parasiticide" have well-established meanings to those of ordinary skill in the art and are defined in standard medical texts.

Anti-bacterial agents kill or inhibit bacteria and include antibiotics as well as other synthetic or natural compounds having similar functions. Antibiotics are low molecular weight molecules which are produced as secondary metabolites by cells, such as microorganisms. In general, antibiotics interfere with one or more bacterial functions or structures which are specific for the microorganism and which are not present in host cells. Anti-viral agents can be isolated from natural sources or synthesized and are useful for killing or inhibiting viruses. Anti-fungal agents are used to treat superficial fungal infections as well as opportunistic and primary systemic fungal infections. Anti-parasitic agents kill or inhibit parasites.

Anti-bacterial agents kill or inhibit the growth or function of bacteria. A large class of anti-bacterial agents is antibiotics. Antibiotics which are effective for killing or inhibiting a wide range of bacteria are referred to as broad spectrum antibiotics. Other types of antibiotics are predominantly effective against the bacteria of the class gram-positive or gram-negative. These types of antibiotics are referred to as narrow spectrum antibiotics. Other antibiotics which are effective against a single organism or disease and not against other types of bacteria are referred to as limited spectrum antibiotics. Antibacterial agents are sometimes classified based on their primary mode of action. In general, antibacterial agents are cell wall synthesis inhibitors, cell membrane inhibitors, protein synthesis inhibitors, nucleic acid synthesis or functional inhibitors, and competitive inhibitors.

Antibiotics include, without limitation, natural penicillins, semi-synthetic penicillins, clavulanic acid, cephalosporins, bacitracin, ampicillin, carbenicillin, oxacillin, azlocillin, mezlocillin, piperacillin, methicillin, dicloxacillin, nafcillin, cephalothin, cephapirin, cephalexin, cefamandole, cefaclor, cefazolin, cefuroxine, cefoxitin, cefotaxime, cefsulodin, cefetamet, cefixime, ceftriaxone, cefoperazone, ceftazidine, moxalactam, carbapenems, imipenems, monobactems, eurtreonam, vancomycin, polymyxin, amphotericin B, nystatin, imidazoles, clotrimazole, miconazole, ketoconazole, itraconazole, fluconazole, rifampins, ethambutol, tetracyclines, chloramphenicol, macrolides, aminoglycosides, streptomycin, kanamycin, tobramycin, amikacin, gentamicin, tetracycline, minocycline, doxycycline, chlortetracycline, erythromycin, roxithromycin, clarithromycin, oleandomycin, azithromycin, chloramphenicol, quinolones, co-trimoxazole, norfloxacin, ciprofloxacin, enoxacin, nalidixic acid, temafloxacin, sulfonamides, gantrisin, and trimethoprim; Acedapsone; Acetosulfone Sodium; Alamecin; Alexidine; Amdinocillin; Amdinocillin Pivoxil; Amicycline; Amifloxacin; Amifloxacin Mesylate; Amikacin; Amikacin Sulfate; Aminosalicylic acid; Aminosalicylate sodium; Amoxicillin; Amphomycin; Ampicillin; Ampicillin Sodium; Apalcillin Sodium; Apramycin; Aspartocin; Astromicin Sulfate; Avilamycin; Avoparcin; Azithromycin; Azlocillin; Azlocillin Sodium; Bacampicillin Hydrochloride; Bacitracin; Bacitracin Methylene Disalicylate; Bacitracin Zinc; Bambermycins; Benzoylpas Calcium; Berythromycin; Betamicin Sulfate; Biapenem; Biniramycin; Biphenamine Hydrochloride; Bispyrithione Magsulfex; Butikacin; Butirosin Sulfate; Capreomycin Sulfate; Carbadox; Carbenicillin Disodium; Carbenicillin Indanyl Sodium; Carbenicillin Phenyl Sodium; Carbenicillin Potassium; Carumonam Sodium; Cefaclor; Cefadroxil; Cefamandole; Cefamandole Nafate; Cefamandole Sodium; Cefaparole; Cefatrizine; Cefazaflur Sodium; Cefazolin; Cefazolin Sodium; Cefbuperazone; Cefdinir; Cefepime; Cefepime Hydrochloride; Cefetecol; Cefixime; Cefmenoxime Hydrochloride; Cefmetazole; Cefmetazole Sodium; Cefonicid Monosodium; Cefonicid Sodium; Cefoperazone Sodium; Ceforanide; Cefotaxime Sodium; Cefotetan; Cefotetan Disodium; Cefotiam Hydrochloride; Cefoxitin; Cefoxitin Sodium; Cefpimizole; Cefpimizole Sodium; Cefpiramide; Cefpiramide Sodium; Cefpirome Sulfate; Cefpodoxime Proxetil; Cefprozil; Cefroxadine; Cefsulodin Sodium; Ceftazidime; Ceftibuten; Ceftizoxime Sodium; Ceftriaxone Sodium; Cefuroxime; Cefuroxime Axetil; Cefuroxime Pivoxetil; Cefuroxime Sodium; Cephacetrile Sodium; Cephalexin; Cephalexin Hydrochloride; Cephaloglycin; Cephaloridine; Cephalothin Sodium; Cephapirin Sodium; Cephradine; Cetocycline Hydrochloride; Cetophenicol; Chloramphenicol; Chloramphenicol Palmitate; Chloramphenicol Pantothenate Complex; Chloramphenicol Sodium Succinate; Chlorhexidine Phosphanilate; Chloroxylenol; Chlortetracycline Bisulfate; Chlortetracycline Hydrochloride; Cinoxacin; Ciprofloxacin; Ciprofloxacin Hydrochloride; Cirolemycin; Clarithromycin; Clinafloxacin Hydrochloride; Clindamycin; Clindamycin Hydrochloride; Clindamycin Palmitate Hydrochloride; Clindamycin Phosphate; Clofazimine; Cloxacillin Benzathine; Cloxacillin Sodium; Cloxyquin; Colistimethate Sodium; Colistin Sulfate; Coumermycin; Coumermycin Sodium; Cyclacillin; Cycloserine; Dalfopristin; Dapsone; Daptomycin; Demeclocycline; Demeclocycline Hydrochloride; Demecycline; Denofungin; Diaveridine; Dicloxacillin; Dicloxacillin Sodium; Dihydrostreptomycin Sulfate; Dipyrithione; Dirithromycin; Doxycycline; Doxycycline Calcium; Doxycycline Fosfatex; Doxycycline Hyclate; Droxacin Sodium; Enoxacin; Epicillin; Epitetracycline Hydrochloride; Erythromycin; Erythromycin Acistrate; Erythromycin Estolate; Erythromycin Ethylsuccinate; Erythromycin Gluceptate; Erythromycin Lactobionate; Erythromycin Propionate; Erythromycin Stearate; Ethambutol Hydrochloride; Ethionamide; Fleroxacin; Floxacillin; Fludalanine; Flumequine; Fosfomycin; Fosfomycin Tromethamine; Fumoxicillin; Furazolium Chloride; Furazolium Tartrate; Fusidate Sodium; Fusidic Acid; Gentamicin Sulfate; Gloximonam; Gramicidin; Haloprogin; Hetacillin; Hetacillin Potassium; Hexedine; Ibafloxacin; Imipenem; Isoconazole; Isepamicin; Isoniazid; Josamycin; Kanamycin Sulfate; Kitasamycin; Levofuraltadone; Levopropylcillin Potassium; Lexithromycin; Lincomycin; Lincomycin Hydrochloride; Lomefloxacin; Lomefloxacin Hydrochloride; Lomefloxacin Mesylate; Loracarbef; Mafenide; Meclocycline; Meclocycline Sulfosalicylate; Megalomicin Potassium Phosphate; Mequidox; Meropenem; Methacycline; Methacycline Hydrochloride; Methenamine; Methenamine Hippurate; Methenamine Mandelate; Methicillin Sodium; Metioprim; Metronidazole Hydrochloride; Metronidazole Phosphate; Mezlocillin; Mezlocillin Sodium; Minocycline; Minocycline Hydrochloride; Mirincamycin Hydrochloride; Monensin; Monensin Sodium; Nafcillin Sodium; Nalidixate Sodium; Nalidixic Acid; Natamycin; Nebramycin; Neomycin Palmitate; Neomycin Sulfate; Neomycin Undecylenate; Netilmicin Sulfate; Neutramycin; Nifuradene; Nifuraldezone; Nifuratel; Nifuratrone; Nifurdazil; Nifurimide; Nifurpirinol; Nifurquinazol; Nifurthiazole; Nitrocycline; Nitrofurantoin; Nitromide; Norfloxacin; Novobiocin Sodium; Ofloxacin; Ormetoprim; Oxacillin Sodium; Oximonam; Oximonam Sodium; Oxolinic Acid; Oxytetracycline; Oxytetracycline Calcium; Oxytetracycline Hydrochloride; Paldimycin; Parachlorophenol; Paulomycin; Pefloxacin; Pefloxacin Mesylate; Penamecillin; Penicillin G Benzathine; Penicillin G Potassium; Penicillin G Procaine; Penicillin G Sodium; Penicillin V; Penicillin V Benzathine; Penicillin V Hydrabamine; Penicillin V Potassium; Pentizidone Sodium; Phenyl Aminosalicylate; Piperacillin Sodium; Pirbenicillin Sodium; Piridicillin Sodium; Pirlimycin Hydrochloride; Pivampicillin Hydrochloride; Pivampicillin Pamoate; Pivampicillin Probenate; Polymyxin B Sulfate; Porfiromycin; Propikacin; Pyrazinamide; Pyrithione Zinc; Quindecamine Acetate; Quinupristin; Racephenicol; Ramoplanin; Ranimycin; Relomycin; Repromicin; Rifabutin; Rifametane; Rifamexil; Rifamide; Rifampin; Rifapentine; Rifaximin; Rolitetracycline; Rolitetracycline Nitrate; Rosaramicin; Rosaramicin Butyrate; Rosaramicin Propionate; Rosaramicin Sodium Phosphate; Rosaramicin Stearate; Rosoxacin; Roxarsone; Roxithromycin; Sancycline; Sanfetrinem Sodium; Sarmoxicillin; Sarpicillin; Scopafungin; Sisomicin; Sisomicin Sulfate; Sparfloxacin; Spectinomycin Hydrochloride; Spiramycin; Stallimycin Hydrochloride; Steffimycin; Streptomycin Sulfate; Streptonicozid; Sulfabenz; Sulfabenzamide; Sulfacetamide; Sulfacetamide Sodium; Sulfacytine; Sulfadiazine; Sulfadiazine Sodium; Sulfadoxine; Sulfalene; Sulfamerazine; Sulfameter; Sulfamethazine; Sulfamethizole; Sulfamethoxazole; Sulfamonomethoxine; Sulfamoxole; Sulfanilate Zinc; Sulfanitran; Sulfasalazine; Sulfasomizole; Sulfathiazole; Sulfazamet; Sulfisoxazole; Sulfisoxazole Acetyl; Sulfisoxazole Diolamine; Sulfomyxin; Sulopenem; Sultamicillin; Suncillin Sodium; Talampicillin Hydrochloride; Teicoplanin; Temafloxacin Hydrochloride; Temocillin; Tetracycline; Tetracycline Hydrochloride; Tetracycline Phosphate Complex; Tetroxoprim; Thiamphenicol; Thiphencillin Potassium; Ticarcillin Cresyl Sodium; Ticarcillin Disodium; Ticarcillin Monosodium; Ticlatone; Tiodonium Chloride; Tobramycin; Tobramycin Sulfate; Tosufloxacin; Trimethoprim; Trimethoprim Sulfate; Trisulfapyrimidines; Troleandomycin; Trospectomycin Sulfate; Tyrothricin; Vancomycin; Vancomycin Hydrochloride; Virginiamycin; and Zorbamycin.

Anti-viral agents are compounds which prevent infection of cells by viruses or replication of the virus within the cell. There are many fewer antiviral drugs than antibacterial drugs because the process of viral replication is so closely related to DNA replication within the host cell that non-specific antiviral agents would often be toxic to the host. There are several stages within the process of viral infection which can be blocked or inhibited by antiviral agents. These stages include, attachment of the virus to the host cell (immunoglobulin or binding peptides), uncoating of the virus (e.g. amantadine), synthesis or translation of viral mRNA (e.g. interferon), replication of viral RNA or DNA (e.g. nucleotide analogues), maturation of new virus proteins (e.g. protease inhibitors), and budding and release of the virus.

Nucleotide analogues are synthetic compounds which are similar to nucleotides, but which have an incomplete or abnormal deoxyribose or ribose group. Once the nucleotide analogues are in the cell, they are phosphorylated, producing the triphosphate formed which competes with normal nucleotides for incorporation into the viral DNA or RNA. Once the triphosphate form of the nucleotide analogue is incorporated into the growing nucleic acid chain, it causes irreversible association with the viral polymerase and thus chain termination. Nucleotide analogues include, but are not limited to, acyclovir (used for the treatment of herpes simplex virus and varicella-zoster virus), gancyclovir (useful for the treatment of cytomegalovirus), idoxuridine, ribavirin (useful for the treatment of respiratory syncitial virus), dideoxyinosine, dideoxycytidine, zidovudine (azidothymidine), imiquimod, and resimiquimod.

Anti-viral agents useful in the invention include but are not limited to immunoglobulins, amantadine, interferons, nucleotide analogues, and protease inhibitors. Specific examples of anti-virals include but are not limited to Acemannan; Acyclovir; Acyclovir Sodium; Adefovir; Alovudine; Alvircept Sudotox; Amantadine Hydrochloride; Aranotin; Arildone; Atevirdine Mesylate; Avridine; Cidofovir; Cipamfylline; Cytarabine Hydrochloride; Delavirdine Mesylate; Desciclovir; Didanosine; Disoxaril; Edoxudine; Enviradene; Enviroxime; Famciclovir; Famotine Hydrochloride; Fiacitabine; Fialuridine; Fosarilate; Foscarnet Sodium; Fosfonet Sodium; Ganciclovir; Ganciclovir Sodium; Idoxuridine; Kethoxal; Lamivudine; Lobucavir; Memotine Hydrochloride; Methisazone; Nevirapine; Penciclovir; Pirodavir; Ribavirin; Rimantadine Hydrochloride; Saquinavir Mesylate; Somantadine Hydrochloride; Sorivudine; Statolon; Stavudine; Tilorone Hydrochloride; Trifluridine; Valacyclovir Hydrochloride; Vidarabine; Vidarabine Phosphate; Vidarabine Sodium Phosphate; Viroxime; Zalcitabine; Zidovudine; and Zinviroxime.

Anti-fungal agents are useful for the treatment and prevention of infective fungi. Anti-fungal agents are sometimes classified by their mechanism of action. Some anti-fungal agents function as cell wall inhibitors by inhibiting glucose synthase. These include, but are not limited to, basiungin/ECB. Other anti-fungal agents function by destabilizing membrane integrity. These include, but are not limited to, imidazoles, such as clotrimazole, sertaconzole, fluconazole, itraconazole, ketoconazole, miconazole, and voriconacole, as well as FK 463, amphotericin B, BAY 38-9502, MK 991, pradimicin, UK 292, butenafine, and terbinafine. Other antifungal agents function by breaking down chitin (e.g. chitinase) or immunosuppression (501 cream).

Examples of anti-parasitic agents, also referred to as parasiticides useful for human administration include but are not limited to albendazole, amphotericin B, benznidazole, bithionol, chloroquine HCl, chloroquine phosphate, clindamycin, dehydroemetine, diethylcarbamazine, diloxanide furoate, eflornithine, furazolidaone, glucocorticoids, halofantrine, iodoquinol, ivermectin, mebendazole, mefloquine, meglumine antimoniate, melarsoprol, metrifonate, metronidazole, niclosamide, nifurtimox, oxamniquine, paromomycin, pentamidine isethionate, piperazine, praziquantel, primaquine phosphate, proguanil, pyrantel pamoate, pyrimethanmine-sulfonamides, pyrimethanmine-sulfadoxine, quinacrine HCl, quinine sulfate, quinidine gluconate, spiramycin, stibogluconate sodium (sodium antimony gluconate), suramin, tetracycline, doxycycline, thiabendazole, tinidazole, trimethroprim-sulfamethoxazole, and tryparsamide some of which are used alone or in combination with others.

The compounds of the invention may also be administered in conjunction with an anti-cancer agent or other anti-cancer therapy. Anti-cancer therapies include anti-cancer agents or, equivalently, cancer medicaments, as well as radiation and surgical procedures. As used herein, an "anti-cancer agent" or "cancer medicament" refers to an agent which is administered to a subject for the purpose of treating a cancer. In other aspects, a cancer medicament is administered to a subject at risk of developing a cancer for the purpose of reducing the risk of developing the cancer. Various types of medicaments for the treatment of cancer are described herein. For the purpose of this specification, anti-cancer agents or, equivalently, cancer medicaments are classified as chemotherapeutic agents, immunotherapeutic agents, cancer vaccines, hormone therapy, and biological response modifiers.

The chemotherapeutic agent may be selected from the group consisting of methotrexate, vincristine, adriamycin, cisplatin, non-sugar containing chloroethylnitrosoureas, 5-fluorouracil, mitomycin C, bleomycin, doxorubicin, dacarbazine, taxol, fragyline, Meglamine GLA, valrubicin, carmustaine and poliferposan, MMI270, BAY 12-9566, RAS farnesyl transferase inhibitor, farnesyl transferase inhibitor, MMP, MTA/LY231514, LY264618/Lometexol, Glamolec, CI-994, TNP-470, Hycamtin/Topotecan, PKC412, Valspodar/PSC833, Novantrone/Mitroxantrone, Metaret/Suramin, Batimastat, E7070, BCH-4556, CS-682, 9-AC, AG3340, AG3433, Incel/VX-710, VX-853, ZD0101, IS1641, ODN 698, TA 2516/Marmistat, BB2516/Marmistat, CDP 845, D2163, PD183805, DX8951f, Lemonal DP 2202, FK 317, Picibanil/OK-432, AD 32/Valrubicin, Metastron/strontium derivative, Temodal/Temozolomide, Evacet/liposomal doxorubicin, Yewtaxan/Paclitaxel, Taxol/Paclitaxel, Xeload/Capecitabine, Furtulon/Doxifluridine, Cyclopax/oral paclitaxel, Oral Taxoid, SPU-077/Cisplatin, HMR 1275/Flavopiridol, CP-358 (774)/EGFR, CP-609 (754)/RAS oncogene inhibitor, BMS-182751/oral platinum, UFT (Tegafur/Uracil), Ergamisol/Levamisole, Eniluracil/776C85/5FU enhancer, Campto/Levamisole, Camptosar/Irinotecan, Tumodex/Ralitrexed, Leustatin/Cladribine, Paxex/Paclitaxel, Doxil/liposomal doxorubicin, Caelyx/liposomal doxorubicin, Fludara/Fludarabine, Pharmarubicin/Epirubicin, DepoCyt, ZD1839, LU 79553/Bis-Naphtalimide, LU 103793/Dolastain, Caetyx/liposomal doxorubicin, Gemzar/Gemcitabine, ZD 0473/Anormed, YM 116, Iodine seeds, CDK4 and CDK2 inhibitors, PARP inhibitors, D4809/Dexifosamide, Ifes/Mesnex/Ifosamide, Vumon/Teniposide, Paraplatin/Carboplatin, Plantinol/cisplatin, Vepeside/Etoposide, ZD 9331, Taxotere/Docetaxel, prodrug of guanine arabinoside, Taxane Analog, nitrosoureas, alkylating agents such as melphelan and cyclophosphamide, Aminoglutethimide, Asparaginase, Busulfan, Carboplatin, Chlorombucil, Cytarabine HCl, Dactinomycin, Daunorubicin HCl, Estramustine phosphate sodium, Etoposide (VP16-213), Floxuridine, Fluorouracil (5-FU), Flutamide, Hydroxyurea (hydroxycarbamide), Ifosfamide, Interferon Alfa-2a, Alfa-2b, Leuprolide acetate (LHRH-releasing factor analogue), Lomustine (CCNU), Mechlorethamine HCl (nitrogen mustard), Mercaptopurine, Mesna, Mitotane (o.p'-DDD), Mitoxantrone HCl, Octreotide, Plicamycin, Procarbazine HCl, Streptozocin, Tamoxifen citrate, Thioguanine, Thiotepa, Vinblastine sulfate, Amsacrine (m-AMSA), Azacitidine, Erthropoietin, Hexamethylmelamine (HMM), Interleukin 2, Mitoguazone (methyl-GAG; methyl glyoxal bis-guanylhydrazone; MGBG), Pentostatin (2'deoxycoformycin), Semustine (methyl-CCNU), Teniposide (VM-26) and Vindesine sulfate, but it is not so limited.

The immunotherapeutic agent may be selected from the group consisting of The immunotherapeutic agent may be selected from the group consisting of Ributaxin, Rituxan, Herceptin, Quadramet, Panorex, IDEC-Y2B8, BEC2, C225, Oncolym, SMART M195, ATRAGEN, Ovarex, Bexxar, LDP-03, ior t6, MDX-210, MDX-11, MDX-22, OV103, 3622W94, anti-VEGF, Zenapax, MDX-220, MDX-447, MELIMMUNE-2, MELIMMUNE-1, CEACIDE, Pretarget, NovoMAb-G2, TNT, Gliomab-H, GNI-250, EMD-72000, LymphoCide, CMA 676, Monopharm-C, 4B5, ior egf.r3, ior c5, BABS, anti-FLK-2, MDX-260, ANA Ab, SMART 1D10 Ab, SMART ABL 364 Ab and ImmuRAIT-CEA, but it is not so limited.

The cancer vaccine may be selected from the group consisting of EGF, Anti-idiotypic cancer vaccines, Gp75 antigen, GMK melanoma vaccine, MGV ganglioside conjugate vaccine, Her2/neu, Ovarex, M-Vax, O-Vax, L-Vax, STn-KHL theratope, BLP25 (MUC-1), liposomal idiotypic vaccine, Melacine, peptide antigen vaccines, toxin/antigen vaccines, MVA-based vaccine, PACIS, BCG vaccine, TA-HPV, TA-CIN, DISC-virus and ImmuCyst/TheraCys, but it is not so limited.

Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is effective to treat the particular subject. The effective amount for any particular application can vary depending on such factors as the disease or condition being treated, the particular ORN being administered, the size of the subject, or the severity of the disease or condition. One of ordinary skill in the art can empirically determine the effective amount of a particular ORN and/or other therapeutic agent without necessitating undue experimentation. It is preferred generally that a maximum dose be used, that is, the highest safe dose according to some medical judgment. Multiple doses per day may be contemplated to achieve appropriate systemic levels of compounds. Appropriate system levels can be determined by, for example, measurement of the patient's peak or sustained plasma level of the drug. "Dose" and "dosage" are used interchangeably herein.

Generally, daily oral doses of active compounds will be from about 0.01 milligrams/kg per day to 1000 milligrams/kg per day. It is expected that oral doses in the range of 0.5 to 50 milligrams/kg, in one or several administrations per day, will yield the desired results. Dosage may be adjusted appropriately to achieve desired drug levels, local or systemic, depending upon the mode of administration. For example, it is expected that intravenous administration would be from an order to several orders of magnitude lower dose per day. In the event that the response in a subject is insufficient at such doses, even higher doses (or effective higher doses by a different, more localized delivery route) may be employed to the extent that patient tolerance permits. Multiple doses per day are contemplated to achieve appropriate systemic levels of compounds.

For any compound described herein the therapeutically effective amount can be initially determined from animal models. A therapeutically effective dose can also be determined from human data for ORN which have been tested in humans and for compounds which are known to exhibit similar pharmacological activities, such as other related active agents. Higher doses may be required for parenteral administration. The applied dose can be adjusted based on the relative bioavailability and potency of the administered compound. Adjusting the dose to achieve maximal efficacy based on the methods described above and other methods as are well-known in the art is well within the capabilities of the ordinarily skilled artisan.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

For use in therapy, an effective amount of the ORN can be administered to a subject by any mode that delivers the ORN to the desired surface. Administering the pharmaceutical composition of the present invention may be accomplished by any means known to the skilled artisan. Routes of administration include but are not limited to oral, parenteral, intravenous, intraperitoneal, intramuscular, subcutaneous, intranasal, sublingual, intratracheal, inhalation, ocular, vaginal, and rectal.

For oral administration, the compounds (i.e., ORN of the invention, and other therapeutic agents) can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, e.g., EDTA for neutralizing internal acid conditions or may be administered without any carriers.

Also specifically contemplated are oral dosage forms of the above component or components. The component or components may be chemically modified so that oral delivery of the derivative is efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis, 1981, "Soluble Polymer-Enzyme Adducts" In: *Enzymes as Drugs*, Hocenberg and Roberts, eds., Wiley-Interscience, New York, N.Y., pp. 367-383; Newmark, et al., 1982, J. Appl. Biochem. 4:185-189. Other polymers that could be used are poly-1,3-dioxolane and poly-1,3,6-tioxocane. Preferred for pharmaceutical usage, as indicated above, are polyethylene glycol moieties.

For the component (or derivative) the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the ORN (or derivative) or by release of the biologically active material beyond the stomach environment, such as in the intestine.

To ensure full gastric resistance a coating impermeable to at least pH 5.0 is essential. Examples of more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic i.e. powder; for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the ORN (or derivative) may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, a-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential non-ionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the ORN or derivative either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

Also contemplated herein is pulmonary delivery of the ORN (or derivatives thereof). The ORN (or derivative) is delivered to the lungs of a mammal while inhaling and traverses across the lung epithelial lining to the blood stream. Other reports of inhaled molecules include Adjei et al., 1990, Pharmaceutical Research, 7:565-569; Adjei et al., 1990, International Journal of Pharmaceutics, 63:135-144 (leuprolide acetate); Braquet et al., 1989, Journal of Cardiovascular Pharmacology, 13 (suppl. 5):143-146 (endothelin-1); Hubbard et al., 1989, Annals of Internal Medicine 3:206-212 (α1-antitrypsin); Smith et al., 1989, J. Clin. Invest. 84:1145-1146 (a-1-proteinase); Oswein et al., 1990, "Aerosolization of Proteins", Proceedings of Symposium on Respiratory Drug Delivery II, Keystone, Colo., March, (recombinant human growth hormone); Debs et al., 1988, J. Immunol. 140:3482-3488 (interferon-g and tumor necrosis factor alpha) and Platz et al., U.S. Pat. No. 5,284,656 (granulocyte colony stimulating factor). A method and composition for pulmonary delivery of drugs for systemic effect is described in U.S. Pat. No. 5,451,569, issued Sep. 19, 1995 to Wong et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

All such devices require the use of formulations suitable for the dispensing of ORN (or derivative). Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified ORN may also be prepared in different formulations depending on the type of chemical modification or the type of device employed.

Formulations suitable for use with a nebulizer, either jet or ultrasonic, will typically comprise ORN (or derivative) dissolved in water at a concentration of about 0.1 to 25 mg of biologically active ORN per mL of solution. The formulation may also include a buffer and a simple sugar (e.g., for ORN stabilization and regulation of osmotic pressure). The nebulizer formulation may also contain a surfactant, to reduce or prevent surface induced aggregation of the ORN caused by atomization of the solution in forming the aerosol.

Formulations for use with a metered-dose inhaler device will generally comprise a finely divided powder containing the ORN (or derivative) suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing ORN (or derivative) and may also include a bulking agent, such as lactose, sorbitol, sucrose, or mannitol in amounts which facilitate dispersal of the powder from the device, e.g., 50 to 90% by weight of the formulation. The ORN (or derivative) should most advantageously be prepared in particulate form with an average particle size of less than 10 μm (or microns), most preferably 0.5 to 5 μm, for most effective delivery to the distal lung.

Nasal delivery of a pharmaceutical composition of the present invention is also contemplated. Nasal delivery allows the passage of a pharmaceutical composition of the present invention to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer, *Science* 249:1527-1533, 1990, which is incorporated herein by reference.

The ORN and optionally other therapeutics may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Pharmaceutically acceptable salts include, without limitation, those salts prepared from alkaline metal or alkaline earth salts, such as sodium, potassium, or calcium salts, and, of particular interest in connection with ORN of the invention, those salts prepared from the following bases: ammonia, pyridine, piperidine, trimethylamine, triethylamine, tributylamine, picoline, dicyclohexylamine, diethanolamine, tris(hydroxymethylamino)-methane, phenylethylbenzylamine, spermine, spermidine, lysine, and arginine.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

The pharmaceutical compositions of the invention contain an effective amount of a ORN and optionally therapeutic agents included in a pharmaceutically-acceptable carrier. The term pharmaceutically-acceptable carrier means one or more compatible solid or liquid filler, diluents or encapsulating substances which are suitable for administration to a human or other vertebrate animal. The term carrier denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficiency.

The therapeutic agent(s), including specifically but not limited to the ORN, may be provided in particles. Particles as used herein means nano or microparticles (or in some instances larger) which can consist in whole or in part of the ORN or the other therapeutic agent(s) as described herein. The particles may contain the therapeutic agent(s) in a core surrounded by a coating, including, but not limited to, an enteric coating. The therapeutic agent(s) also may be dispersed throughout the particles. The therapeutic agent(s) also may be adsorbed into the particles. The particles may be of any order release kinetics, including zero order release, first order release, second order release, delayed release, sustained release, immediate release, and any combination thereof, etc. The particle may include, in addition to the therapeutic agent(s), any of those materials routinely used in the art of pharmacy and medicine, including, but not limited to, erodible, nonerodible, biodegradable, or nonbiodegradable material or combinations thereof. The particles may be microcapsules which contain the ORN in a solution or in a semi-solid state. The particles may be of virtually any shape.

Both non-biodegradable and biodegradable polymeric materials can be used in the manufacture of particles for delivering the therapeutic agent(s). Such polymers may be natural or synthetic polymers. The polymer is selected based on the period of time over which release is desired. Bioadhesive polymers of particular interest include bioerodible hydrogels described by H. S. Sawhney, C. P. Pathak and J. A. Hubell in *Macromolecules*, (1993) 26:581-587, the teachings of which are incorporated herein. These include polyhyaluronic acids, casein, gelatin, glutin, polyanhydrides, polyacrylic acid, alginate, chitosan, poly(methyl methacrylates), poly(ethyl methacrylates), poly(butylmethacrylate), poly (isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

The therapeutic agent(s) may be contained in controlled release systems. The term "controlled release" is intended to refer to any drug-containing formulation in which the manner and profile of drug release from the formulation are controlled. This refers to immediate as well as non-immediate release formulations, with non-immediate release formulations including but not limited to sustained release and delayed release formulations. The term "sustained release" (also referred to as "extended release") is used in its conventional sense to refer to a drug formulation that provides for gradual release of a drug over an extended period of time, and that preferably, although not necessarily, results in substantially constant blood levels of a drug over an extended time period. The term "delayed release" is used in its conventional sense to refer to a drug formulation in which there is a time delay between administration of the formulation and the release of the drug there from. "Delayed release" may or may not involve gradual release of drug over an extended period of time, and thus may or may not be "sustained release."

Use of a long-term sustained release implant may be particularly suitable for treatment of chronic conditions. "Long-term" release, as used herein, means that the implant is constructed and arranged to deliver therapeutic levels of the active ingredient for at least 7 days, and preferably 30-60 days. Long-term sustained release implants are well-known to those of ordinary skill in the art and include some of the release systems described above.

The present invention is further illustrated by the following Examples, which in no way should be construed as further limiting. The entire contents of all of the references (including literature references, issued patents, published patent applications, and co-pending patent applications) cited throughout this application are expressly incorporated herein by reference.

EXAMPLES

Example 1

Solid-Phase Synthesis

Oligonucleotides were synthesized on an ÄKTA Oligopilot 10 DNA/RNA synthesizer (GE-Healthcare) on a 10 μmole scale using standard β-cyanoethyl phosphoramidite chemistry. Primer supports PS200 were purchased from GE-Healthcare (loading: 40 μmol/g). 5'-DMT-protected β-cyanoethyl phosphoramidites (Sigma-Aldrich) were used for the synthesis of oligo-2'-deoxynucleotides and 5'-DMT-2'-TBDMS building-blocks (Sigma-Aldrich) were used for synthesis of oligoribonucleotides. After elongation of the of the oligonucleotide chain to the desired length, the DMT (4,4'-dimethoxytrityl) group at the 5'-end of the full-length oligonucleotide was removed by treatment with a solution of DCA (dichloroacetic acid) in toluene (3%), and then the column was washed with acetonitrile and finally dried with argon flow for 5 min.

Example 2

5'-Triphosphates

An aliquot of the primer support (25 mg, 1 μmol), to which the protected oligonucleotide was attached, was packed into a small synthesis column (0.25 ml, GE-Healthcare). The column was washed with dichloromethane (10 ml) and then a freshly prepared solution containing 2-chloro-4H-1,3,2-benzodioxa-phosphorin-4-one (1 M) and diisopropylethylamine (1.5 M) in dichloromethane was pushed stepwise in a time frame of 30 min over the column. The column was washed with dichloromethane (10 ml) and acetonitrile (10 ml), followed by 4 ml of a solution of 0.5 M tri-n-butylammonium pyrophosphate, or alternatively 0.5 M tetra-n-butylammonium pyrophosphate, in acetonitrile-pyridine (1:1) within 20 min. Next, the column was washed with acetonitrile (20 ml) and oxidizer solution (10 ml, Biosolve) was pushed through the column over 10 min. The column was finally washed with acetonitrile (20 ml) and dichloromethane (20 ml).

Example 3

Deprotection and Purification 3.1 Oligo-2'-deoxynucleotide-5'-triphosphates: The 5'-triphosphate-modified phosphodiester ODN 24218 (Table 2) was deprotected and cleaved from solid support by treatment with concentrated aqueous ammonia (40° C., 4 h). Purification was achieved on a SOURCE 15Q anion exchange column (CV: 6 ml, GE Healthcare) with the following gradient system: Buffer A: 10 mM sodium hydroxide, pH 12; buffer B: 2.5 M sodium chloride, 10 mM sodium hydroxide, pH 12. The chromatography system was an ÄKTA Purifier 10 with an Frac950 fraction collector (GE Healthcare). The product-containing fractions were desalted on a Biogel P4 column and lyophilized.
3.2 Oligoribonucleotide-5'-triphosphates: The 5'-triphosphate analog-modified phosphodiester ORN CPG-24299 and 24300 (Table 2) were deprotected and cleaved from solid support by treatment with aqueous ammonia/ethanol (3:1, 40° C., 4 h). Then, the 2'-TBDMS group was deprotected by treatment with a mixture of DMSO (75 μl), NMP (75 μl), triethylamine (75 μl) and triethylamine-trihydrofluoride (100 μl, Sigma-Aldrich) for 2 h at 65° C. After butanol precipitation, the oligoribonucleotide 5'-triphosphate was purified on a SOURCE 15Q anion exchange column (CV: 6 ml, GE Healthcare) with the following gradient system: Buffer A: 25 mM sodium acetate, pH 7.5; buffer B: 2.0 M sodium chloride, 25 mM sodium acetate, pH 7.5. The product-containing fractions were desalted on a Biogel P4 column and lyophilized.

TABLE 2

Sequences and characterization of oligonucleotides

| ID | Sequence [5'-3'] | M.W.[a] [Da] | M.W.[b] [Da] |
|---|---|---|---|
| CPG-24218 | (---)T-T-T-T-T-T-T-T-T-T (SEQ ID NO: 2) | 3220.0 | 3220.3 |
| CPG-24299 | (---)rU-rU-rU-rU-rU-rU-rU-rU-rU-rU (SEQ ID NO: 478) | 3239.7 | 3239.0 |
| CPG-24300 | (—CH$_2$—)rU-rU-rU-rU-rU-rU-rU-rU-rU-rU (SEQ ID NO: 508) | 3237.7 | 3239.9 |

[a]Calculated for free acid;
[b]Determined by LC-MS (ESI-TOF)

Example 4

Analytics

The oligonucleotides were analyzed on an Agilent 1100 HPLC system with the following modules: Micro vacuum-degaser (G1379A), binary pump (G1312A), well-plate sampler (G1367A), column oven (G1316A) and multiple wavelength detector (G1365B) which was coupled to a Bruker Esquire 3000+ ion trap mass spectrometer (negative mode): Column: Waters X-Bridge C18 2.5 μm 2.1×50 mm; column temperature 60° C.; UV-detection at 260 nm; flow: 0.2 mL/min; solvent A: 385 mM hexafluoroisopropanol (HFIP)+ 14.4 mM triethylamine (TEA); solvent B: methanol; injection volume: 10 μL; gradient: 0 min: 5% B, 15 min: 17.5% B, 50 min 24% B, 65 min: 45% B. Results are included in Table 2.

Example 5

Responsiveness of TLR7 and TLR8 to ORN

HEK293 cells were transiently transfected by electroporation with vectors expressing human or murine TLR7, human TLR8, and a 6×NF-κB luciferase reporter construct, as previously described. Jurk M et al. (2002) *Nat. Immunol.* 3:499. Cells are incubated for 16 h at 37° C. in a humidified incubator with various concentrations of ORN added. Cells are lysed and the amount of luciferase is determined with BriteLite on a luminometer (both from PerkinElmer).

Based on this assay, ORN of the invention is found to have an $EC_{50}$ of <100 μM for human TLR7. ORN of the invention is thus determined to be a potent agonist of human TLR7.

Also based on this assay, ORN of the invention is found to have an $EC_{50}$ of <100 μM for human TLR8. ORN of the invention is thus determined to be a potent agonist of human TLR8.

Example 6

Responsiveness of PBMC to ORN

Human peripheral blood mononuclear cells (PBMC) include immune cells that naturally express RIG-I, TLR7, and TLR8. Human PBMC are isolated from whole blood. Optionally pDCs and monocytes are isolated with the BDCA-4 pDC or CD14 monocyte isolation kit (Miltenyi Biotec), and mDCs are isolated with the BDCA-1 (CD1c) mDC isolation kit after depleting CD19+ B cells (Miltenyi Biotec). Purity is confirmed by staining with monoclonal antibody (mAb) to CD11c (Diaclone), CD14, HLA-DR, and CD123 (all from BD Biosciences), and is typically >80%. Purity of mDC fractions is confirmed by staining with mAb to CD14, CD19, and streptavidin. Cells are incubated for 16 h at 37° C. in a humidified incubator with various concentrations of ORN of the invention added. Culture supernatants are harvested and assayed by suitable ELISA for various specific cytokines including IFN-α and IL-12.

Results show that human PBMC are responsive to ORN of the invention.

Example 7

Use of ORN to Treat Cancer

The B16 (H-2$^b$) tumor line is an OVA-transfected clone derived from the murine B16 melanoma. Mayordomo J I et al. (1995) Nat. Med. 1:1297-1302. B16 tumor cells are cultured in vitro in conditioned medium in the presence of geneticin (2 mg/ml) and hygromycin B (60 μg/ml).

The murine colon adenocarcinoma CT26 tumor cell line (H-2$^d$) is purchased from American Type Culture Collection (Rockville, Md., USA) and maintained in vitro in conditioned medium.

Six- to ten-week-old male C57BU6 (H-2$^b$) and BALB/c (H-2$^d$) mice are obtained from The Jackson Laboratory (Bar Harbor, Me., USA).

$5 \times 10^4$ B16 or $2 \times 10^6$ CT26 tumor cells are resuspended in 0.1 ml of phosphate buffered saline (PBS) and inoculated subcutaneously in the flanks of mice. Various amounts of ORN of the invention (0-100 μg each) are suspended in 30 μl of PBS and injected into B16 tumors at day 11 and 14 after tumor inoculation. Up to five injections of ORN are delivered every 4 days into the tumors beginning day 11 after tumor challenge. Mice are examined twice a week for the presence and size of tumors. Tumor size represents the product of two perpendicular diameters. Mice are sacrificed when tumors reach 20 mm in their largest dimension or when ulceration and/or bleeding develop.

Results show that ORN of the invention can be used to treat cancer.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

The invention claimed is:

1. An isolated oligoribonucleotide (ORN) comprising a 5'-triphosphate analog provided as

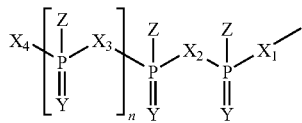

or a pharmaceutically acceptable salt of said ORN; wherein $X_1$ is selected from O, S, and NH and is linked to a 5' carbon of a 5' terminal nucleotide of the ORN;

$X_2$ and each $X_3$, when present, are independently selected from O, S, NH, $CH_2$, $CCl_2$, CHF, and $CF_2$;

$X_4$ is selected from OH, OR, SH, NHR, R, imidazole, and Nu-O—P(Z)(Y)$X_3$, wherein R is selected from a $C_1$-$C_{12}$ alkyl and a $C_6$-$C_{10}$ aryl, and wherein Nu is a nucleoside;

each Y is independently selected from O, S, and NH; and each Z is independently selected from H, OH, SH, $NH_2$, NHR', $BH_3$, $CF_2H$, $OPO_3H$, OR', and R', wherein R' is selected from $C_1$-$C_{12}$ alkyl, $C_2$-$C_{12}$ alkenyl, $C_2$-$C_{12}$ alkinyl, $C_6$-$C_{10}$ aryl, and $C_7$-$C_{22}$ alkylaryl; and n is an integer between 0 and 3, inclusive, provided that n is 0 only when $X_4$ is imidazole;

with the proviso that the 5'-triphosphate analog is not 5'-triphosphate.

2. A pharmaceutical composition comprising the isolated oligoribonucleotide of claim 1 and a pharmaceutically acceptable carrier.

3. The pharmaceutical composition of claim 2, further comprising an antigen.

4. A method of treating a condition selected from the group consisting of cancer, an allergic condition, asthma, or infection in a subject in need thereof, said method comprising the step of administering to the subject an amount of the oligoribonucleotide of claim 1 effective to treat the condition.

* * * * *